(12) United States Patent
Hayashi et al.

(10) Patent No.: US 12,384,763 B2
(45) Date of Patent: Aug. 12, 2025

(54) PROTEIN AND/OR PEPTIDE MODIFICATION MOLECULE

(71) Applicant: Osaka University, Osaka (JP)

(72) Inventors: Takashi Hayashi, Osaka (JP); Akira Onoda, Osaka (JP); Nozomu Inoue, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 972 days.

(21) Appl. No.: 17/432,838

(22) PCT Filed: Feb. 28, 2020

(86) PCT No.: PCT/JP2020/008357
§ 371 (c)(1),
(2) Date: Aug. 20, 2021

(87) PCT Pub. No.: WO2020/175680
PCT Pub. Date: Sep. 3, 2020

(65) Prior Publication Data
US 2022/0204481 A1 Jun. 30, 2022

(30) Foreign Application Priority Data
Feb. 28, 2019 (JP) .................. 2019-035340

(51) Int. Cl.
| C07D 403/12 | (2006.01) |
| C07D 249/04 | (2006.01) |
| C07D 403/04 | (2006.01) |
| C07D 493/10 | (2006.01) |
| C07D 495/04 | (2006.01) |

(52) U.S. Cl.
CPC ......... *C07D 403/12* (2013.01); *C07D 249/04* (2013.01); *C07D 403/04* (2013.01); *C07D 493/10* (2013.01); *C07D 495/04* (2013.01)

(58) Field of Classification Search
CPC .. C07D 403/12; C07D 249/04; C07D 403/04; C07D 493/10; C07D 495/04
USPC ........................................ 540/479
See application file for complete search history.

(56) References Cited

U.S. PATENT DOCUMENTS
2012/0252778 A1  10/2012 Miltz et al.
2016/0176864 A1   6/2016 Norris et al.

FOREIGN PATENT DOCUMENTS
| CN | 109096211 A | 12/2018 |
| CN | 109293727 A | 2/2019 |
| JP | 2008/540656 A | 11/2008 |
| JP | 2011/098956 A | 5/2011 |
| WO | WO-2005/042523 A1 | 5/2005 |
| WO | WO-2006/124692 A2 | 11/2006 |
| WO | WO-2007/131764 A2 | 11/2007 |
| WO | WO-2008/021388 A1 | 2/2008 |
| WO | WO-2011/053542 A1 | 5/2011 |
| WO | WO-2017/191304 A1 | 11/2017 |
| WO | WO-2017/197056 A1 | 11/2017 |

OTHER PUBLICATIONS

Danne, et al. "Synthesis and biological evaluation of novel triazole-biscoumarin conjugates as potential antitubercular and anti-oxidant agents." Research on Chemical Intermediates. May 31, 2018. vol. 44, No. 10. pp. 6283-6310.
Gannarapu, et al. "Synthesis of novel 1-substituted triazole linked 1,2-benzothiazine 1,1-dioxido propenone derivatives as potent anti-inflammatory agents and inhibitors of monocyte-to-macrophage differentiation." Medicinal Chemistry Communications. Jun. 12, 2015. vol. 6, No. 8. pp. 1494-1500.
Lu, et al. "Synthesis of C-4 and C-7 triazole analogs of zanamivir as multivalent sialic acid containing scaffolds." Carbohydrate Research. Jun. 9, 2007. vol. 342, No. 12. pp. 1636-1650.
Meyer, et al. "Synthesis and evaluation of new designed multiple ligands directed towards both peroxisome proliferator-activated receptor-γ and angiotensin II type 1 receptor." European Journal of Medicinal Chemistry. Aug. 31, 2018. vol. 158. pp. 334-352.
Mousazadeh, et al. "Synthesis spectroscopic characterization, and DFT studies 1,2,3-triazole-based organosilicon compounds." Journal of Molecular Structure. Mar. 20, 2018. vol. 1167. pp. 200-208.
Partial Search Report issued in European Patent Application No. 20762084.0. May 3, 2022.
Safa, et al. "A simple and efficient synthesis of organosilicon compounds containing 1,2,3-triazole moieties catalyzed by ZSM-5 zeolite-supported Cu—Co bimetallic oxides." Monatshefte fur Chemie-Chemical Monthly. Mar. 14, 2016. vol. 147, No. 11. pp. 1951-1961.
Setti, et al. "Studies on Penam Sulfones.—1. Synthesis and β-Lactamase Inhibitory Activity of 2β-Alkoxycarbonyl Penicillanic Acid Sulfones." The Journal of Antibiotics. Sep. 1996. vol. 49, No. 9. pp. 944-946.
Zischinsky, et al. "Discovery of orally available integrin α5β1 antagonists." Bioorganic & Medicinal Chemistry Letters. Oct. 28, 2009. vol. 20, No. 1. pp. 380-382.
David A. Ostrov, et al., Discovery of Novel DNA Gyrase Inhibitors by High-Throughput Virtual Screening, Antimicrobial Agents and Chemotherapy, Oct. 2007, pp. 3688-3698, vol. 51, No. 10, American Society for Microbiology.
Office Action dated Sep. 9, 2022 for EP Patent Application No. 20762084.0, 6 pages, European Patent Office, Munich Germany.
Chan et al "Modification of N-Terminal α-Amino Groups of Peptides and Proteins Using Ketenes" Journal of the American Chemical Society vol. 134, pp. 2589-2598, 2012.
Fletcher et al "Tandem Synthesis of 1-Formyl-1,2,3-Triazoles" Tetrahedron Letters vol. 58, pp. 4450-4454, 2017.

(Continued)

*Primary Examiner* — Kristin A Vajda
(74) *Attorney, Agent, or Firm* — Cesari and McKenna, LLP

(57) ABSTRACT

An object of the present invention is to provide a technique that allows other molecules/substances to be more selectively linked to the N-terminus in a simple and efficient manner, even in natural proteins etc. This object is achieved by reacting a compound represented by formula (1) or a salt thereof, or a hydrate or solvate of the compound or a salt thereof with a protein and/or peptide.

4 Claims, 63 Drawing Sheets

Specification includes a Sequence Listing.

(56) References Cited

OTHER PUBLICATIONS

Gangaprasad et al "Another Example of Organo-Click Reactions: Tempo-Promoted Oxidative Azide-Olefin Cycloaddition for the Synthesis of 1,2,3-Triazoles in Water" European Journal of Organic Chemistry vol. 2016, pp. 5642-5646, 2016.

Inoue et al "Site-Specific Modification of Proteins Through N-Terminal Azide Labeling and a Chelation-Assisted CuAAC Reaction" Bioconjugate Chemistry vol. 30, pp. 2427-2434, 2019.

L'Abbe et al "Molecular Rearrangements of 4-Iminomethyl-1,2,3-Triazoles, Replacement of 1-Aryl Substituents in 1H-1,2,3-Triazole-4-Carbaldehydes" Journal of Heterocyclic Chemistry vol. 27, pp. 2021-2027, 1990.

MacDonald et al "One-Step Site-Specific Modification of Native Proteins with 2-Pyridinecarboxyaldehydes" Nature Chemical Biology vol. 11, pp. 326-331, 2015.

Martos-Maldonado et al "Selective N-Terminal Acylation of Peptides and Proteins with a Gly-His Tag Sequence" Nature Communications vol. 9, pp. 1-13, 2018.

Onoda et al "Triazolecarbaldehyde Reagents for One-Step N-Terminal Protein Modification" ChemBioChem vol. 21, pp. 1274-1278, 2020.

Registry(STN) "1267222-01-4" 2011.

Registry(STN) "1329553-08-3" 2011.

Registry(STN) "1893001-96-1" 2016.

Schoffelen et al "Metal-Free and pH-Controlled Introduction of Azides in Proteins" Chemical Science vol. 2, pp. 701-705, 2011.

Yamamoto et al "A New Multicomponent Multicatalyst Reaction (MC)2R: Chemoselective Cycloaddition and Latent Catalyst Activation for the Synthesis of Fully Substituted 1,2,3-Triazoles" Organic Letters vol. 18, pp. 2644-2647, 2016.

Zhang et al "Novel Synthesis of 1,4,5-Trisubstituted 1,2,3-Triazoles via a One-Pot Three-Component Reaction of Boronic Acids, Azide, and Active Methylene Ketones" Tetrahedron vol. 69, pp. 2352-2356, 2013.

Fig. 36—2
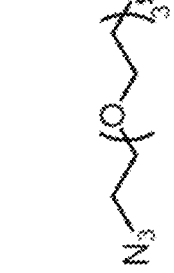
21: 58%[b]
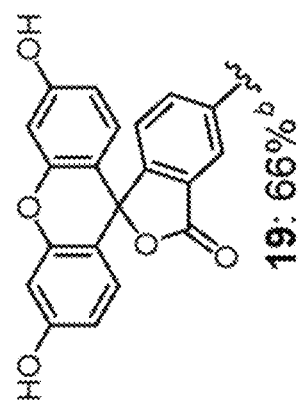
19: 66%[b]
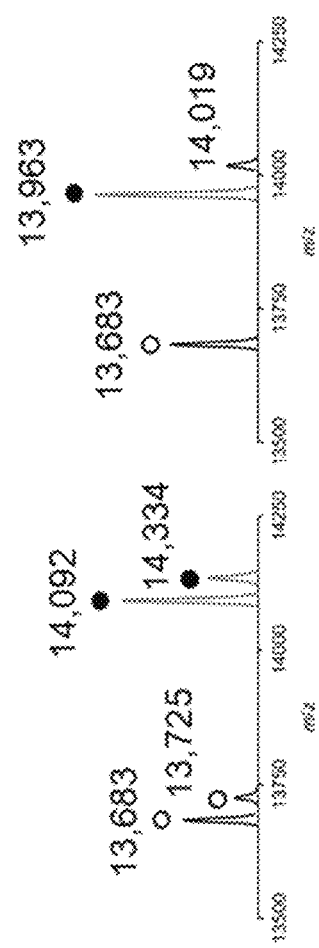

STEP 1

STEP 2

PEG OH
Mw. ~4000

Hydroxylamine 38
Mw. ~4000

SEQUENCE LISTING

<160> NUMBER OF SEQ ID NOS: 3

<210> SEQ ID NO 1
<211> LENGTH: 10
<212> TYPE: PRT
<213> ORGANISM: Homo sapiens

<400> SEQUENCE: 1

Asp Arg Val Tyr Ile His Pro Phe His Leu
1               5                   10

<210> SEQ ID NO 2
<211> LENGTH: 124
<212> TYPE: PRT
<213> ORGANISM: Bos taurus

<400> SEQUENCE: 2

Lys Glu Thr Ala Ala Ala Lys Phe Glu Arg Gln His Met Asp Ser Ser
1               5                   10                  15

Thr Ser Ala Ala Ser Ser Ser Asn Tyr Cys Asn Gln Met Met Lys Ser
            20                  25                  30

Arg Asn Leu Thr Lys Asp Arg Cys Lys Pro Val Asn Thr Phe Val His
        35                  40                  45

Glu Ser Leu Ala Asp Val Gln Ala Val Cys Ser Gln Lys Asn Val Ala
    50                  55                  60

Cys Lys Asn Gly Gln Thr Asn Cys Tyr Gln Ser Tyr Ser Thr Met Ser
65                  70                  75                  80

Ile Thr Asp Cys Arg Glu Thr Gly Ser Ser Lys Tyr Pro Asn Cys Ala
                85                  90                  95

Tyr Lys Thr Thr Gln Ala Asn Lys His Ile Ile Val Ala Cys Glu Gly
            100                 105                 110

Asn Pro Tyr Val Pro Val His Phe Asp Ala Ser Val
            115                 120

<210> SEQ ID NO 3
<211> LENGTH: 584
<212> TYPE: PRT
<213> ORGANISM: Homo sapiens

<400> SEQUENCE: 3

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys

```
            50                  55                  60
Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                     85                  90                  95

Glu Arg Asn Glu Cys Phe Leu Gln His Lys Asp Asp Asn Pro Asn Leu
                    100                 105                 110

Pro Arg Leu Val Arg Pro Glu Val Asp Val Met Cys Thr Ala Phe His
                115                 120                 125

Asp Asn Glu Glu Thr Phe Leu Lys Lys Tyr Leu Tyr Glu Ile Ala Arg
            130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Glu Ala Lys Arg Met Pro Cys Ala
            435                 440                 445

Glu Asp Tyr Leu Ser Val Val Leu Asn Gln Leu Cys Val Leu His Glu
450                 455                 460

Lys Thr Pro Val Ser Asp Arg Val Thr Lys Cys Cys Thr Glu Ser Leu
465                 470                 475                 480
```

```
Val Asn Arg Arg Pro Cys Phe Ser Ala Leu Glu Val Asp Glu Thr Tyr
            485             490             495

Val Pro Lys Glu Phe Asn Ala Glu Thr Phe Thr Phe His Ala Asp Ile
            500             505             510

Cys Thr Leu Ser Glu Lys Glu Arg Gln Ile Lys Lys Gln Thr Ala Leu
        515             520             525

Val Glu Leu Val Lys His Lys Pro Lys Ala Thr Lys Glu Gln Leu Lys
        530             535             540

Ala Val Met Asp Asp Phe Ala Ala Phe Val Glu Lys Cys Cys Lys Ala
545             550             555             560

Asp Asp Lys Glu Thr Cys Phe Ala Glu Glu Gly Lys Lys Leu Val Ala
            565             570             575

Ala Ser Gln Ala Ala Leu Gly Leu
            580
```

PROTEIN AND/OR PEPTIDE MODIFICATION MOLECULE

CROSS REFERENCE TO RELATED APPLICATIONS

This patent application is the national stage of International Application No. PCT/JP2020/008357, filed on Feb. 28, 2020, which claims priority from Japanese Application No. 2019-035,340, filed on Feb. 28, 2019, the disclosures of which are incorporated by reference herein in their entirety as part of the present application.

TECHNICAL FIELD

The present invention relates to a molecule for protein and/or peptide modification and the like.

BACKGROUND ART

Techniques for linking other molecules/substances to proteins and/or peptides (which hereinafter may be referral to as "proteins etc.") are important in the preparation of antibody-drug conjugates, protein reagents labeled with fluorescent probes, protein immobilization inorganic materials, and the like. For example, modification of proteins etc. with an azido group is a technique that enables the introduction of various functional molecules by an alkyne-azide cycloaddition reaction (CuAAC), which has been widely applied in the field of bioimaging etc. because of bioorthogonality.

CITATION LIST

Non-Patent Literature

NPL 1: Metal-free and pH-controlled introduction of azides in proteins, Sanne Schoffelen, Mark B. van Eldijk, Bait Rooijakkers, Reinout Raijmakers, Albert J. R. Heck and Jan C. M. van Hest, Chemical Science, 2011, 2, 701.

NPL 2: Selective N-terminal acylation of peptides and proteins with a Gly-His tag sequence, M. C. Martos-Maldonado, C. T. Hjuler, K. K. Sorensen, M. B. Thygesen, J. E. Rasmussen, K. Villadsen, S. R. Midtgaard, S. Kol, S. Schoffelen, K. J. Jensen, Nature Communications, 2018, 9, 3307.

NPL 3: Modification of N-Terminal α-Amino Groups of Peptides and Proteins Using Ketenes, A. O.-Y. Chan, C.-M. Ho, H.-C. Chong, Y.-C. Leung, J.-S. Huang, M.-K. Wong, C.-M. Che, Journal of the American Chemical Society, 2012, 134, 2589.

SUMMARY OF INVENTION

Technical Problem

When pursuing the investigation of the introduction position in linking other molecules/substances to proteins etc., the present inventors focused on the following three points. The first point is that the N-terminus is a position that all monomeric proteins have only one of, which is a universal modification base point. The second point is that the N-terminus is rarely involved in the protein active sites (molecular binding site and catalytic reaction center) or the protein functional sites, and that the effect of structural changes associated with modification is considered to be small. The third point is that the N-terminus is considered to be less likely to compete with other amino acid residues (e.g., lysine, cysteine, and glutamine) for reaction due to differences in $pK_a$; while at the C-terminus, such reaction selectivity based on $pK_a$ is considered to be difficult to achieve. Therefore, the inventors focused on the N-termini of proteins etc. as a position to link other molecules/substances.

Various methods have been reported to link other molecules/substances to the N-termini of proteins etc. (NPL 1 to NPL 3). However, these methods are considered to be insufficient in terms of simplicity or N-terminal modification selectivity. For example, although chemical bonding methods or lipid-modifying enzyme methods, which recognize a specific amino acid sequence, can introduce other molecules/substances specifically into the N-terminus, they require a protein etc. in which a special amino acid sequence or a special amino acid residue is inserted. The preparation of such a protein etc. is laborious, and these methods cannot be applied to natural proteins etc. An amide bond formation reaction using an activated ester or ketene is simple to perform, and can be applied to natural proteins etc.; however, it cannot introduce other molecules/substances specifically into the N-terminus because a side reaction with lysine residues or the like can proceed.

Therefore, an object of the present invention is to provide a technique that allows other molecules/substances to be more selectively linked to the N-termini of all proteins and/or peptides in a simple and efficient manner.

Solution to Problem

The present inventors conducted extensive research to solve the above problems. They found that the problems can be solved by reacting a compound represented by formula (1) or a salt thereof, or a hydrate or solvate of the compound or a salt thereof, with a protein and/or peptide. The inventors conducted further research based on this finding, and the present invention has thus been accomplished.

Specifically, the present invention includes the following embodiments.

Item 1. A compound represented by formula (1) or a salt thereof, or a hydrate or solvate of the compound or a salt thereof,

wherein one of $R^1$ and $R^2$ represents $—N(—R^4)—$ (wherein $R^4$ represents an organic group or a group derived from an inorganic material), and the other represents $=N—$; and $R^3$ represents a hydrogen atom, an organic group, or a group derived from an inorganic material.

Item 2. The compound or a salt thereof, or a hydrate or solvate of the compound or a salt thereof according to Item 1, wherein the compound is represented by formula (1Aa):

wherein $R^4$ is as defined above.

Item 3. The compound or a salt thereof, or a hydrate or solvate of the compound or a salt thereof according to Item 1 or 2, wherein the organic group is a group derived from an organic molecule or an organic molecular complex, and the organic molecule or the organic molecular complex is a functional substance.

Item 4. The compound or a salt thereof, or a hydrate or solvate of the compound or a salt thereof according to Item 3, wherein the functional substance is a pharmaceutical compound, a luminescent molecule, a macromolecular compound, a ligand, a molecule to which a ligand binds, an antigenic protein, an antibody, a protein, a nucleic acid, a saccharide, a lipid, a cell, a virus, a label, a carbon electrode, a carbon nanomaterial, a linker, a spacer molecule, or a complex or linked molecule thereof.

Item 5. The compound or a salt thereof, or a hydrate or solvate of the compound or a salt thereof according to any one of Items 1 to 4, wherein the inorganic material is an electrode material, metal fine particles, metal oxide fine particles, semiconductor particles, or magnetic particles.

Item 6. A reagent comprising the compound or a salt thereof, or a hydrate or solvate of the compound or a salt thereof according to any one of Items 1 to 5.

Item 7. The reagent according to Item 6, which is a reagent for protein and/or peptide modification.

Item 8. A method for producing the compound or a salt thereof, or a hydrate or solvate of the compound or a salt thereof according to any one of Items 1 to 5, the method comprising:

reacting a compound represented by formula (2) or a salt thereof,

wherein $R^4$ represents an organic group or a group derived from an inorganic material; and $R^5$ represents —$N_3$, —X (wherein X represents a halogen atom), —$B(OH)_2$, —$B(OR^{51})_2$ (wherein each $R^{51}$ is the same or different and represents a hydrocarbon group, with the proviso that two $R^{51}$s, taken together with the adjacent oxygen atoms, may form a ring), or —$N_2^+$,
with a compound represented by formula (3), a compound represented by formula (4), or a compound represented by formula (9):

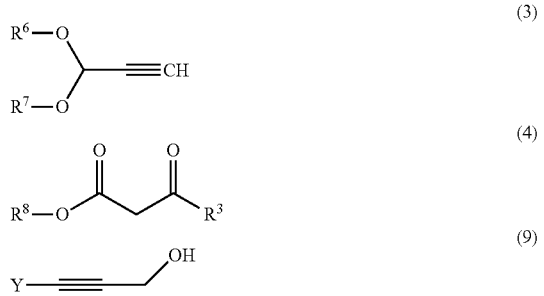

wherein $R^3$ represents a hydrogen atom, an organic group, or a group derived from an inorganic material; $R^6$, $R^7$, and $R^8$ are the same or different and each represents an alkyl group; and Y represents a reactive group.

Item 9. A method for producing the compound or a salt thereof, or a hydrate or solvate of the compound or a salt thereof according to any one of Items 1 to 5, the method comprising:

reacting a compound represented by formula (5):

wherein $R^4$ represents an organic group or a group derived from an inorganic material; and $R^9$ represents —$NR^{9a}R^{9b}$ (wherein $R^{9a}$ and $R^{9b}$ are the same or different and each represents a hydrogen atom or an alkyl group),
with a compound represented by formula (6):

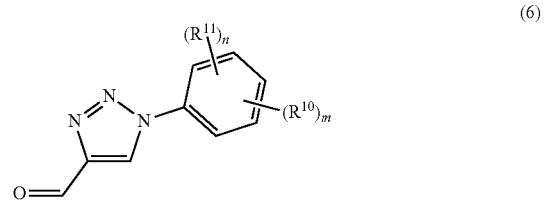

wherein $R^{10}$ represents an electron-withdrawing group; $R^{11}$ represents —$R^{11a}$-$R^{12}$ (wherein $R^{11a}$ represents a single bond or a linker; and $R^{12}$ represents a carrier); n represents 0 or 1; and m represents an integer of 1 to 5.

Item 10. A compound represented by formula (6'):

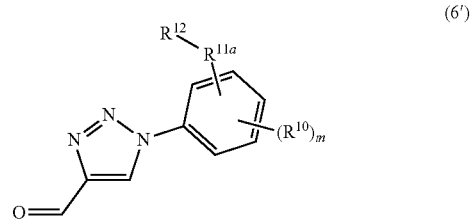

wherein $R^{10}$ represents an electron-withdrawing group; $R^{11a}$ represents a single bond or a linker; $R^{12}$ represents a carrier; and m represents an integer of 1 to 5.

Item 11. A compound represented by formula (7) or a salt thereof, or a hydrate or solvate of the compound or a salt thereof,

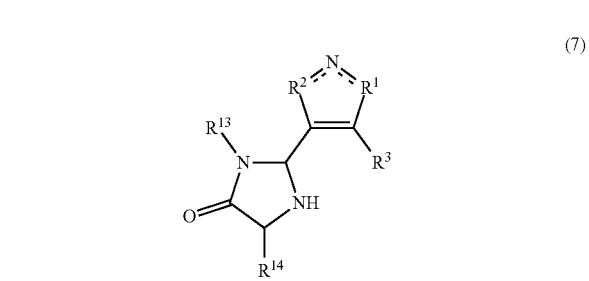

wherein one of $R^1$ and $R^2$ represents —N(—$R^4$)— (wherein $R^4$ represents an organic group or a group derived from an inorganic material), and the other represents =N—; $R^3$ represents a hydrogen atom, an organic group, or a group derived from an inorganic material; a double line composed of a dotted line and a solid line represents a single bond or a double bond; $R^{13}$ represents a group in which the N-terminal amino acid residue and —NH— adjacent thereto are excluded from a protein or peptide; and $R^{14}$ represents the side chain of the N-terminal amino acid residue of the protein or peptide.

Item 12. A method for producing the compound or a salt thereof, or a hydrate or solvate of the compound or a salt thereof according to Item 11, the method comprising reacting a protein and/or a peptide with the compound or a salt thereof, or a hydrate or solvate of the compound or a salt thereof according to any one of Items 1 to 5.

Advantageous Effects of Invention

The present invention makes it possible to provide a technique that allows other molecules/substances to be more selectively linked to the N-terminus in a simple and efficient manner, even in natural proteins etc.

BRIEF DESCRIPTION OF DRAWINGS

FIGS. 36A and 36B show the results of LC/MS analysis of RNaseA modified at the N-terminus by a successive reaction using a resin on which a reactant is immobilized (27/PS resin) (Example 12-6). The peaks corresponding to the modified proteins are shown as "●" (solid circles), and the peaks corresponding to the unmodified protein are shown as "○" (hollow circles).

FIGS. 73A and 73B show the scheme and results of a reaction of N-terminal modification to HSA2 and a reaction of modification with compound 26 (Example 23-2-3).

DESCRIPTION OF EMBODIMENTS

Figure 1:
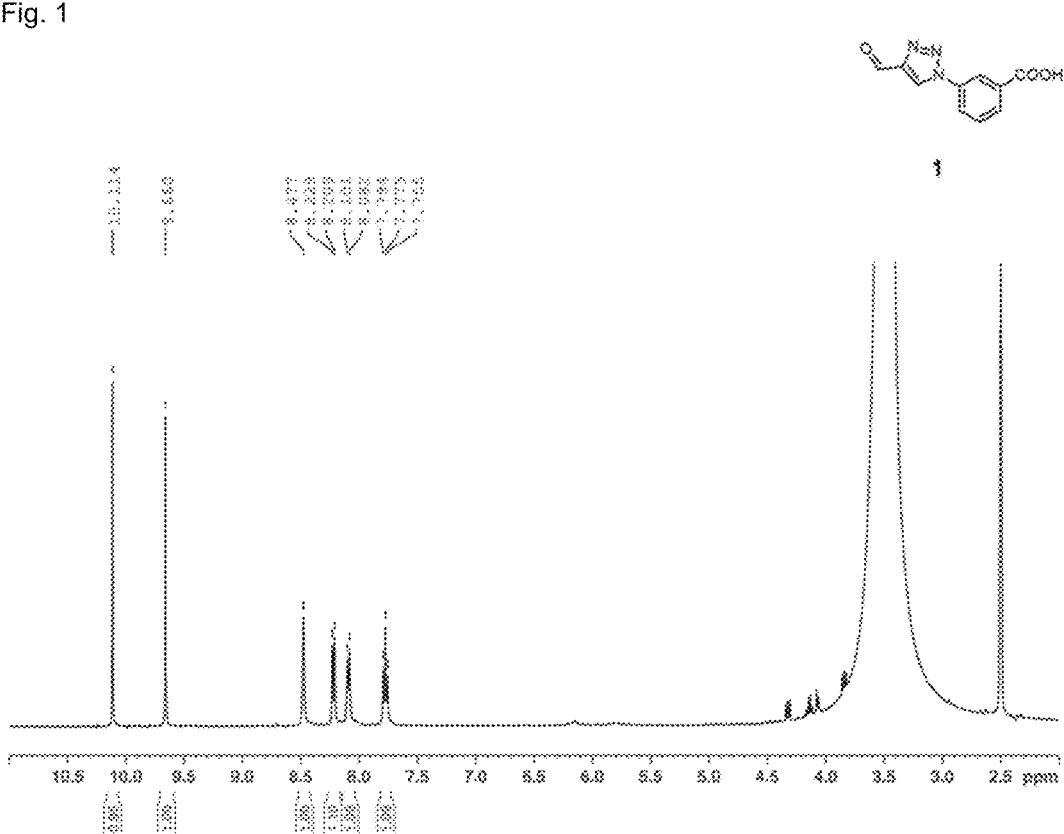
FIG. 1 shows the $^1$H NMR spectrum (400 MHz, DMSO-$d_6$) of compound 1.

In the present specification, the terms "comprise" and "contain" include the concepts of "comprise," "contain," "consist essentially of," and "consist of."

1. Protein and/or Peptide Modification Molecule

In one embodiment, the present invention relates to a compound represented by formula (1) or a salt thereof, or a hydrate or solvate of the compound or a salt thereof (in the present specification, these may be collectively referral to as "the modification molecule of the present invention"):

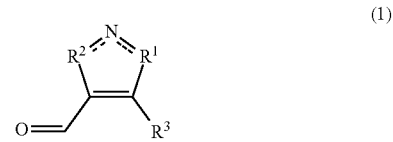

(1)

wherein one of R¹ and R² represents —N(—R⁴)— (wherein R⁴ represents an organic group or a group derived from an inorganic material), and the other represents =N—; and R³ represents a hydrogen atom, an organic group, or a group derived from an inorganic material.

The modification molecule of the present invention is described below.

1-1. Compound

One of R¹ and R² represents —N(—R⁴)— (wherein R⁴ represents an organic group or a group derived from an inorganic material), and the other represents =N—. A double line composed of a dotted line and a solid line represents a single bond or a double bond, and whether it is a single bond or a double bond is determined depending on which of R¹ and R² is —N(—R⁴)— or =N—.

Specifically, when R¹ is —N(—R⁴)—, and R² is =N—, formula (1) is formula (1A):

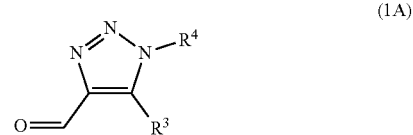

(1A)

wherein R³ and R⁴ are as defined above; and
when R¹ is =N—, and R² is —N(—R⁴)—, formula (1) is formula (1B):

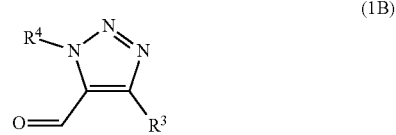

(1B)

wherein R³ and R⁴ are as defined above.

In the present invention, it is preferable that R¹ is —N(—R⁴)— and that R² is =N—; i.e., that formula (1) is formula (1A)).

The organic group is not particularly limited as long as it is a group derived from an organic molecule or an organic molecular complex, for example, a group obtained by removing one or more atoms from an organic molecule or an organic molecular complex. The organic molecule is not particularly limited and may be natural, or synthetic or artificial. The organic molecular complex is not particularly limited, and examples include a complex (or an organism) in which a plurality of molecules including one or more organic molecules are linked. The mode of the linkage is not particularly limited, and examples include hydrogen bonds, electrostatic forces, Van der Waals forces, hydrophobic bonds, covalent bonds, coordinate bonds, and the like. These bonds may be made via a linker (see the linkers described later for specific examples). The organic molecule or organic molecular complex is preferably a functional substance. Specific examples thereof include pharmaceutical compounds, luminescent molecules, macromolecular compounds, ligands, molecules to which a ligand binds, antigenic proteins, antibodies, proteins, nucleic acids, saccharides, lipids, cells, viruses, labels (e.g., radioisotopic labels), carbon electrodes, carbon nanomaterials, linkers, spacer molecules (e.g., polyethylene glycol or derivatives thereof, and peptides (as an example, a peptide containing an amino acid sequence that is cleaved by an enzyme in a cell)), and complexes and linked molecules thereof.

In one embodiment of the present invention, one or more modification molecules of the present invention may be linked as a partial structure in the organic group (e.g., at an end). An example of the modification molecule of the present invention in this case is a compound represented by formula (1AA):

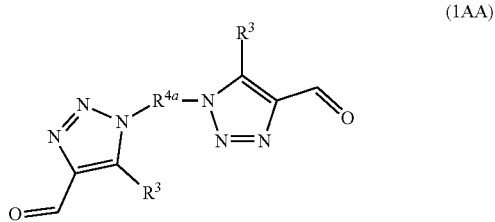

wherein $R^3$ is as defined above, and $R^3$, in each occurrence, is the same or different; and $R^{4a}$ represents a divalent organic group. $R^{4a}$ may contain a partial structure of the modification molecule of the present invention.

The inorganic material is a material that contains or does not contain one or more metal atoms, and is not particularly limited. Examples of inorganic materials include electrode materials, metal fine particles, metal oxide fine particles, semiconductor particles, magnetic particles, and the like. The inorganic material may retain an organic molecule or an organic molecular complex.

The organic group or group derived from an inorganic material may have a reactive group. In this case, another substance can be further linked via the reactive group. Examples of reactive groups include ethynyl, ethynylene, vinyl, azido, epoxy, aldehyde, oxylamino, halogen, and the like. Ethynyl and ethynylene groups are each known to undergo a 1,3-dipolar cycloaddition reaction with an azido group to form a 1,2,3-triazole ring. A vinyl group reacts with a thiol group to form a bond. An epoxy group reacts with an amino group or a thiol group to form a bond. An aldehyde group reacts with an amino group to form a Schiff base, which is reduced to form a bond. An oxylamino group reacts with a ketone group or an aldehyde group to form an oxime.

An azido group is known to undergo a 1,3-dipolar cycloaddition reaction with an alkynyl group to form a 1,2,3-triazole ring.

$R^3$ represents a hydrogen atom, an organic group, or a group derived from an inorganic material. Examples of the organic group and inorganic material include those mentioned above as examples of the organic group and inorganic-material-derived group represented by $R^4$. When $R^3$ is an organic group or a group derived from an inorganic material, the organic group or group derived from an inorganic material preferably has a reactive group. In this case, another substance can be further linked via the reactive group, as described above.

In one embodiment of the present invention, $R^3$ is a hydrogen atom. In this case, formula (1) is, for example, formula (1a), (1Aa), or (1Ba):

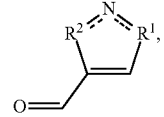

(1a)

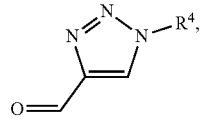

(1Aa)

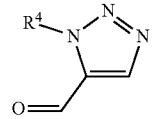

(1Ba)

wherein $R^1$, $R^2$, and $R^4$ are as defined above.

The compound represented by formula (1) encompasses stereoisomers and optical isomers, and these isomers are not particularly limited.

The salt of the compound represented by formula (1) is not particularly limited. The salt may be an acid salt or a basic salt. Examples of acid salts include inorganic acid salts, such as hydrochloride, hydrobromide, sulfate, nitrate, perchlorate, and phosphate; and organic acid salts, such as acetate, propionate, tartrate, fumarate, maleate, malate, citrate, methanesulfonate, and p-toluenesulfonate. Examples of basic salts include alkali metal salts, such as sodium salts and potassium salts; alkaline earth metal salts, such as calcium salts and magnesium salts; salts with ammonia; salts with organic amines, such as morpholine, piperidine, pyrrolidine, monoalkylamine, dialkylamine, trialkylamine, mono(hydroxyalkyl)amine, di(hydroxyalkyl)amine, and tri(hydroxyalkyl)amine; and the like.

The compound represented by formula (1) can also be a hydrate or a solvate. Examples of solvents include organic solvents (e.g., ethanol, glycerol, and acetic acid), and the like.

1-2. Synthesis Method 1

The compound represented by formula (1) can be synthesized by various methods. As an example, the compound represented by formula (1) can be synthesized by a method comprising reacting a compound represented by formula (2) or a salt thereof, $$R^4 - R^5 \qquad (2),$$

wherein $R^4$ is as defined above; and $R^5$ represents —$N_3$, —X (wherein X represents a halogen atom), —$B(OH)_2$, —$B(OR^{51})_2$ (wherein each $R^{51}$ is the same or different and represents a hydrocarbon group, with the proviso that two $R^{51}$s, taken together with the adjacent oxygen atoms, may form a ring), or —$N_2^+$,
with a compound represented by formula (3), a compound represented by formula (4), or a compound represented by formula (9):

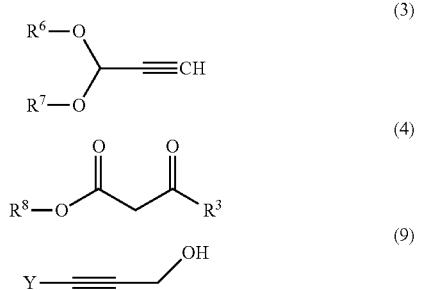

wherein $R^3$ is as defined above; $R^6$, $R^7$, and $R^8$ are the same or different and each represents an alkyl group; and Y represents a reactive group.

Examples of the halogen atom represented by X include fluorine, chlorine, bromine, iodine, and the like. Preferably, the halogen atom represented by X is, for example, bromine.

Examples of the hydrocarbon group represented by $R^{51}$ include alkyl, cycloalkyl, and the like.

The alkyl group represented by $R^{51}$ encompasses both linear alkyl groups and branched alkyl groups. The number of carbon atoms in the alkyl group is not particularly limited, and is, for example, 1 to 8. Specific examples of the alkyl group include methyl, ethyl, n-propyl, isopropyl, n-butyl, isobutyl, tert-butyl, sec-butyl, n-pentyl, neopentyl, n-hexyl, 3-methylpentyl, n-heptyl, n-octyl, and the like.

The number of carbon atoms in the cycloalkyl group represented by $R^{51}$ is not particularly limited, and is, for example, 3 to 10, and preferably 4 to 10. Specific examples of the cycloalkyl group include cyclopropyl, cyclobutyl, cyclopentyl, cyclohexyl, cycloheptyl, cyclooctyl, and the like.

The ring formed by two $R^{51}$s taken together with the adjacent oxygen atoms may be substituted with alkyl or the like.

As the alkyl groups represented by $R^6$, $R^7$, and $R^8$, linear lower alkyl groups are usually adopted, and ethyl is preferably adopted.

Examples of the reactive group represented by Y include those mentioned above as examples of the reactive group that may be contained in the organic group or group derived from an inorganic material. Y is preferably a halogen atom (Y').

The details are described below for each type of material used.

1-2-1. Case 1 (Case in which $R^5$ is —$N_3$, and a Compound Represented by Formula (3) is Used)

The amount of the compound represented by formula (2) used, as the number of moles of the functional group to be reacted (azido group in this case), is generally preferably 0.1 to 5 moles, and more preferably 0.3 to 2 moles, per mole of the compound represented by formula (3), in terms of yield and the like.

This reaction is generally performed in the presence of a reaction solvent Examples of reaction solvents include, but are not particularly limited to, water, methanol, tetrahydrofuran, dioxane, dimethyl sulfoxide, and the like. These solvents may be used singly, or in a combination of two or more. It is preferable to add a buffer, such as a phosphate buffer, to the solvent. When water is used, the pH of this reaction is preferably near neutral, specifically preferably 6 to 8.5, more preferably 6.5 to 8, and even more preferably 7 to 7.5.

This reaction is preferably performed in the presence of a suitable catalyst. The catalyst is, for example, a copper catalyst Examples of copper catalysts include divalent copper, such as copper sulfate; monovalent copper, such as copper iodide; and the like. Further, a reducing agent (e.g., hydroquinone or sodium ascorbate), a ligand, etc. can also be used in this reaction.

The amount of the copper catalyst used is generally preferably 0.1 to 5 moles, per mole of the azido group-containing protein or peptide of the present invention, in terms of yield and the like.

In addition to the above components, additives may be suitably used in this reaction as long as the progress of the reaction is not significantly impaired.

The reaction can be performed under heating, at room temperature, or under cooling; and is generally preferably performed at a temperature at which the azido group-containing protein or peptide of the present invention is not significantly denatured, for example, 0 to 45° C. (in particular 0 to 40° C.). The reaction time is not particularly limited and may be generally 30 minutes to 3 hours, in particular 1 to 2 hours.

The progress of the reaction can be monitored by chromatography or other usual methods. After completion of the reaction, the solvent can be distilled off, and the product can be isolated and purified by chromatography, recrystallization, or other usual methods as necessary. The structure of the product can be identified by elemental analysis, MS (ESI-MS) analysis, IR analysis, $^1$H-NMR, $^{13}$C-NMR, etc.

1-2-2. Case 2 (Case in which $R^5$ is a Group Other than —$N_3$, and a Compound Represented by Formula (3) is Used)

This case is the same as case 1, except that an azidating agent for converting $R^5$ to an azido group is added to the reaction system.

Examples of the azidating agent include inorganic azides, such as sodium azide; sulfonyl azide; silylazide; phosphoryl azide; alkylammonium azide; and the like.

The amount of the azidating agent used is generally preferably 0.1 to 5 moles, and more preferably 0.3 to 2 moles, per mole of the compound represented by formula (2), in terms of yield and the like.

1-2-3. Case 3 (Case in which a Compound Represented by Formula (4) is Used)

In this case, the compound represented by formula (1) can be synthesized through several steps after a reaction of the compound represented by formula (2) with the compound represented by formula (4). For example, in this case, the compound represented by formula (1) can be synthesized according to the following scheme.

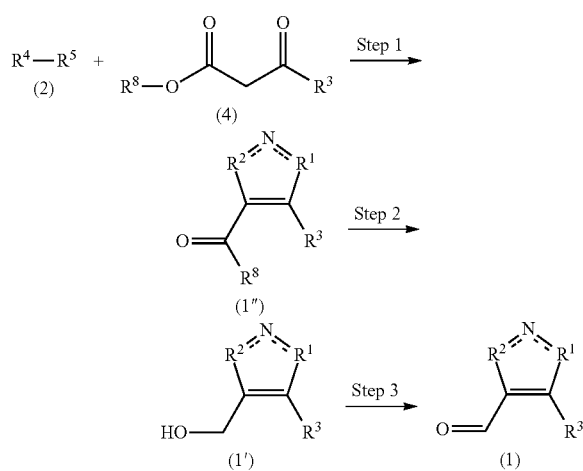

wherein $R^1$, $R^2$, $R^3$, $R^4$, $R^5$, and $R^8$ are as defined above.

Step 1

The amount of the compound represented by formula (2) used, as the number of moles of the functional group to be reacted (azido group in this case), is generally preferably 0.1 to 5 moles, and more preferably 0.3 to 2 moles, per mole of the compound represented by formula (4), in terms of yield and the like.

The solvent to be used is not limited as long as it does not adversely affect the reaction. Examples include water, alcohol-based solvents (e.g., methanol, ethanol, isopropanol, n-butanol, trifluoroethanol, and ethylene glycol), ketone-based solvents (e.g., acetone and methyl ethyl ketone), ether-based solvents (e.g., tetrahydrofuran, dioxane, diethyl ether, dimethoxyethane, and diglyme), ester-based solvents (e.g., methyl acetate and ethyl acetate), aprotic polar solvents (e.g., acetonitrile, N,N-dimethylformamide, and dimethyl sulfoxide), halogenated hydrocarbon-based solvents (e.g., methylene chloride and ethylene chloride), and mixtures thereof. The solvent is preferably a mixture of water and an aprotic polar solvent (in particular, dimethylformamide).

Step 1 is generally performed in the presence of a base. The base may be, for example, an organic base. Examples of the organic base include trialkylamines (e.g., trimethylamine, triethylamine, and N,N-diisopropylethylamine), pyridine, quinoline, piperidine, imidazole, picoline, 4-dimethylaminopyridine, N,N-dimethylaniline, N-methylmorpholine, 1,5-diazabicyclo[4.3.0]non-5-ene (DBN), 1,4-diazabicyclo[2.2.2]octane (DABCO), 1,8-diazabicyclo[5.4.0]undec-7-ene (DBU), and the like. When these bases are in the form of liquid, they can also be used as solvents. These bases may be used singly, or in a combination of two or more. The base is preferably piperidine.

When a base is used, the amount of the base is generally 0.05 to 1 mole, and preferably 0.1 to 0.5 moles, per mole of the compound represented by formula (4).

The reaction temperature is not particularly limited. The reaction is generally performed under cooling, at room temperature, or under heating. The reaction may be performed at a temperature of preferably about 50 to 100° C., more preferably about 70 to 90° C., for 1 to 30 hours.

After completion of the reaction, the solvent can be distilled off, and the product can be isolated and purified by chromatography, recrystallization, or other usual methods.

The structure of the product can be identified by elemental analysis, MS (ESI-MS) analysis, IR analysis, $^1$H-NMR, $^{13}$C-NMR, etc.

Step 2

In step 2, the compound represented by formula (1″) is reacted in the presence of a reducing agent and an appropriate amount of a base.

Examples of the reducing agent include sodium borohydride, zinc borohydride ($Zn(BH_4)_2$), tetramethylammonium triacetoxyborohydride, lithium tri-sec-butyl borohydride, borane, borane-THF complex, borane-dimethyl sulfide complex, lithium aluminum hydride, diisobutylaluminum hydride, lithium borohydride, and the like. These reducing agents may be used singly, or in a combination of two or more. The reducing agent is preferably sodium borohydride.

The amount of the reducing agent used is generally 1 to 15 moles, and preferably 3 to 10 moles, per mole of the compound represented by formula (1″).

As the base, for example, an inorganic base can be used. Examples of the inorganic base include alkali metals (e.g., sodium and potassium), alkali metal hydrogencarbonates (e.g., lithium hydrogencarbonate, sodium hydrogencarbonate, and potassium hydrogencarbonate), alkali metal hydroxides (e.g., lithium hydroxide, sodium hydroxide, potassium hydroxide, and cesium hydroxide), alkali metal carbonates (e.g., lithium carbonate, sodium carbonate, potassium carbonate, and cesium carbonate), alkali metal lower ($C_1$-$C_4$) alkoxides (e.g., sodium methoxide, sodium ethoxide, and potassium tert-butoxide), alkali metal hydrides (e.g., sodium hydride and potassium hydride), and the like. These bases may be used singly, or in a combination of two or more. The base is preferably an alkali metal lower ($C_1$-$C_4$) alkoxide (in particular, sodium methoxide).

The solvent to be used is not limited as long as it does not adversely affect the reaction. Examples include water, alcohol-based solvents (e.g., methanol, ethanol, isopropanol, n-butanol, trifluoroethanol, and ethylene glycol), ketone-based solvents (e.g., acetone and methyl ethyl ketone), ether-based solvents (e.g., tetrahydrofuran, dioxane, diethyl ether, dimethoxyethane, and diglyme), ester-based solvents (e.g., methyl acetate and ethyl acetate), aprotic polar solvents (e.g., acetonitrile, N,N-dimethylformamide, and dimethyl sulfoxide), halogenated hydrocarbon-based solvents (e.g., methylene chloride and ethylene chloride), and mixtures thereof. The solvent is preferably an alcohol-based solvent (in particular, methanol).

The reaction temperature is not particularly limited. The reaction is generally performed under cooling, at room temperature, or under heating. The reaction may be performed at a temperature of preferably about 0 to 60° C., more preferably about 10 to 40° C. for 1 to 30 hours.

After completion of the reaction, the solvent can be distilled off, and the product can be isolated and purified by chromatography, recrystallization, or other usual methods. The structure of the product can be identified by elemental analysis, MS (ESI-MS) analysis, IR analysis, $^1$H-NMR, $^{13}$C-NMR, etc.

Step 3

In step 3, the compound represented by formula (1′) is reacted in the presence of an oxidising agent.

As the oxidizing agent, for example, manganese dioxide can be used. Other examples of usable oxidizing agents include selenium dioxide, nitroxyl radicals such as 2,2,6,6- tetramethylpiperidine 1-oxyl (TEMPO) and 2-azaadamantane-N-oxyl (AZADO), and the like. These oxidizing agents may be used singly, or in a combination of two or more.

The amount of the oxidizing agent used is generally 3 to 20 moles, and preferably 5 to 15 moles, per mole of the compound represented by formula (1').

The solvent to be used is not limited as long as it does not adversely affect the reaction. Examples include ketone-based solvents (e.g., acetone and methyl ethyl ketone), ether-based solvents (e.g., tetrahydrofuran, dioxane, diethyl ether, dimethoxyethane, and diglyme), ester-based solvents (e.g., methyl acetate and ethyl acetate), aprotic polar solvents (e.g., acetonitrile, N,N-dimethylformamide, and dimethyl sulfoxide), halogenated hydrocarbon-based solvents (e.g., chloroform, methylene chloride, and ethylene chloride), and mixtures thereof. The solvent is preferably a halogenated hydrocarbon-based solvent (in particular, chloroform).

The reaction temperature is not particularly limited. The reaction is generally performed under cooling, at room temperature, or under heating. The reaction may be performed at a temperature of preferably about 0 to 60° C., more preferably about 10 to 40° C. for 1 to 30 hours.

After completion of the reaction, the solvent can be distilled off, and the product can be isolated and purified by chromatography, recrystallization, or other usual methods. The structure of the product can be identified by elemental analysis, MS (ESI-MS) analysis, IR analysis, $^1$H-NMR, $^{13}$C-NMR, etc.

1-2-4. Case 4 (case in which $R^5$ is —$N_3$, and a Compound Represented by Formula (9) is Used)

In this case, the compound represented by formula (1) can be synthesized through several steps after a reaction of the compound represented by formula (2) with the compound represented by formula (9). For example, in this case, the compound represented by formula (1) can be synthesized according to the following scheme.

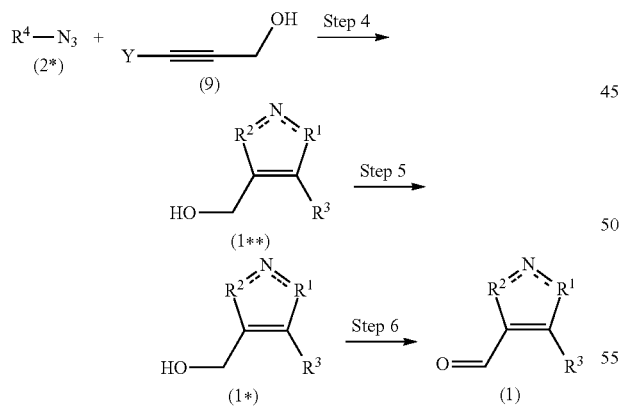

Step 4 can be performed in accordance with or based on case 1 described above. Step 6 can be performed in accordance with or based on step 3 described above. Step 5 can be performed by reacting a compound represented by formula (1**) with a compound represented by formula (10): $R^3$-Z. Z is a reactive group that reacts with Y. When Y is halogen, for example, —B(OH)$_2$ can be adopted as Z. The reaction conditions of step 5 can be determined based on known information, according to the types of Y and Z.

1-3. Synthesis Method 2

In addition to synthesis method 1 above, the compound represented by formula (1) can be synthesized by, for example, a method comprising reacting a compound represented by formula (5): $R^4$-$R^9$ (5), wherein $R^4$ is as defined above; and $R^9$ represents
—$NR^{9a}R^{9b}$ (wherein $R^{9a}$ and $R^{9b}$ are the same or different and each represents a hydrogen atom or an alkyl group) with a compound represented by formula (6):

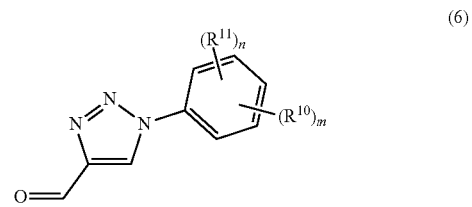

wherein $R^{19}$ represents an electron-withdrawing group; $R^{11}$ represents —$R^{11a}$—$R^{12}$ (wherein $R^{11a}$ represents a single bond or a linker; and $R^{12}$ represents a carrier); n represents 0 or 1; and m represents an integer of 1 to 5.

Moreover, the compound represented by formula (1AA) can be synthesized by using a compound represented by formula (5'): $R^9$—$R^{4a}$—$R^9$ (5'), wherein R and $R^9$ are as defined above, as the compound represented by formula (5).

Examples of alkyl groups include, but are not particularly limited to, lower alkyl groups, such as methyl and ethyl. $R^{9a}$ and $R^{9b}$ are both preferably hydrogen atoms.

Examples of electron-withdrawing groups include, but are not particularly limited to, —$NO_2$, —F, $CF_3$, —CN, —COOMe, and the like. The position of the electron-withdrawing group is preferably the para position, for example, in the case of —$NO_2$, and preferably ortho and meta positions, for example, in the case of —F and $CF_3$. In the latter case, more preferably, —CN is at the para position.

When the electron-withdrawing group is, for example, —$NO_2$, m is preferably 1. When the electron-withdrawing group is, for example, —F or $CF_3$, m is preferably 4 to 5, and it is more preferred that all of the ortho and meta positions are substituted with $R^{10}$. In the latter case, even more preferably, —CN is at the para position.

When —F or $CF_3$ (preferably —F) is at all of the ortho and meta positions, and —CN is at the para position, the reaction with the compound represented by formula (5) can sufficiently proceed even under relatively low temperature conditions (preferably 20 to 60° C., more preferably 25 to 40° C.).

The linker is not particularly limited as long as it is capable of linking the carrier to the benzene ring. Examples include linkers containing any of the following partial structures in the main chain.

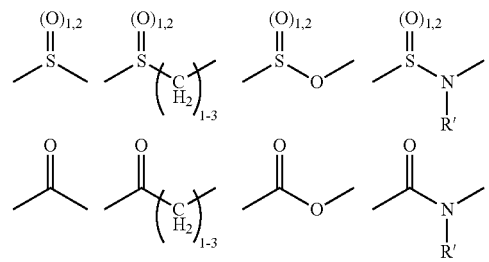

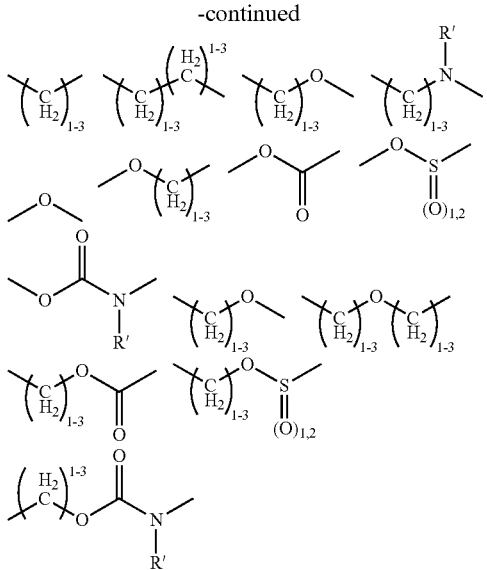

The number of atoms constituting the main chain of the linker is, for example, 1 to 100, 1 to 50, 1 to 20, or 1 to 10.

The carrier is not particularly limited.

The average particle size of the carrier particles is not particularly limited, and is preferably a size that can be easily precipitated in a solution. The average particle size of the carrier particles is, for example, 1 nm to 1 mm, and preferably 10 nm to 100 μm.

The material of the carrier particles is not particularly limited, and examples include particles of metals, such as gold, silver, copper, iron, aluminum, nickel, manganese, titanium, and oxides thereof; particles of resins, such as polystyrene and latex; silica particles; and the like. The shape of the carrier particles is not particularly limited, and is, for example, a sphere, a rectangular parallelepiped, a cube, a triangular pyramid, or a similar shape. The carrier particles may have, on the surface, a substance for making the binding of another substance (e.g., binding substance 2) easier and/or stronger. Examples of the substance include reactive group-containing substances, such as epoxy group-containing substances, amino group-containing substances, carboxy group-containing substances, and azido group-containing substances; substances with affinity for other molecules, such as avidin, protein A, and protein B; and the like. The carrier particles may further contain a labeling substance. Only one type of carrier particles may be used, or two or more types of carrier particles may be used in combination.

The amount of the compound represented by formula (5) used is generally preferably 0.1 to 5 moles, and more preferably 0.3 to 2 moles, per mole of the compound represented by formula (6), in terms of yield and the like.

The solvent to be used is not limited as long as it does not adversely affect the reaction. Examples include water, alcohol-based solvents (e.g., methanol, ethanol, isopropanol, n-butanol, trifluoroethanol, and ethylene glycol), ketone-based solvents (e.g., acetone and methyl ethyl ketone), ether-based solvents (e.g., tetrahydrofuran, dioxane, diethyl ether, dimethoxyethane, and diglyme), ester-based solvents (e.g., methyl acetate and ethyl acetate), aprotic polar solvents (e.g., acetonitrile, N,N-dimethylformamide, and dimethyl sulfoxide), halogenated hydrocarbon-based solvents (e.g., methylene chloride and ethylene chloride), and mixtures thereof. The solvent is preferably a mixture of water and an alcohol-based solvent.

In this reaction, it is preferable to use an acid catalyst in terms of yield and the like. Examples of acid catalysts include, but are not particularly limited to, acetic acid, methanesulfonic acid, p-toluenesulfonic acid, 2-morpholinoethanesulfonic acid (MES), 3-morpholinopropanesulfonic acid (MOPS), 4-(2-hydroxyethyl)-1-piperazineethanesulfonic acid (HEPES), N-tris(hydroxymethyl)methyl-3-aminopropanesulfonic acid (TAPS), and the like. Of these, Good's buffers, such as MES, MOPS, HEPES, and TAPS, are preferred from the viewpoint of further avoiding hindrance to the subsequent protein modification reaction.

The reaction temperature is not particularly limited. The reaction is generally performed under cooling, at room temperature, or under heating. The reaction may be preferably performed at a temperature of about 20 to 100° C. for 10 minutes to 30 hours.

After completion of the reaction, the solvent can be distilled off, and the product can be isolated and purified by chromatography, recrystallization, or other usual methods. The structure of the product can be identified by elemental analysis, MS (ESI-MS) analysis, IR analysis, $^1$H-NMR, $^{13}$C-NMR, etc.

When the compound represented by formula (6) contains a carrier (i.e., when $R^{11}$ is —$R^{11a}$—$R^{12}$), the purification operation can be performed in a simple manner. Specifically, a compound represented by formula (6×), which is a by-product (aniline derivative) produced by the reaction:

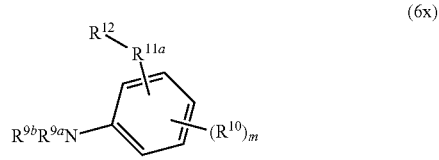

(6x)

wherein $R^{9a}$, $R^{9b}$, $R^{10}$, $R^{11a}$, $R^{12}$, and m are as defined above, can be easily removed by a precipitation operation using the carrier, or the like. Thus, in one embodiment of the present invention, the present invention relates to a compound represented by formula (6'):

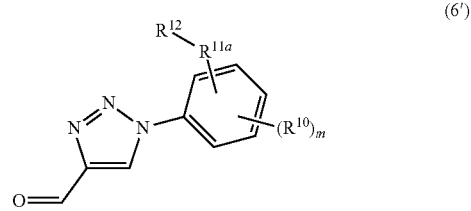

(6')

wherein $R^{10}$, $R^{11}$, $R^{12}$, and m are as defined above.

1-4. Use

The modification molecule of the present invention is useful for linking another molecule/substance to the N-terminus of a protein or peptide, for example, producing the composite substance of the present invention described later (compound represented by formula (7) or a salt thereof, or a hydrate or solvate of the compound or a salt thereof). Thus, the modification molecule of the present invention can be suitably used as a reagent, especially as an active ingredient of a reagent for protein and/or peptide modification. The reagent is not particularly limited as long as it contains the modification molecule of the present invention, and the reagent may further contain other components as necessary. The other components are not particularly limited as long as they are pharmaceutically acceptable. Examples of the other components include bases, carriers, solvents, dispersants, emulsifiers, buffers, stabilizers, excipients, binders, disintegrants, lubricants, thickeners, humectants, colorants, fragrances, chelating agents, and the like.

2. Composite Substance

In one embodiment of the present invention, the present invention relates to a compound represented by formula (7) or a salt thereof, or a hydrate or solvate of the compound or a salt thereof (in the present specification, these may be collectively referral to as "the composite substance of the present invention"):

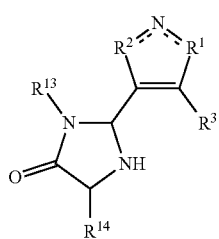

(7)

wherein $R^1$, $R^2$, $R^3$, and $R^4$ are as defined above; $R^{13}$ represents a group in which the N-terminal amino acid residue and —NH— adjacent thereto are excluded from a protein or peptide; and $R^{14}$ represents the side chain of the N-terminal amino acid residue of the protein or peptide. The composite substance of the present invention is described below.

$R^{13}$ represents a group in which the N-terminal amino acid residue and —NH— adjacent thereto are excluded from a protein or peptide.

The protein or peptide is not particularly limited as long as it is a protein or peptide in which the N-terminal amino group is unmodified and the second amino acid residue from the N-terminus is an amino acid residue other than proline. In the protein or peptide, various modifications may be made at sites other than the N-terminus (e.g., cysteine residue). Examples of such a protein or peptide include a protein or peptide represented by formula (7a).

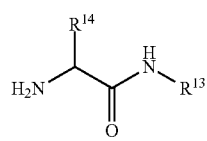

(7a)

$R^{14}$ represents the side chain of the N-terminal amino acid residue of the protein or peptide. The amino acid residue may be a natural amino acid residue or synthetic amino acid residue. Examples include amino acid residues with basic side chains, such as lysine, arginine, and histidine; amino acid residues with acidic side chains, such as aspartic acid and glutamic acid; amino acid residues with uncharged polar side chains, such as glycine, asparagine, glutamine, serine, threonine, tyrosine, and cysteine; amino acid residues with nonpolar side chains, such as alanine, valine, leucine, isoleucine, proline, phenylalanine, methionine, and tryptophan; amino acid residues with (3-branched side chains, such as threonine, valine, and isoleucine; amino acid residues with aromatic side chains, such as tyrosine, phenylalanine, tryptophan, and histidine; and the like.

The protein or peptide is not particularly limited and may be natural, or synthetic or artificial.

The protein or peptide may be chemically modified. The C-terminus of the protein or peptide may be any of a carboxyl group (—COOH), a carboxylate (—COO⁻), an amide (—CONH$_2$), or an ester (—COOR). Here, R in the ester is, for example, a $C_{1-6}$ alkyl group, such as methyl, ethyl, n-propyl, isopropyl, or n-butyl; for example, a $C_{3-8}$ cycloalkyl group, such as cyclopentyl and cyclohexyl; for example, a $C_{6-12}$ aryl group, such as phenyl and α-naphthyl; for example, a phenyl-$C_{1-2}$ alkyl group, such as benzyl and phenethyl; a $C_{7-14}$ aralkyl group including an α-naphthyl-$C_{1-2}$alkyl group, such as α-naphthylmethyl; a pivaloyloxymethyl group; or the like. In the protein or peptide, a carboxyl group (or a carboxylate) other than the C-terminus may be amidated or esterified. As the ester in this case, for example, the above-described C-terminal ester or the like is used. Further, the protein or peptide includes one in which the substituent (e.g., —OH, —SH, an amino group, an imidazole group, an indole group, or a guanidino group) in the side chain of an amino acid in the molecule is protected by an appropriate protecting group (e.g., a $C_{1-6}$ acyl group including $C_{1-6}$ alkanoyl, such as formyl or acetyl).

The protein or peptide may be post-translationally modified, or may be post-translationally modified by an artificial enzymatic treatment or chemical modification. Examples of the post-translational modification include phosphorylation, N-glycosylation, O-glycosylation, C-glycosylation, phosphoglycosylation, glypiation, S-nitrosylation, methylation, N-acetylation, S-myristoylation, S-prenylation, S-palmitoylation, and the like. The protein or peptide may be one to which a protein or peptide such as a known protein tag or signal sequence, or a labeling substance is added. Examples of protein tags include biotin, His tags, FLAG tags, Halo tags, MBP tags, HA tags, Myc tags, V5 tags, PA tags, SPY tags, and the like. Examples of signal sequences include nuclear localization signals and the like.

The protein or peptide may exist as a single molecule alone, or may be linked to another molecule to form a complex. For example, the protein or peptide may be a protein or peptide present on the cell surface, a protein or peptide in a cell disruption liquid, or a protein or peptide supported on some substance. The mode of the linkage is not particularly limited, and examples include hydrogen bonds, electrostatic forces, Van der Waals forces, hydrophobic bonds, covalent bonds, coordinate bonds, and the like.

The protein or peptide may be fragmented by an enzyme or a chemical reaction as long as the N-terminus is present. When the protein or peptide is N-terminally modified, the N-terminus may be de-modified by an enzyme or a chemical reaction.

The compound represented by formula (7) encompasses stereoisomers and optical isomers, and these isomers are not particularly limited.

The salt of the compound represented by formula (7) is not particularly limited. The salt may be an acid salt or a basic salt. Examples of acid salts include inorganic acid salts, such as hydrochloride, hydrobromide, sulfate, nitrate, perchlorate, and phosphate; and organic acid salts, such as acetate, propionate, tartrate, fumarate, maleate, malate, citrate, methanesulfonate, and p-toluenesulfonate. Examples of basic salts include alkali metal salts, such as sodium salts and potassium salts; alkaline earth metal salts, such as calcium salts and magnesium salts; salts with ammonia; salts with organic amines, such as morpholine, piperidine, pyrrolidine, monoalkylamine, dialkylamine, trialkylamine, mono(hydroxyalkyl)amine, di(hydroxyalkyl)amine, and tri(hydroxyalkyl)amine; and the like.

The compound represented by formula (7) can also be a hydrate or a solvate. Examples of solvents include organic solvents (e.g., ethanol, glycerol, and acetic acid), and the like.

The compound represented by formula (7) can be synthesized by various methods. As an example, the compound represented by formula (7) can be produced by a method comprising reacting the protein or peptide with the modification molecule of the present invention. This reaction may be a reaction successive to the synthesis reaction of the modification molecule of the present invention (particularly preferably the reaction of Section "1-2. Synthesis method 2" above). In this case, for example, the reaction mixture obtained in the synthesis reaction of the modification molecule of the present invention can be diluted with a solvent used in this reaction, and then this reaction can be performed.

The amount of the modification molecule of the present invention used is generally preferably 5 to 400 moles, per mole of the protein or peptide, in terms of yield and the like.

This reaction is generally performed in the presence of a reaction solvent. Examples of reaction solvents include, but are not particularly limited to, water and the like. The solvents may be used singly, or in a combination of two or more. Moreover, it is preferable to add a buffer, such as a phosphate buffer, to the solvent. When water is used, the pH of this reaction is preferably near neutral, specifically preferably 6 to 8.5, more preferably 6.5 to 8, and even more preferably 7 to 7.5, in terms of N-terminal selectivity.

In addition to the above components, additives may be suitably used in this reaction as long as the progress of the reaction is not significantly impaired.

The reaction may be performed under heating, at room temperature, or under cooling. The reaction is generally preferably performed at a temperature at which the protein or peptide is not significantly denatured, for example, 0 to 45° C. (in particular 0 to 40° C.). The reaction time is not particularly limited and may be generally 8 to 36 hours, in particular 12 to 24 hours.

The progress of the reaction can be monitored by chromatography or other usual methods. After completion of the reaction, the solvent can be distilled off, and the product can be isolated and purified by chromatography, recrystallization, or other usual methods as necessary. The structure of the product can be identified by elemental analysis, MS (ESI-MS) analysis, IR analysis, $^1$H-NMR, $^{13}$C-NMR, etc.

When the compound represented by formula (1AA) is used as the modification molecule of the present invention, a compound represented by formula (7AA):

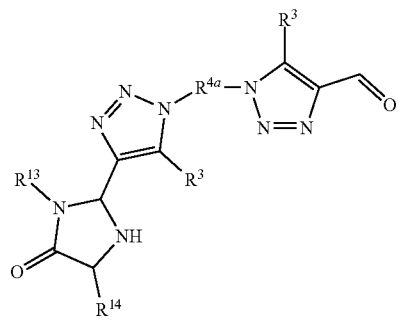

(7AA)

wherein $R^3$, $R^{4a}$, $R^{13}$, and $R^{14}$ are as defined above, is obtained by the above reaction. In this case, an organic molecule or the like can be linked by further oxime formation with hydroxylamine. Specifically, the compound represented by formula (1AA) can be reacted with a compound represented by formula (8): $R^4$—O—NH$_2$(8), wherein $R^4$ is as defined above, to synthesize a compound represented by formula (7AAA):

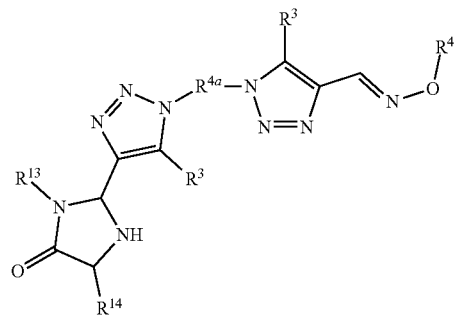

(7AAA)

wherein $R^3$, $R^{4a}$, $R^4$, $R^{13}$, and $R^{14}$ are as defined above. The conditions etc. of this synthetic reaction can be determined in accordance with or based on known reaction conditions for oxime formation with hydroxylamine, starting from an aldehyde. This reaction is also applicable to protein modification because it proceeds even in water under mild conditions.

The composite substance of the present invention has a structure in which another substance is linked to the protein or peptide. In various fields depending on the substance to be linked, the composite substance of the present invention can be used as, for example, an antibody-drug conjugate, a labeled protein reagent, a protein immobilization inorganic material, a fusion protein in which a protein is linked, or a protein having a nucleic acid fused therewith.

In one embodiment of the composite substance of the present invention, the composite substance can be designed so that the substance linked to the protein or peptide dissociates gradually. Thus, after the composite substance of the present invention in which, for example, a drug is linked to the protein or peptide is administered to a living body, the drug can be gradually released in the living body by utilizing gradual dissociation of the drug from the composite substance of the present invention in the living body.

When the composite substance of the present invention has a reactive group (for example, when $R^3$ has a reactive group), the reactive group can be used to further link another substance. It is useful, for example, for linking other substances (e.g., organic molecules, organic molecular complexes, and inorganic materials) by a reaction using an azido group (e.g., a Huisgen cycloaddition reaction, a strain-promoted azide-alkyne cycloaddition reaction, or a Staudinger-Bertozzi ligation).

EXAMPLES

Examples are given below to illustrate the present invention in more detail; however, the present invention is not limited to these Examples.

Example 1. Compound Synthesis 1 (Method A)

1-1. Equipment Used

Nuclear magnetic resonance (NMR) spectra were measured using a Bruker AVANCE IR HD nuclear magnetic resonance spectrometer, and chemical shifts were calculated using the remaining signal of the measurement solvent as an internal reference. Electrospray ionization time-of-flight mass spectrometry (ESI-TOF MS) was performed using a Bruker micrOTOF focus IR mass spectrometer, and methanol or acetonitrile (both HPLC grade) was used as the mobile phase. Fourier transform infrared absorption (FT-IR) spectra were measured using a Jasco FT/IR-4000 Fourier transform infrared spectrophotometer in ATR mode, using a diamond or gallium prism.

1-2. Reagent, Solvent, Etc.

As the reagents and solvents used in the synthesis, commercially available products were used as is. The azide compounds used, which are precursors, were synthesized with reference to a published report (Y. Zhao, P. Gong, Bioorg. Med. Chem., 2014, 22, 6438-6452).

1-3-1. Synthesis of 1-(3-Carboxyphenyl)-1H-1,2,3-Triazole-4-Carbaldehyde (1)

Compound 1 was synthesized according to the following scheme.

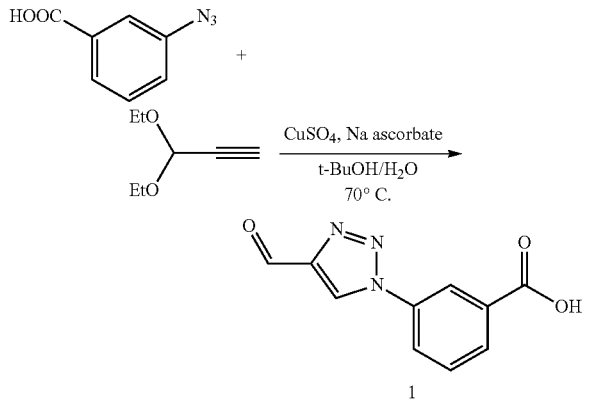

Compound 1 was synthesized with reference to published reports (T. A. Bakka, M. B. Strom, J. H. Anderson, O. R. Gautun, Bioorg. Med. Chem. Lett., 2017, 27, 1119-1123, and J. T. Fletcher, J. A. Cristensen, E. M. Villra, Tetrahedron Lett., 2017, 58, 4450-4454). The specific synthesis procedure and results of compound identification are described below.

An azide compound (0.60 mmol), propargylaldehyde diethyl acetal (115 μL, 0.80 mmol), and sodium ascorbate (60 mg, 0.30 mmol) were added to a mixture of an aqueous solution (7.5 mL) of copper (II) sulfate pentahydrate (38 mg, 0.15 mmol) and t-butyl alcohol (7.5 mL) under a nitrogen atmosphere, and the mixture was stirred at 70° C. for 24 hours and at room temperature for 1 hour in air. The resulting suspension was diluted with a saturated sodium chloride aqueous solution (10 mL), subjected to extraction with ethyl acetate (50 mL×3), and washed with a saturated sodium chloride aqueous solution (20 mL×2). The resulting organic layer was dried over sodium sulfate, and the solvents of the filtrate obtained by filtration were distilled off under reduced pressure. The residue was purified by silica gel column chromatography to give compound 1 (yellow solid). FIG. 1 shows the $^1$H NMR spectrum.

Yield 48%; $^1$H NMR (400 MHz, DMSO-$d_6$): δ10.12 (s, 1H), 9.67 (s, 1H), 8.48 (s, 1H), 8.16; (d, J=7.8 Hz, 1H), 8.09 (d, J=7.8 Hz, 1H), 7.72 (t, J=7.8 Hz, 1H); $^{13}$C NMR (100 MHz, DMSO-$d_6$): δ184.9, 167.0, 147.6, 136.0, 130.1, 130.0, 126.6, 124.0, 121.3; ESI-TOF MS (positive mode) m/z calcd. for $C_{10}H_7NaN_3O_3$ [M+Na]$^+$ 240.04, found 240.04; FT-IR (ATR mode, Ge prism), ν cm$^{-1}$: 3128, 2923, 1697, 1263, 1230, 1184, 757, 673, 647.

1-3-2. Synthesis of 1-(4-Carboxyphenyl)-1H-1,2,3-Triazole-4-Carbaldehyde (2)

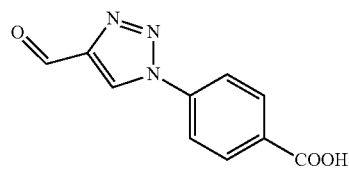

Figure 2:
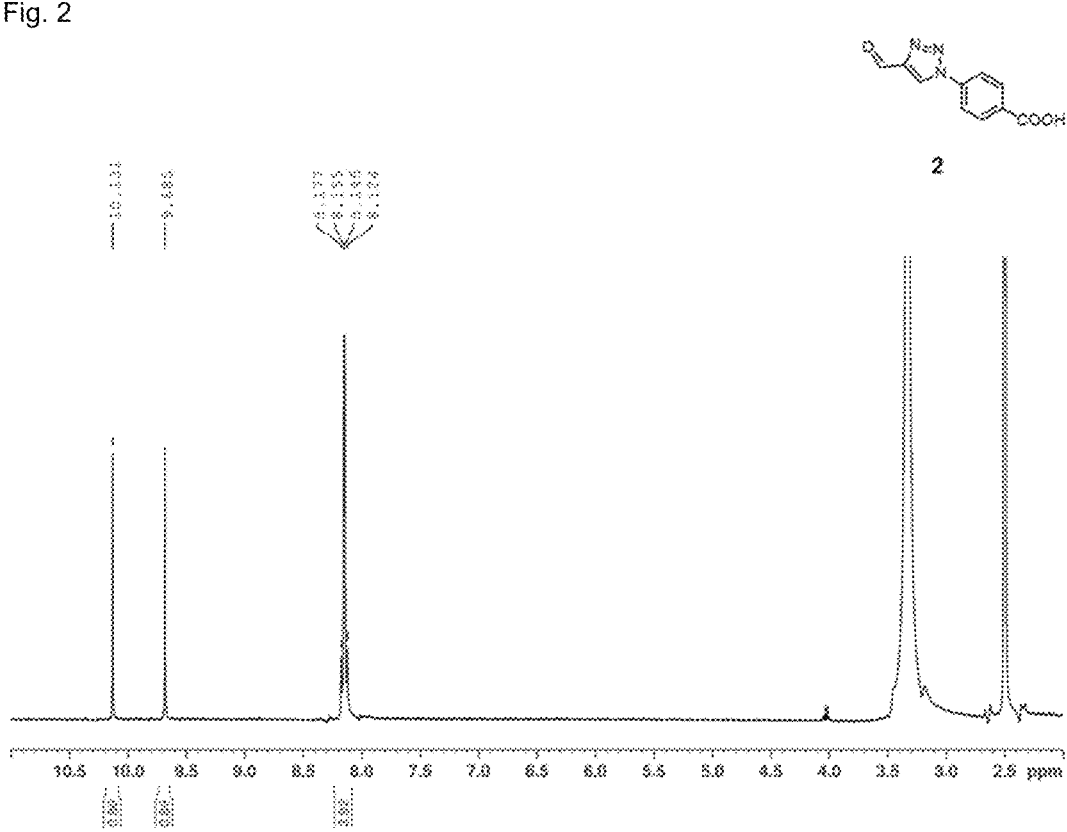
FIG. 2 shows the $^1$H NMR spectrum (400 MHz, DMSO-$d_6$) of compound 2.

Compound 2 (yellow solid) was synthesized using 4-azidobenzoic acid as a precursor by using Method A as in Example 1-3-1. FIG. 2 shows the $^1$H NMR spectrum.

Yield 63%; $^1$H NMR (400 MHz, DMSO-$d_6$): δ10.13 (s, 1H), 9.69 (s, 1H), 8.18-8.12 (m, 4H); ESI-TOF MS (positive mode) m/z calcd. for $C_{10}H_7NaN_3O_3$ [M+Na]$^+$ 240.04, found 240.04; FT-IR (ATR mode, Ge prism), ν cm$^{-1}$: 3110, 1695, 1683, 1605, 1429, 1319, 1294, 1264, 989, 945, 864, 773, 702, 688.

1-3-3. Synthesis of 1-(3,5-Dicarboxyphenyl)-1H-1,2,3-Triazole-4-Carbaldehyde (3)

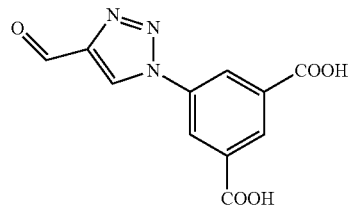

Figure 3:
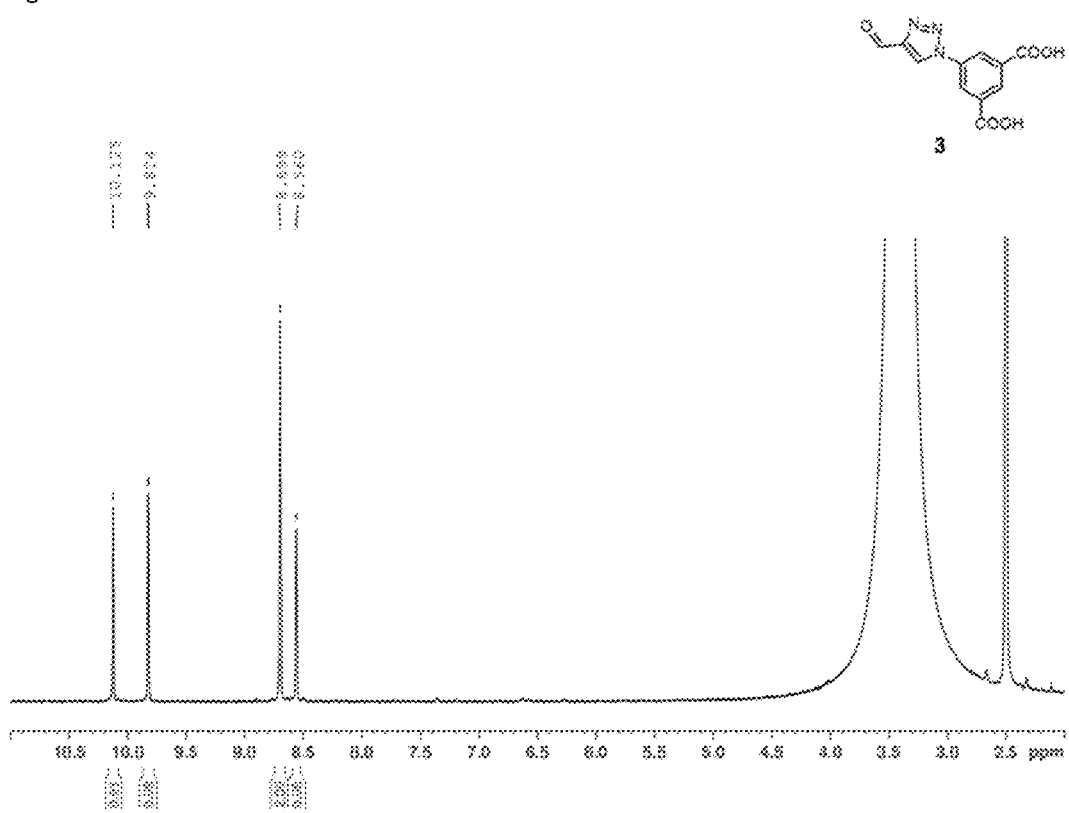
FIG. 3 shows the $^1$H NMR spectrum (400 MHz, DMSO-$d_6$) of compound 3.

Compound 3 (yellow solid) was synthesized using 5-azidoisophthalic acid as a precursor by using Method A as in Example 1-3-1. FIG. 3 shows the $^1$H NMR spectrum.
Yield 10%; $^1$H NMR (400 MHz, DMSO-d$_6$): δ10.12 (s, 1H), 9.81 (s, 1H), 8.65 (s, 2H), 8.56 (s, 1H); FT-IR (ATR mode, Ge prism), v cm$^{-1}$: 3133, 1697, 1296, 1281, 1247, 1049, 830, 757, 678, 666, 566, 527.

1-3-4. Synthesis of 1-(4-(Diethylamino)Phenyl)-1H-1,2,3-Triazole-4-Carbaldehyde (4)

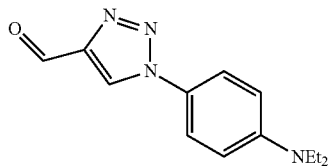

4

Figure 4:
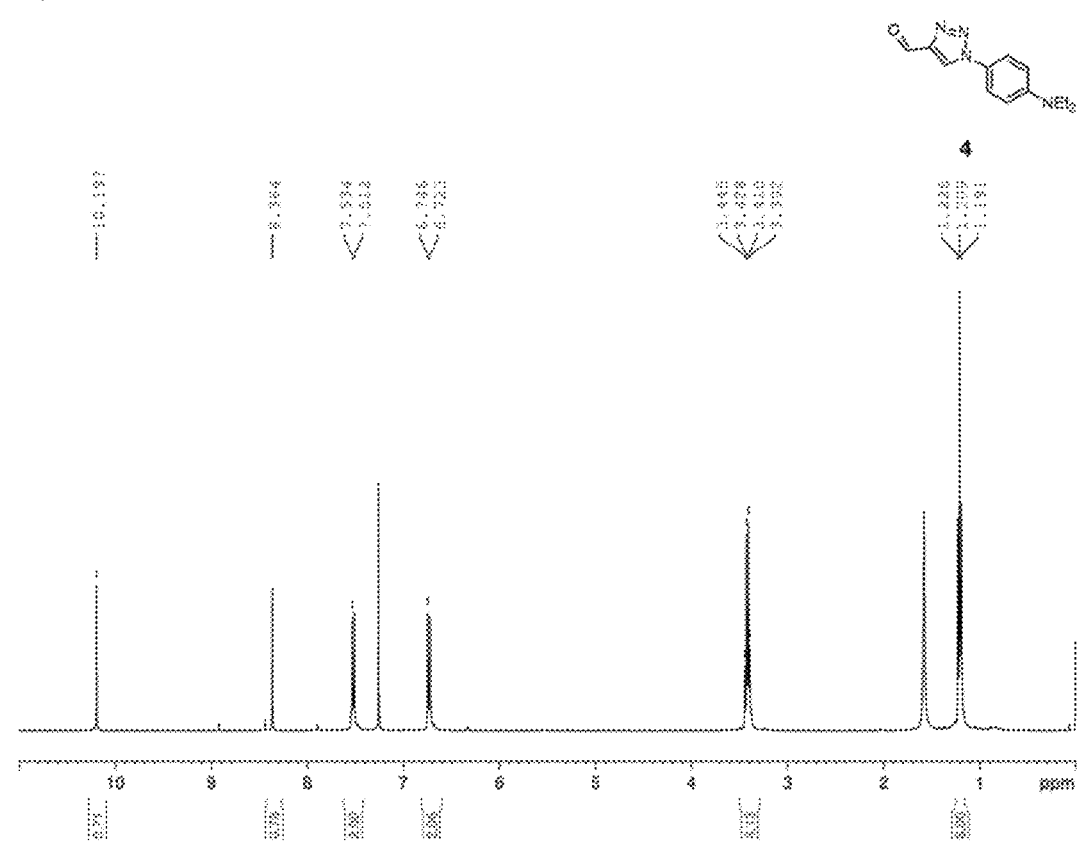
FIG. 4 shows the $^1$H NMR spectrum (400 MHz, CDCl$_3$) of compound 4.

Compound 4 (brown solid) was synthesized using 4-azido-N,N-diethylaniline as a precursor by using Method A as in Example 1-3-1. FIG. 4 shows the $^1$H NMR spectrum.
Yield 60%; $^1$H NMR (400 MHz, CDCl$_3$): δ10.12 (s, 1H), 8.36 (s, 1H), 7.52 (d, J=9.1 Hz, 2H), 6.73 (d, J=9.1 Hz, 2H), 3.42 (q, J=7.1 Hz, 4H), 1.21 (t, J=7.1 Hz, 6H); $^{13}$C NMR (100 MHz, DMSO-d$_6$): δ185.0, 148.0, 147.3, 125.1, 124.3, 122.1, 111.4, 43.8, 12.3; ESI-TOF MS (positive mode) m/z calcd. for C$_{13}$H$_{16}$NaN$_4$O [M+Na]$^+$ 267.12, found 267.12.

1-3-5. Synthesis of 1-(4-Methoxyphenyl)-1H-1,2,3-Triazole-4-Carbaldehyde (5)

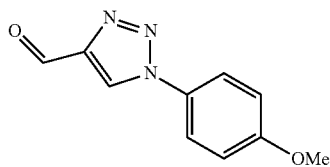

5

Figure 5:
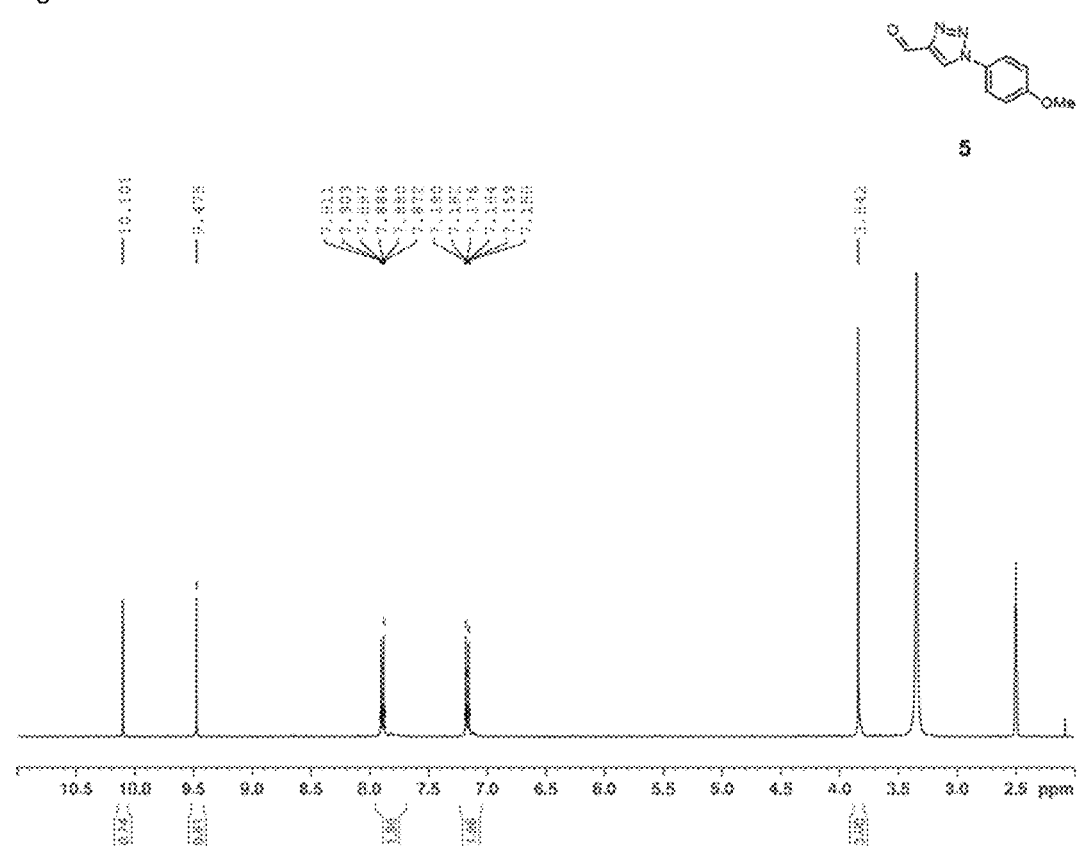
FIG. 5 shows the $^1$H NMR spectrum (400 MHz, DMSO-$d_6$) of compound 5.

Compound 5 (white solid) was synthesized using 1-azido-4-methoxybenzene as a precursor by using Method A as in Example 1-3-1. FIG. 5 shows the $^1$H NMR spectrum.
Yield 68%; $^1$H NMR (400 MHz, DMSO-d$_6$): δ10.12 (s, 1H), 8.43 (s, 1H), 7.66 (d, J=8.9 Hz, 2H), 7.06 (d, J=8.9 Hz, 2H), 3.89 (s, 3H); $^{13}$C NMR (100 MHz, DMSO-d$_6$): δ185.0, 159.9, 147.5, 129.3, 125.9, 122.4, 115.0, 55.7; ESI-TOF MS (positive mode) m/z calcd. for C$_{10}$H$_9$NaN$_3$O$_2$[M+Na]$^+$ 226.06, found 226.06.

1-3-6. Synthesis of 1-Phenyl-1H-1,2,3-Triazole-4-Carbaldehyde (6)

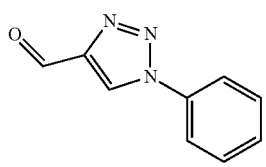

6

Figure 6:
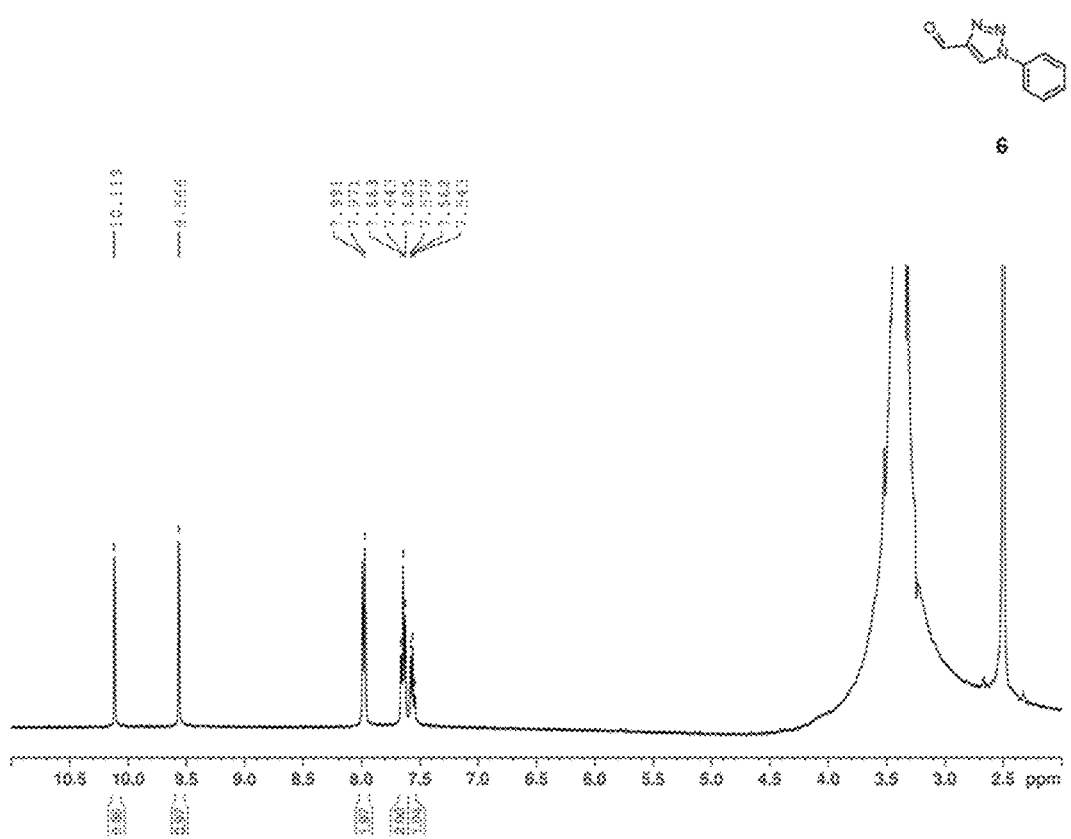
FIG. 6 shows the $^1$H NMR spectrum (400 MHz, DMSO-$d_6$) of compound 6.
Figure 7:
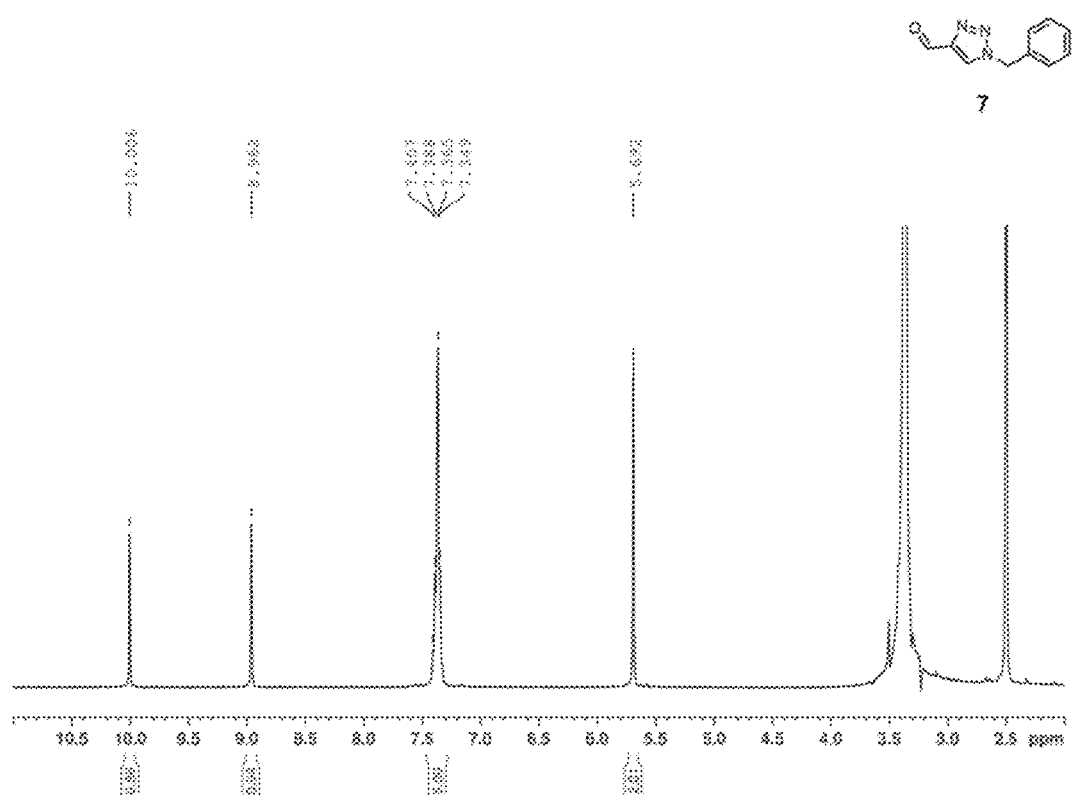
FIG. 7 shows the $^1$H NMR spectrum (400 MHz, DMSO-$d_6$) of compound 7.

Compound 6 (brown solid) was synthesized using azidobenzene as a precursor by using Method A as in Example 1-3-1. FIG. 6 shows the $^1$H NMR spectrum.
Yield 9%; $^1$H NMR (400 MHz, DMSO-d$_6$): δ10.11 (s, 1H), 9.57 (s, 1H), 7.97 (d, J=8.0 Hz, 2H), 7.66-7.54 (m, 3H).

Example 2. Compound Synthesis 2 (Method B)

The equipment, reagents, solvents, etc. used were similar to those in Example 1.

2-1. Synthesis of 1-Benzyl-1H-1,2,3-Triazole-4-Carbaldehyde (7)

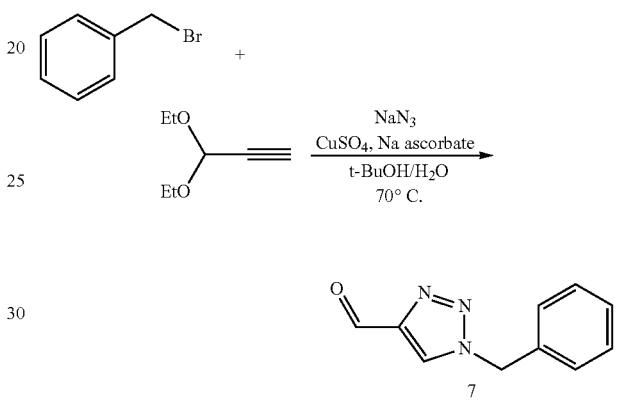

7

Compound 7 was synthesized with reference to a published report (J. T. Fletcher, Tetrahedron Lett., 2017, 58, 4450-4454). The specific synthesis procedure and results of compound identification are described below.

A mixture of an aqueous solution (7.5 mL) of copper (II) sulfate pentahydrate (47.8 mg, 0.19 mmol) and t-butyl alcohol (7.5 mL) was cooled to 0° C., and sodium azide (103 mg, 1.6 mmol) was added under a nitrogen atmosphere. After stirring at room temperature for 10 minutes, benzyl bromide (179 μL, 1.5 mmol) and propargylaldehyde diethyl acetal (240 μL, 1.7 mmol) were added to the mixture, and the mixture was stirred at 70° C. for 24 hours and at room temperature for 1 hour in air. The reaction solution was air-cooled to room temperature, and then diluted with a saturated sodium chloride aqueous solution (5 mL), followed by extraction with ethyl acetate (30 mL×3). The resulting organic layer was dried over magnesium sulfate. The filtrate obtained by filtering off solid was distilled off under reduced pressure to obtain a crude product, and the crude product was purified by silica gel column chromatography (hexane:ethyl acetate=2:1) to give compound 7 (white solid). Table 7 shows the $^1$H NMR spectrum.

Yield 46%; $^1$H NMR (400 MHz, DMSO-d$_6$): δ10.00 (s, 1H), 8.95 (s, 1H), 7.41-7.32 (m, 5H), 5.69 (s, 2H); $^{13}$C NMR (100 MHz, DMSO-d$_6$): δ185.0, 147.0, 135.3, 128.9, 128.4, 128.3, 128.1, 53.2; ESI-TOF MS (positive mode) m/z calcd. for C$_{10}$H$_9$NaN$_3$O [M+na]$^+$ found 210.06; FT-IR (ATR mode, Ge prism), vcm$^{-1}$: 1694, 1535, 1237, 1165, 1052, 877, 796, 767, 714, 701, 565, 556, 543, 532, 515, 505.

2-2. Synthesis of 1-(Naphthalen-2-Ylmethyl)-1H-1,2,3-Triazole-4-Carbaldehyde (8)

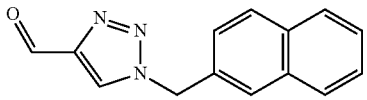

8

Figure 8:
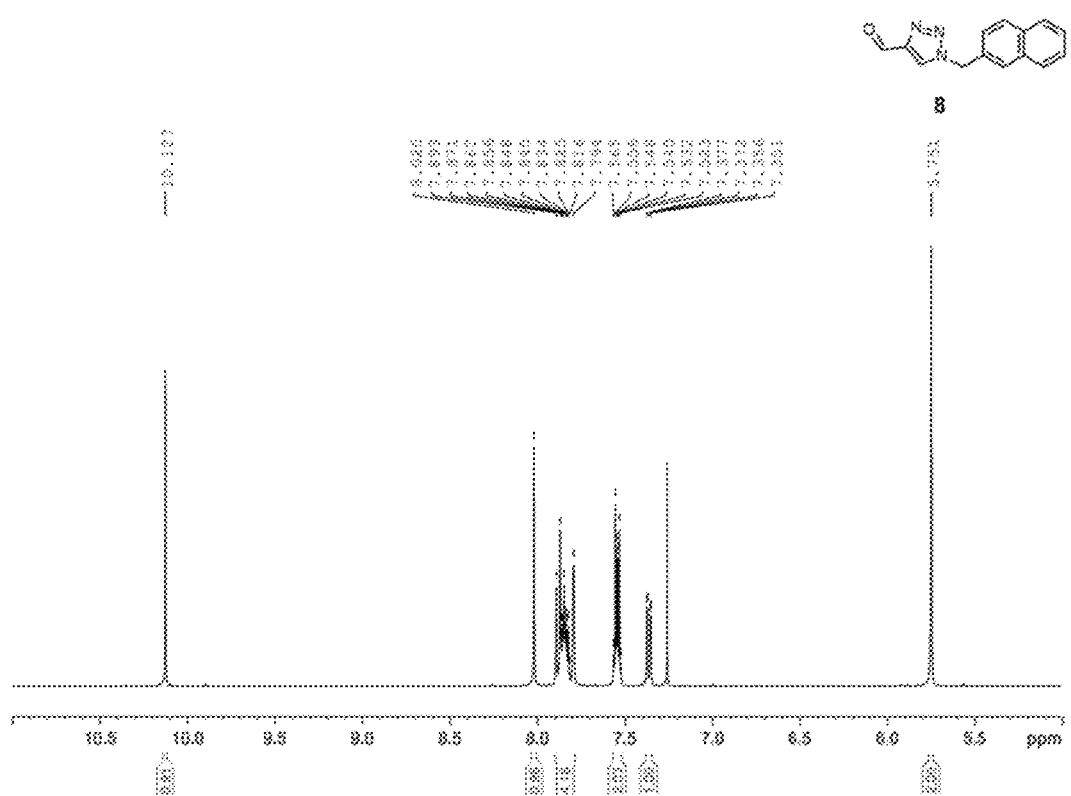
FIG. 8 shows the $^1$H NMR spectrum (400 MHz, CDCl$_3$) of compound 8.

Compound 8 (white solid) was synthesized using 2-(bromomethyl)naphthalene as a precursor by using Method B as in Example 2-1. FIG. 8 shows the $^1$H NMR spectrum.
Yield 20%; $^1$H-NMR (400 MHz, CDCl$_3$): δ10.13 (s, 1H), 8.02 (s, 1H), 7.90-7.80 (m, 4H), 7.57-7.53 (m, 2H), 7.38-7.35 (m, 1H) 5.75 (s, 2H); ESI-TOF MS (positive mode) m/z calcd. for C$_{14}$H$_{11}$NaN$_3$O [M+Na]$^+$ 260.08, found 260.08; FT-IR (ATR mode, Ge prism), νcm$^{-1}$: 3121, 1709, 1538, 1239, 1177, 1052, 1026, 866, 835, 792, 761, 563, 553, 527, 511.

Example 3. Compound Synthesis 3 (Method C)

The equipment, reagents, solvents, etc. used were similar to those in Example 1.

3-1. Synthesis of 1-(p-Tolyl)-1H-1,2,3-Triazole-4-Carbaldehyde (9)

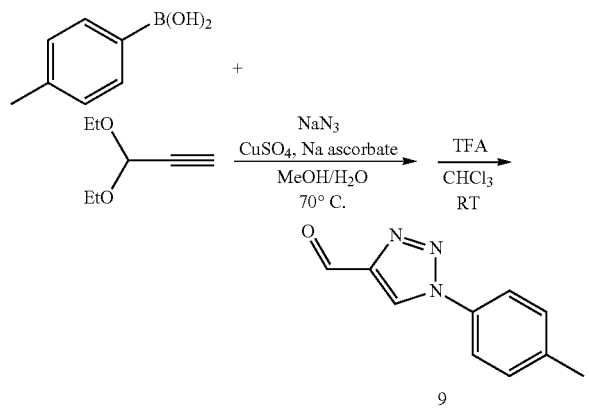

9

Compound 9 was synthesized with reference to a published report (C.-Z. Tao, X. Cui, J. Li, A-X. Liu, L. Liu, Q.-X. Guo, Tetrahedron Lett., 2007, 48, 3525-3529). The specific synthesis procedure and results of compound identification are described below.

Figure 9:
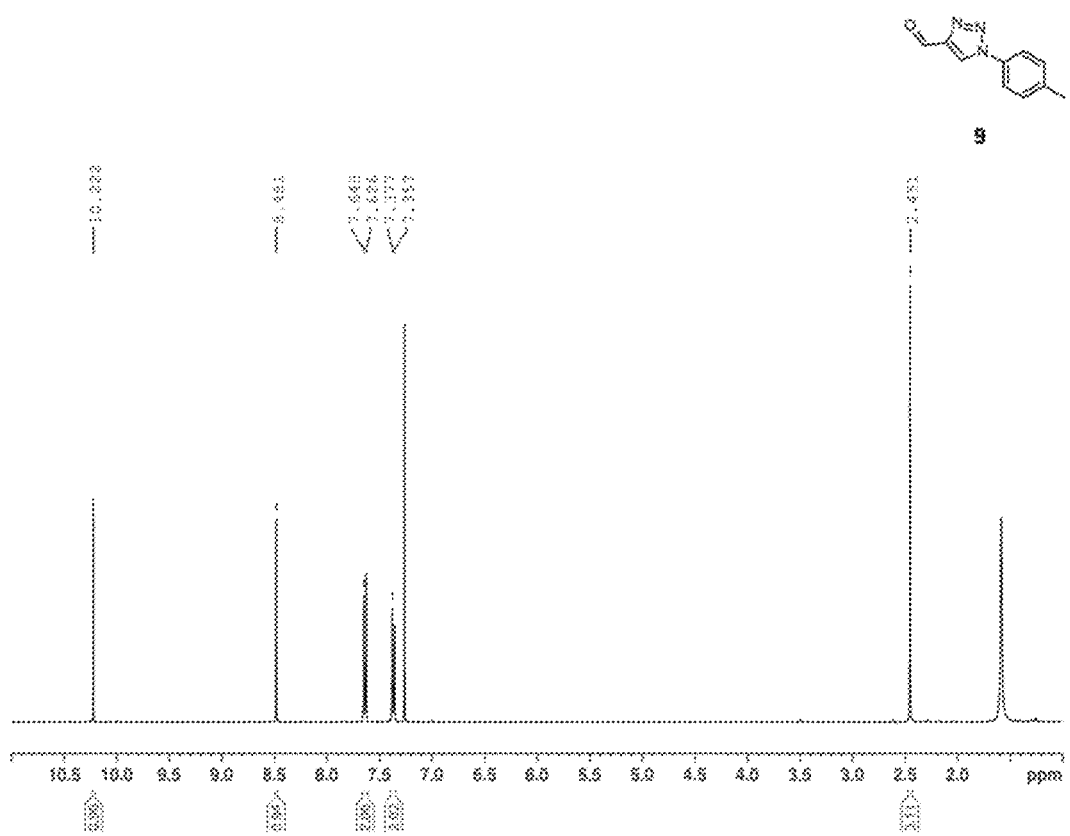
FIG. 9 shows the $^1$H NMR spectrum (400 MHz, DMSO-$d_6$) of compound 9.

Pure water (5 mL) containing copper (II) sulfate pentahydrate (47.8 mg, 0.19 mmol) was added to a methanol solution (5 mL) containing 4-methylphenylboronic acid (136 mg, 1.0 mmol) and sodium azide (98 mg, 1.5 mmol), and the mixture was stirred under air for 5 hours. Subsequently, sodium ascorbate (79 mg, 0.4 mmol) and propargylaldehyde diethyl acetal (286 μL, 1.7 mmol) were added under a nitrogen atmosphere, and the mixture was stirred at 70° C. for 24 hours and at room temperature for 1 hour in air. The reaction solution was air-cooled to room temperature and then diluted with a saturated sodium chloride aqueous solution (40 mL), followed by extraction with ethyl acetate (50 mL×3). The resulting organic layer was dried over magnesium sulfate. The filtrate obtained by filtering off solid was distilled off under reduced pressure to obtain a crude product, and the crude product was dissolved in chloroform (3 mL). Pure water (3 mL) and trifluoroacetic acid (3 mL) were added, followed by vigorous stirring at room temperature. The mixture was diluted with a saturated sodium chloride aqueous solution (30 mL), and the organic layer was extracted with chloroform (30 mL×3). The resulting organic layer was dried over magnesium sulfate. The filtrate obtained by filtering off solid was distilled off under reduced pressure to obtain a crude product, and the crude product was purified by reprecipitation (hexane:chloroform) to give compound 9 (white solid). FIG. 9 shows the $^1$H NMR spectrum.
Yield 71%; $^1$H NMR (400 MHz, CDCl$_3$): δ10.2 (s, 1H), 8.48 (s, 1H), 7.64 (d, J=8.3 Hz, 2H), 7.37 (d, J=8.3 Hz, 2H), 2.45 (s, 3H); $^{13}$C NMR (100 MHz, CDCl$_3$): δ185.3, 148.2, 140.3, 134.0, 130.7, 123.2, 120.9, 21.3; ESI-TOF MS (positive mode) m/z calcd. for C$_{10}$H$_9$N$_3$ONa [M+Na]$^+$ 210.06, found 210.06.

Example 4. Compound Synthesis 4 (Method D)

The equipment, reagents, solvents, etc. used were similar to those in Example 1. 4-1. Synthesis of 1-(4-nitrophenyl)-1H-1,2,3-triazole-4-carbaldehyde (10)

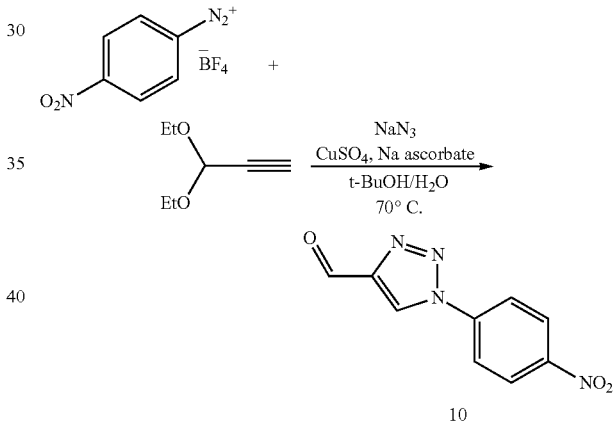

10

Compound 10 was synthesized with reference to a published report (J. T. Fletcher, J. E. Reilly, Tetrahedron Lett., 2011, 52, 5512-5515). The specific synthesis procedure and results of compound identification are described below.

Figure 10:
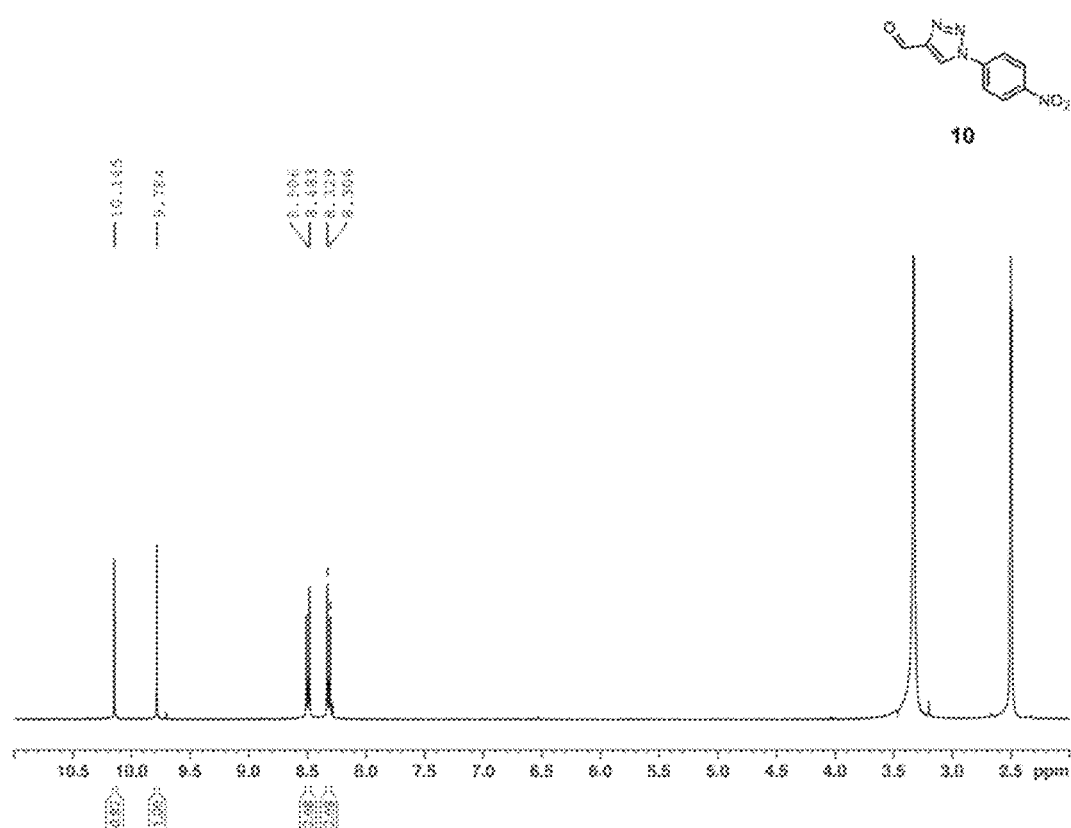
FIG. 10 shows the $^1$H NMR spectrum (400 MHz, DMSO-$d_6$) of compound 10.

A mixture of an aqueous solution (25 mL) of sodium azide (358 mg, 5.5 mmol) and t-butyl alcohol (25 mL) was cooled to 0° C., and nitrobenzenediazonium tetrafluoroborate (1.18 g, 5.0 mmol) was added portionwise, followed by vigorous stirring for 1 hour. Subsequently, propargylaldehyde diethyl acetal (783 μL, 5.5 mmol) and sodium ascorbate (396 mg, 2 mmol) were added under a nitrogen atmosphere, followed by stirring at 70° C. overnight. The reaction solution was filtered, followed by extraction of the filtrate with ethyl acetate (50 mL×3). The organic layer was dried over sodium sulfate, and the solvents were distilled off under reduced pressure. The resulting crude product was purified by reprecipitation (hexane:ethyl acetate) to give compound 10 (yellow solid). FIG. 10 shows the $^1$H NMR spectrum.
Yield 62%; $^1$H NMR (400 MHz, DMSO-d$_6$): δ10.15 (s, 1H), 9.78 (s, 1H), 8.49 (d, J=9.2 Hz, 2H), 8.32 (d, J=9.2 Hz, 2H); $^{13}$C NMR (100 MHz, DMSO-d$_6$): δ185.0, 147.8, 147.4, 140.3, 126.9, 125.6, 121.5; ESI-TOF MS (positive mode) m/z calcd. for $C_9H_6N_4O_3Na$ [M+Na]$^+$ 241.03, found 241.03.

Example 5. Compound Synthesis 5 (Method E)

The equipment, reagents, solvents, etc. used were similar to those in Example 1.

5-1. Synthesis of 5-methyl-1-phenyl-1H-1,2,3-triazole-4-carbaldehyde (13)

Compound 13 was synthesized according to the following scheme with reference to published reports (J. Zhang, G. Jin, S. Xiao, J. Wu, S. Guo, Tetrahedron 2013, 69, 2352-2356; I. Ibnusaud, B. Singaram, J. Org. Chem., 2018, 83, 1431-1440; and T. Ismail, S Shafi, I. Hyder, T. Sidiq, A. Khajuria, S. M. Alam, M. S. K. Halmuthur, Arch. Pharm. Chem. Life Sci., 2015, 348, 796-807).

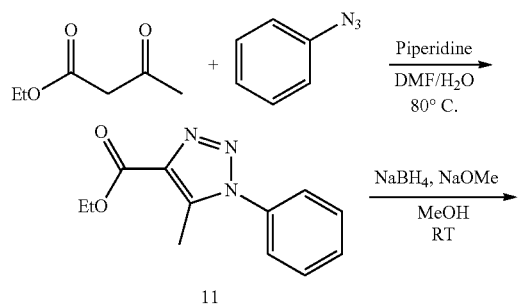

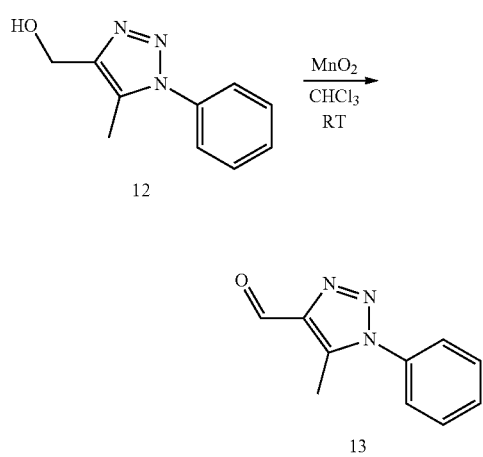

5-1-1. Synthesis of Ethyl 5-Methyl-1-Phenyl-1H-1,2,3-Triazole-4-Carboxylate (11)

Ethyl acetoacetate (1.5 mmol) and piperidine (20 μL, 0.2 mmol) were added to a solution of phenyl azide (120 mg, 1.0 mmol) in a mixture of dimethylformamide (10 mL) and pure water (1 mL), and the mixture was stirred at 80° C. for 24 hours. Water (20 mL) was added to the resulting solution to stop the reaction, followed by extraction with diethyl ether (20 mL×5). The resulting organic layer was washed with water (20 mL×2). The organic layer was dried over sodium sulfate, and the solvents of the filtrate obtained by filtration were distilled off under reduced pressure. The resulting crude product was purified by silica gel column chromatography (hexane:ethyl acetate) to give compound 11 (white solid).

Yield 27%; $^1$H NMR (400 MHz, CDCl$_3$): δ7.61-7.55 (m, 3H), 7.47-7.44 (m, 2H), 4.47 (q, J=7.1 Hz, 2H), 2.60 (s, 3H), 1.46 (t, J=7.1 Hz, 3H).

5-1-2. Synthesis of (5-Methyl-1-Phenyl-1H-1,2,3-Triazol-4-Yl)Methanol (12)

Figure 11:
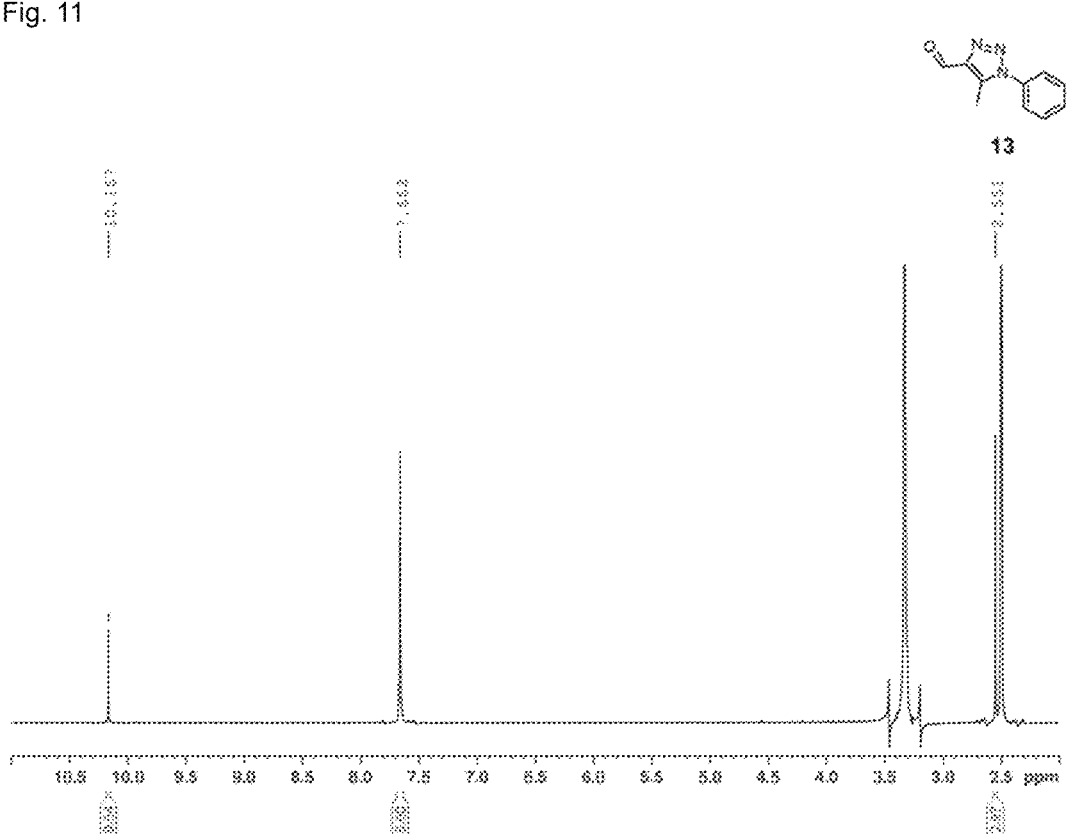
FIG. 11 shows the $^1$H NMR spectrum (400 MHz, DMSO-$d_6$) of compound 13.

Sodium borohydride (29 mg, 0.77 mmol) was added to a solution of compound 11 (0.12 mmol) and sodium methoxide (1 mg, 2 μmol) in methanol (1 mL) under a nitrogen atmosphere, followed by stirring at room temperature for 3 hours. Excess methanol was added to the reaction solution to stop the reaction. The reaction solution was concentrated under reduced pressure, and the residue was diluted with a saturated sodium chloride aqueous solution (5 mL), followed by extraction with diethyl ether (20 mL×3) and washing with a saturated sodium chloride aqueous solution (5 mL×2). The resulting organic layer was dried over sodium sulfate. Thereafter, filtration was performed, and the crude product obtained by concentrating the solvent of the filtrate under reduced pressure was purified by silica gel column chromatography (hexane:ethyl acetate=2:1) to give compound 12 (white solid). FIG. 11 shows the $^1$H NMR spectrum.

Yield 37%; $^1$H NMR (400 MHz, CDCl$_3$): δ7.58-7.52 (m, 3H), 7.48-7.46 (m, 2H), 4.83 (d, J=6.0 Hz, 2H), 2.37 (s, 2H), 1.96 (t, J=6.0 Hz, 1H).

5-1-3. Synthesis of 5-Methyl-1-Phenyl-1H-1,2,3-Triazole-4-Carbaldehyde (13)

Activated manganese dioxide (141 mg, 1.6 mmol) was added to a solution of compound 12 (0.16 mmol) in chloroform (5 mL), and the mixture was stirred under a nitrogen atmosphere at room temperature for 24 hours. The reaction mixture was filtered, and the solvent of the resulting filtrate was distilled off under reduced pressure to give compound 13 (white solid).

Yield 89%; $^1$H NMR (400 MHz, DMSO-d$_6$): δ7.58-7.52 (m, 3H), 7.48-7.46 (m, 2H), 4.83 (d, J=6.0 Hz, 2H), 2.37 (s, 2H), 1.96 (t, J=6.0 Hz, 1H); $^{13}$C NMR (100 MHz, DMSO-d$_6$): δ186.1, 143.3, 138.7, 134.7, 130.3, 129.8, 125.3, 9.3.

5-1-4. Synthesis of Ethyl 1-Phenyl-5-(Trifluoromethyl)-1H-1,2,3-Triazole-4-Carboxylate (14)

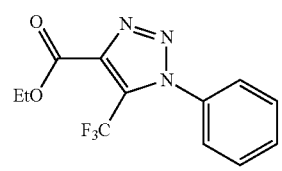

Compound 14 (yellow oil) was synthesized using ethyl 4,4,4-trifluoroacetoacetate as a precursor by the same method as in Example 5-1-1.

Yield 35%; $^1$H NMR (400 MHz, CDCl$_3$): δ7.63-7.57 (m, 3H), 7.47 (d, J=7.3 Hz, 2H), 4.51 (q, J=7.1, Hz, 2H), 1.45 (t, J=7.1 Hz, 3H).

5-1-5. Synthesis of (1-Phenyl-5-(Trifluoromethyl)-1H-1,2,3-Triazol-4-Yl)Methanol (15)

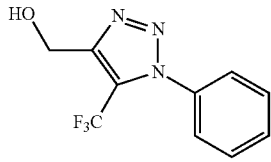

15

Compound 15 (white solid) was synthesized using compound 14 as a precursor by the same method as in Example 5-1-2.

Yield 83%; $^1$H NMR (400 MHz, CDCl$_3$): 87.61-7.55 (m, 3H), 7.47 (d, J=7.2 Hz, 2H), 4.96 (d, J=6.0 Hz, 2H).

5-1-6. Synthesis of (1-Phenyl-5-(Trifluoromethyl)-1H-1,2,3-Triazol-4-Yl)Methanol (16)

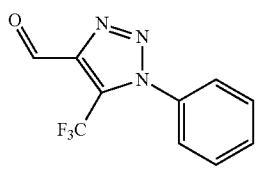

16

Figure 12:
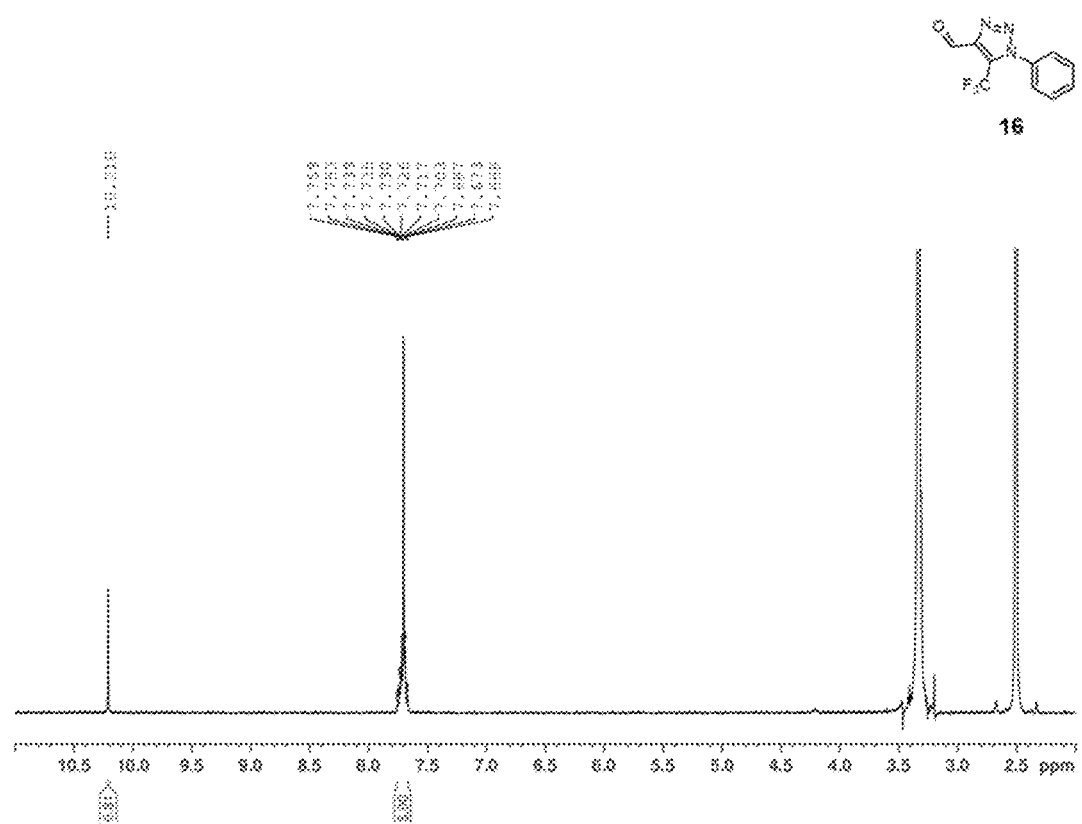
FIG. 12 shows the $^1$H NMR spectrum (400 MHz, DMSO-$d_6$) of compound 16.

Compound 16 (white solid) was synthesized using compound 15 as a precursor by the same method as in Example 5-1-3. FIG. 12 shows the $^1$H NMR spectrum.

Yield 75%; $^1$H NMR (400 MHz, DMSO-d$_6$): δ10.21 (s, 1H), 7.74-7.66 (m, 5H).

Example 6. Compound Synthesis 6 (Method F)

The equipment, reagents, solvents, etc. used were similar to those in Example 1.

6-1. Synthesis of 1-(2-(2-(Prop-2-Yn-1-Yloxy)Ethoxy)Ethyl)-1H-1,2,3-Triazole-4-Carbaldehyde (17)

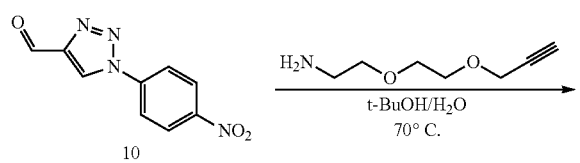

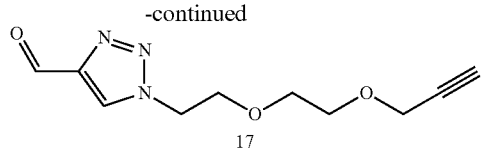

17

Figure 13:
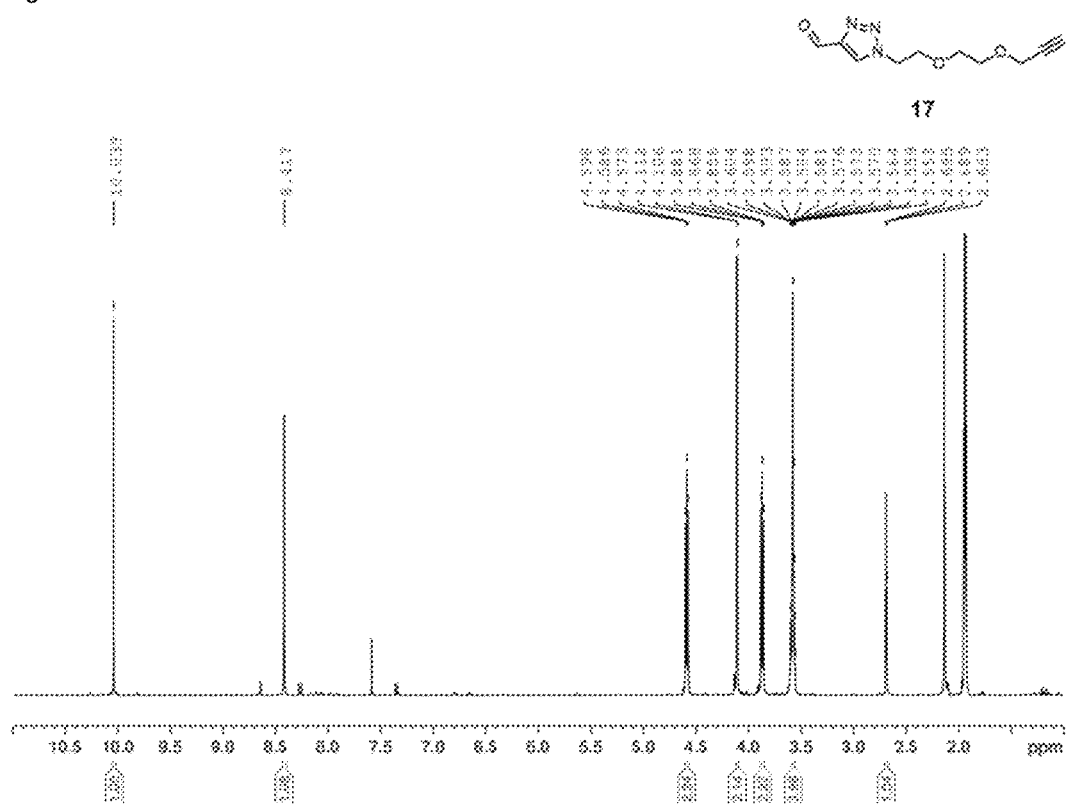
FIG. 13 shows the $^1$H NMR spectrum (400 MHz, CD$_3$CN) of compound 17.

Compound 10 (109 mg, 0.5 mmol) and 2-(2-(2-propynyloxy)ethoxy)ethylamine (72 μL, 0.5 mmol) were dispersed in a mixture of pure water (1 mL) and t-butyl alcohol (1 mL), and the mixture was stirred at 60° C. overnight under a nitrogen atmosphere. After the reaction solution was cooled to 0° C., 0.1 M HCl aq. (50 mL) was added to stop the reaction, followed by extraction with ethyl acetate (20 mL×3). The organic layer was dried over sodium sulfate, and the solvents were distilled off under reduced pressure. The resulting crude product was purified by silica gel column chromatography (hexane:ethyl acetate=0 to 60%) to give compound 17 (yellow oil). FIG. 13 shows $^1$H NMR spectrum.

Yield 70%; $^1$H NMR (400 MHz, CD$_3$CN): δ10.04 (s, 1H), 8.42 (s, 1H), 4.59 (t, J=5.1 Hz, 2H), 4.11 (d, J=2.4 Hz, 2H), 3.87 (t, J=5.1 Hz, 2H), 3.60-3.56 (m, 4H), 2.69 (t, J=2.4 Hz, 1H); $^{13}$C NMR (100 MHz, CD$_3$CN): δ185.7, 148.4, 128.6, 80.8, 75.7, 70.6, 69.7, 69.5, 58.7, 51.3; ESI-TOF MS (positive mode) m/z calcd. for C$_{10}$H$_{13}$N$_3$O$_3$Na [M+Na]$^+$ 246.08, found 246.08.

Example 7. Compound Synthesis 7: Synthesis of Functional Molecule

The equipment, reagents, solvents, etc. used were similar to those in Example 1. The reaction precursors used were purchased or suitably synthesized.

7-1. Synthesis of N-(2-(2-(2-(2-(4-Formyl-1H-1,2,3-Triazol-1-Yl)Ethoxy)Ethoxy)Ethoxy)Ethyl)-5-4S)-2-oxohexahydro-1H-thieno[3,4-d]imiclazol-4-yl)pentanamide (18)

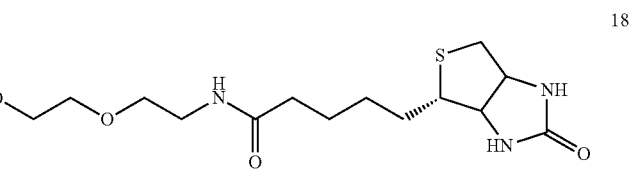

18

Figure 14:
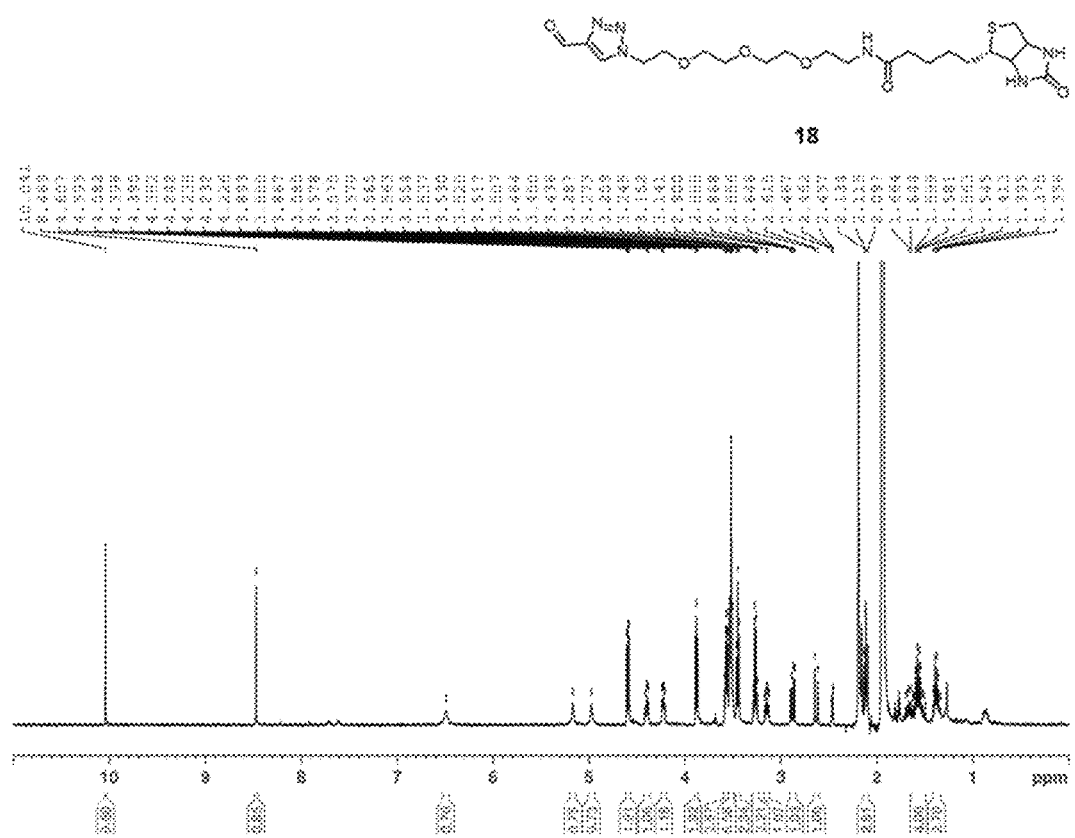
FIG. 14 shows the $^1$H NMR spectrum (400 MHz, CD$_3$CN) of compound 18.

Compound 18 (white solid) was synthesized using N-(2-(2-(2-(2-azidoethoxy)ethoxy)ethoxy)ethyl)-5-4S)-2-oxo-hexahydro-1H-thieno[3,4-d]imidazol-4-yl)pentanamide as a precursor by using the same method (Method A) as in Example 1-3-1. FIG. 14 shows the $^1$H NMR spectrum.

Yield 23%; $^1$H NMR (400 MHz, CD$_3$CN+DMSO-d$_6$ (one drop)): δ10.0 (s, 1H), 8.47 (s, 1H), 6.49 (s, 1H), 5.17 (s, 1H), 4.98; (s, 1H), 4.60 (t, J=5.0 Hz, 2H), 4.42-4.38 (m, 1H), 4.24-4.21 (m, 1H), 3.88 (t, J=5.0 Hz, 2H), 3.59-3.55 (m, 2H), 3.54 (m, 6H), 3.45 (t, J=5.6 Hz, 2H), 3.27 (t, J=5.6 Hz, 2H), 3.17-3.12 (m, 1H), 2.88 (dd, J=5.0, 12.6 Hz, 1H), 2.63 (d, J=5.0, 12.6 Hz, 1H), 2.12 (t, J=7.3 Hz, 2H), 1.63-1.49 (m, 4H), 1.41-1.34 (m, 2H); ESI-TOF MS (positive mode) m/z calcd. for C$_{21}$H$_{34}$N$_6$O$_6$Na [M+Na]$^+$ 521.1, found 521.1.

7-2. Synthesis of 1-(3',6'-Dihydroxy-3-Oxo-3H-Spiro[Isobenzofuran-1,9'-Xanthen]-5-Yl)-1H-1,2,3-Triazole-4-Carbaldehyde (19)

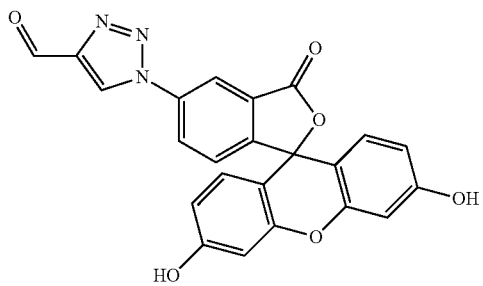

Figure 15:
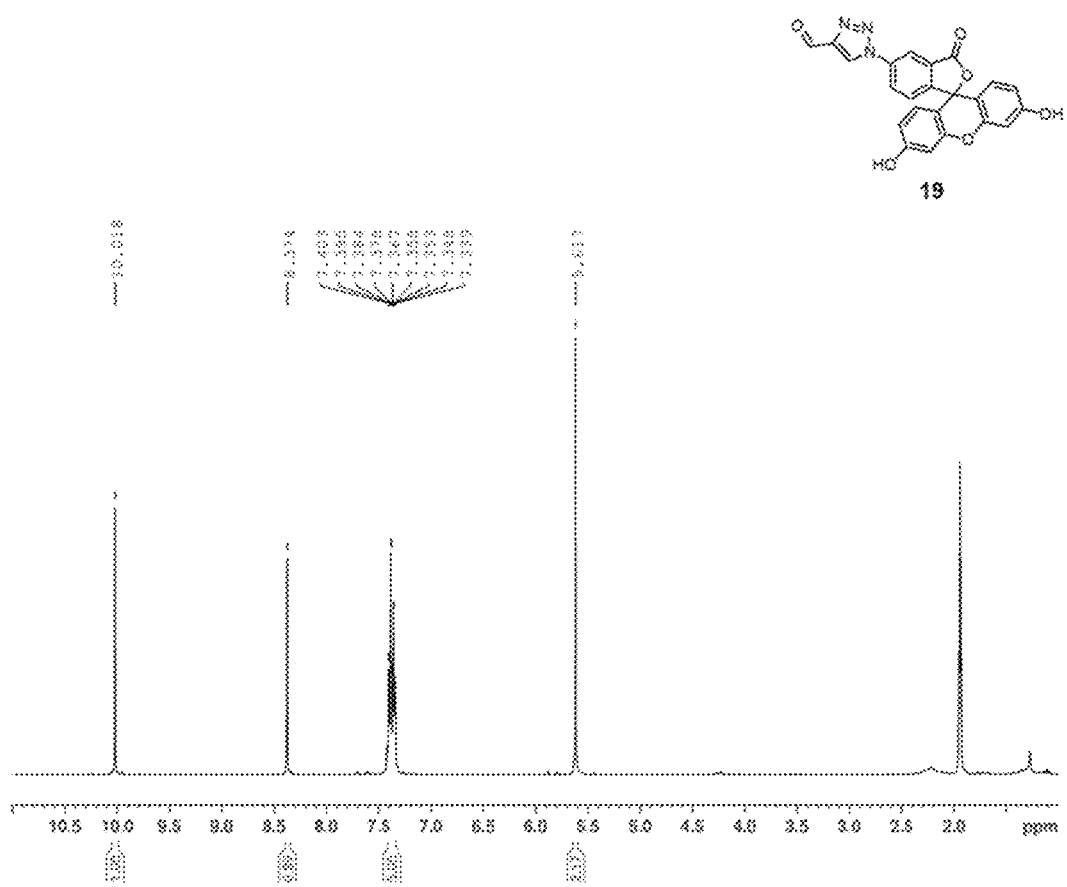
FIG. 15 shows the $^1$H NMR spectrum (400 MHz, CD$_3$CN) of compound 19.

Compound 19 (orange solid) was synthesized using 5-azido-3',6'-dihydroxy-3H-spiro[isobenzofuran-1,9'-xanthen]-3-one as a precursor by using the same method (Method A) as in Example 1-3-1. FIG. 15 shows the $^1$H NMR spectrum.

Yield 47%; $^1$H NMR (400 MHz, DMSO-d$_6$): δ10.19 (s, 2H), 10.15 (s, 1H), 9.80 (s, 1H), 8.60 (d, J=1.7 Hz, 1H), 8.43 (dd, J=2.0, 8.3 Hz, 1H), 7.57 (d, J=8.3 Hz, 1H), 6.71-6.67 (m, 4H), 6.57 (dd, J=2.2, 8.7 Hz, 2H); $^{13}$C NMR (100 MHz, CDCl$_3$): δ185.0, 167.5, 159.7, 152.6, 151.9, 147.7, 137.4, 129.2, 128.0, 127.9, 126.8, 126.0, 116.7, 112.7, 108.9, 102.3, 83.6; ESI-TOF MS (positive mode) m/z calcd. for C$_{23}$H$_{14}$N$_3$O$_6$ [M+H]$^+$ 428.09, found 428.10.

7-3. Synthesis of Polyethylene Glycol-Tethered Triazole-4-Carbaldehyde (MW.~4 kDa) (20)

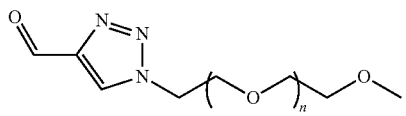

Figure 16:
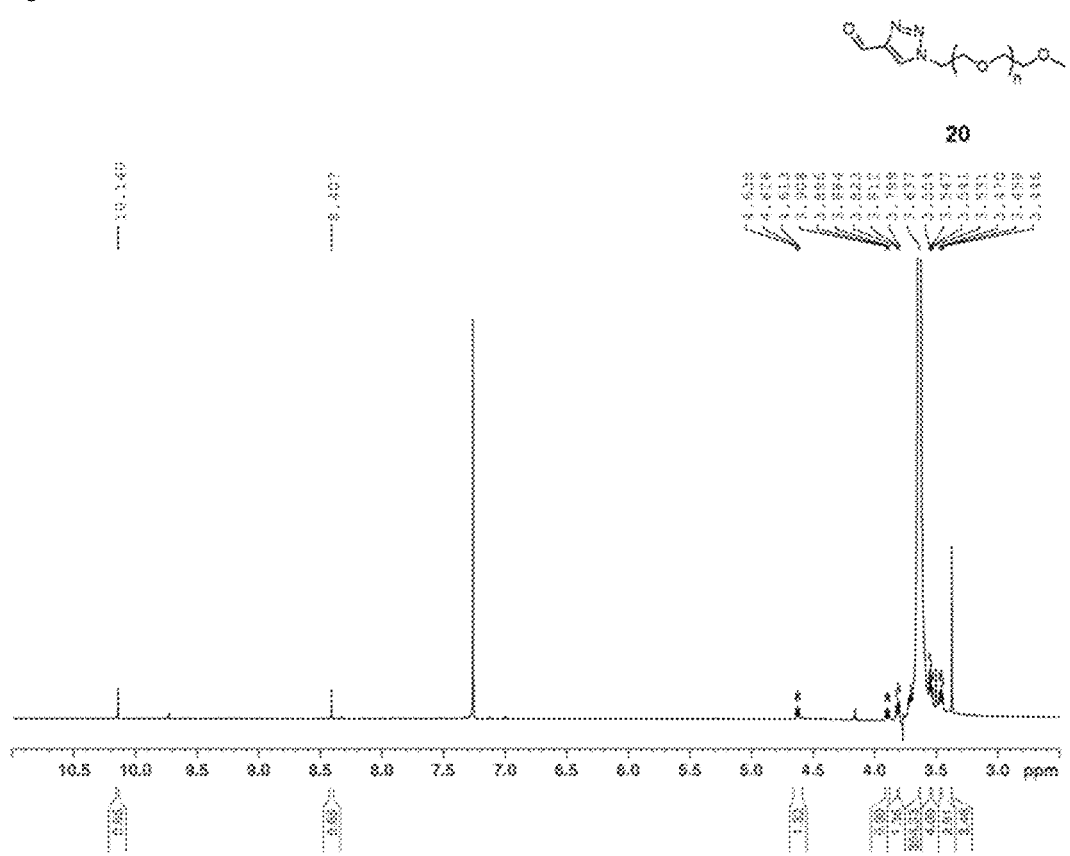
FIG. 16 shows the $^1$H NMR spectrum (400 MHz, CD$_3$Cl) of compound 20.

Compound 20 (brown solid) was synthesized using polyethylene glycol monomethyl ether (produced by Tokyo Chemical Industry Co., Ltd.) having a molecular weight of about 4 kDa as a starting material by using the same method as in Example 1-3-1, with reference with a published report (M. B. van Eldijk, F. C. M. Smit, N. Vermue, M. E Debets, S. Schoffelen, J. C. M. van Hest, Biomacromolecules, 2014, 15, 2751-2759). Purification was performed by reprecipitation with diethyl ether. FIG. 16 shows the $^1$H NMR spectrum.

Yield 50%; $^1$H NMR (400 MHz, CDCl$_3$): δ10.14 (s, 1H), 8.41 (s, 1H), 4.63 (t, J=4.8 Hz, 1H), 3.91-3.45 (m, 366H).

7-4. Synthesis of 1-(2-(2-(2-(2-Azidoethoxy)Ethoxy)Ethoxy)Ethyl)-1H-1,2,3-Triazole-4-Carbaldehyde (21)

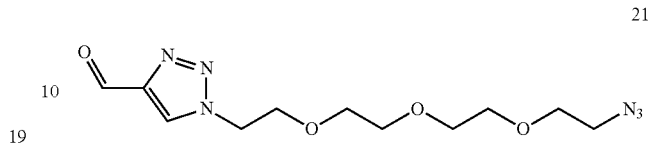

Figure 17:
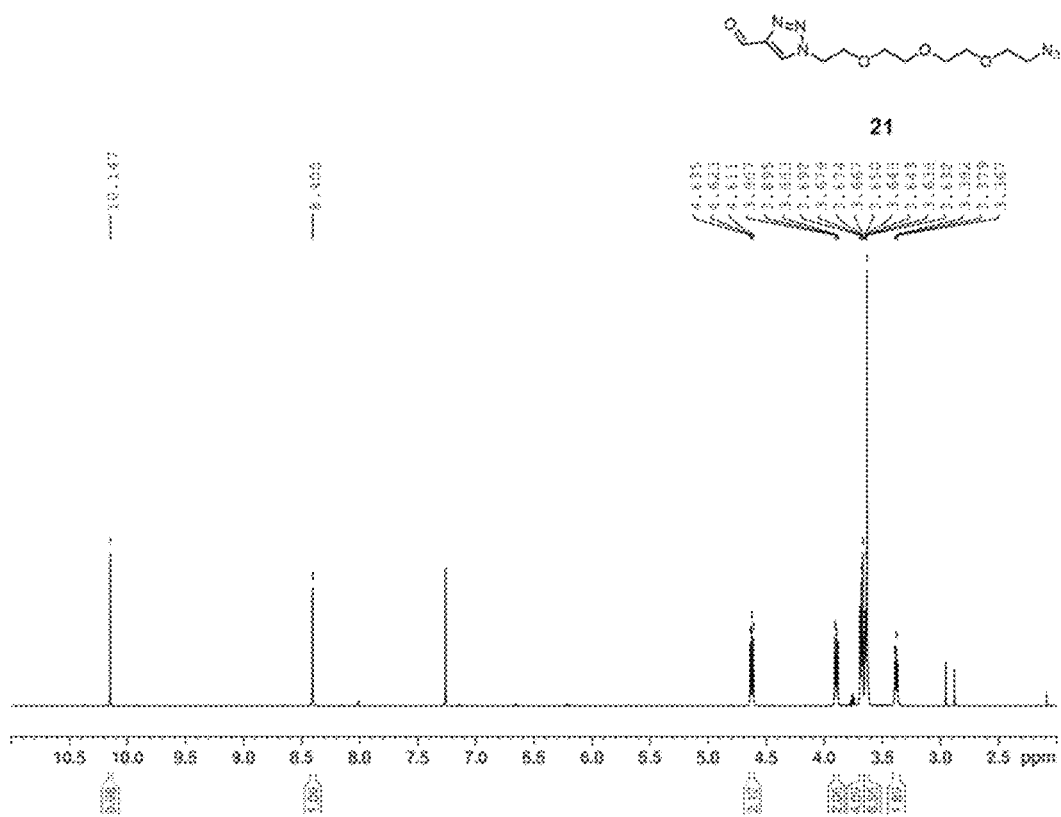
FIG. 17 shows the $^1$H NMR spectrum (400 MHz, CD$_3$Cl) of compound 21.

Compound 21 (yellow oil) was synthesized using 1-azido-2-(2-(2-(2-azidoethoxy)ethoxy)ethoxy)ethane as a precursor by using the same method (Method A) as in Example 1-3-1. FIG. 17 shows the $^1$H NMR spectrum.

Yield 27%; $^1$H NMR (400 MHz, CDCl$_3$): δ10.1 (s, 1H), 8.41 (s, 1H), 4.62 (t, J=4.8 Hz, 2H), 3.90; (t, J=4.8 Hz, 2H), 3.68 (m, 4H), 3.65-3.63 (m, 6H), 3.38 (t, J=5.0 Hz, 2H); $^{13}$C NMR (100 MHz, CDCl$_3$): δ185.4, 148.0, 126.9, 70.7 (two signal were merged), 70.7 (two signals were merged), 70.2, 69.0, 50.8, 50.7; ESI-TOF MS (positive mode) m/z calcd. for C$_{11}$H$_{18}$N$_6$O$_4$Na [M+Na]$^+$ 321.1, found 321.1.

7-5. Synthesis of Compound 22

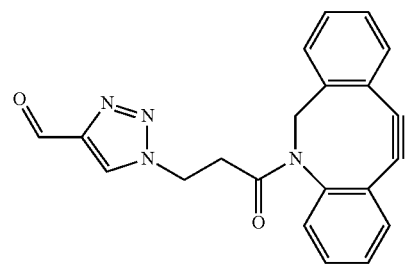

Figure 18:
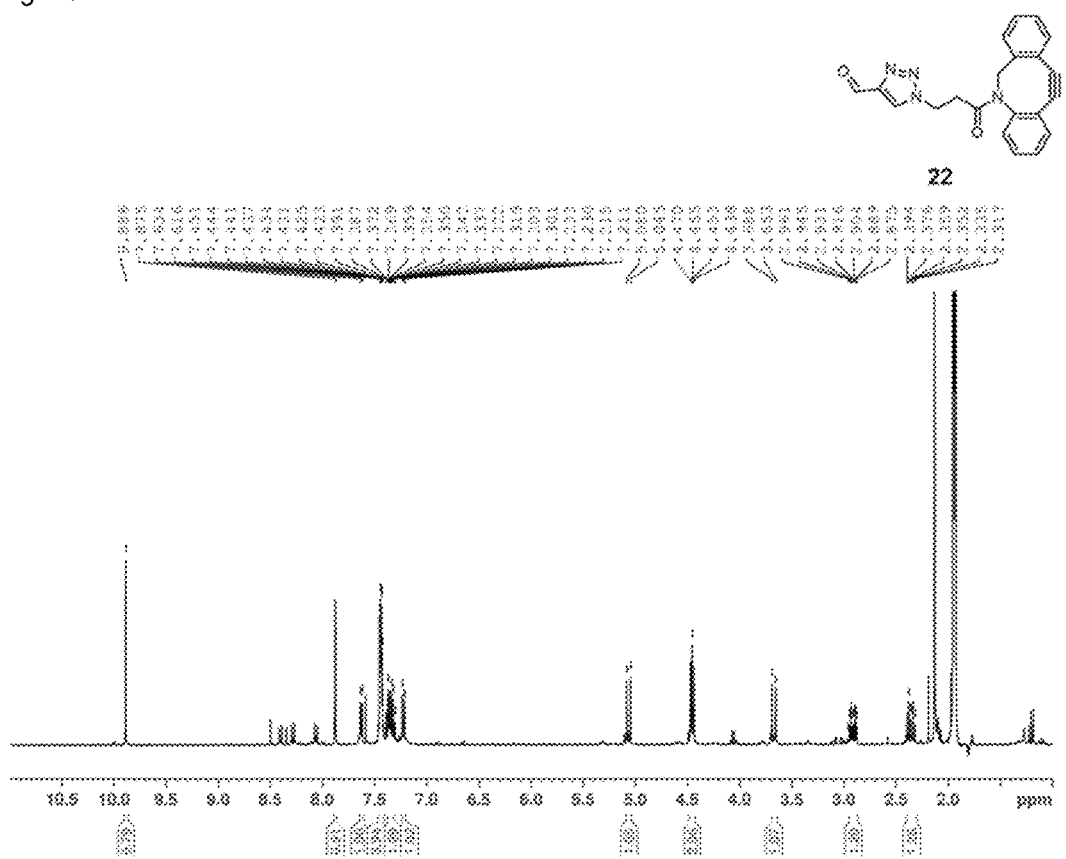
FIG. 18 shows the $^1$H NMR spectrum (400 MHz, CD$_3$CN) of compound 22.

Compound 22 (yellow solid) was synthesized using N-(3-aminopropionyl)-5,6-dihydro-11,12-didehydrodibenz[b,f]azocine as a precursor by using the same method (Method F) as in Example 6. FIG. 18 shows the $^1$H NMR spectrum.

Yield 75%; $^1$H NMR (400 MHz, CD$_3$CN): δ9.89 (s, 1H), 7.88 (s, 1H), 7.62 (d, J=7.2 Hz, 1H), 7.45-7.43 (m, 4H), 7.39-7.32 (m, 2H), 7.22 (dd, J=1.4, 7.4 Hz, 1H), 5.06 (d, J=14 Hz, 1H), 4.45 (m, 2H), 3.66 (d, J=14 Hz, 1H), 2.90 (td, J=6.0, 17 Hz, 1H), 2.35 (td, J=6.0, 17 Hz, 1H); ESI-TOF MS (positive mode) m/z calcd. for C$_{11}$H$_{18}$N$_6$O$_4$Na [M+Na]$^+$ 321.1, found 321.1.

Example 8. Peptide N-Terminal Modification 1

8-1. Reagent, Solvent, Etc.

Ultrapure water used was obtained by purification with Millipore Integral 3. As other reagents and solvents, commercially available products were used as is.

8-2. Peptide N-Terminal Modification

This method targets the N-terminus of a peptide. The peptide that can be a target is one in which the N-terminal amino group is unmodified and the second amino acid residue from the N-terminus is an amino acid other than proline. As a specific example, the N-terminal modification of angiotensin I is described below.

The following shows the amino acid sequence of angiotensin I.

```
                                              (SEQ ID NO: 1)
DRVYIHPFHL
```

The N-terminal modification of the peptide was performed with reference to a published report (J. I. MacDonald, H. K. Munch, T. Moore, M. B. Francis, Nat. Chem. Biol. 2015, 11, 326-331). The specific experimental procedure is described below.

Figure 19:
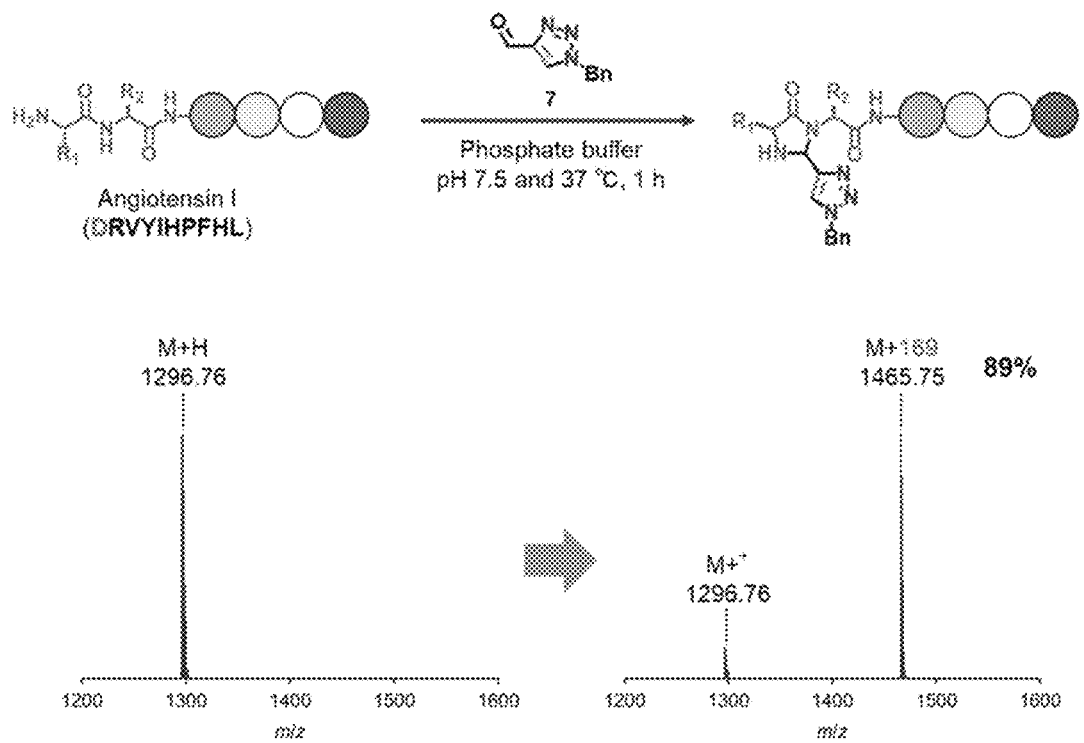
FIG. 19 shows the reaction scheme and results of an N-terminal modification reaction of angiotensin I (Example 8).

A solution of compound 7 in dimethyl sulfoxide (DMSO) (200 mM, 1 µL, 0.2 final concentration: 10 mM) was diluted with a potassium phosphate buffer (10 mM, pH 7.5, 17 µL). An aqueous peptide solution (1 mM, 2 µL, 2 nmol, final concentration: 100 µM) was added thereto, and the mixture was shaken at 37° C. for 4 hours. The modification percentage (=modified peptide/(total peptide amount)) was evaluated from the peak intensity in a mass spectrum by using LC/MS. FIG. 19 shows the results. The modification percentage under this reaction condition was calculated as 89%. The above results confirmed that the compounds according to the present invention serve as protein-modifying agents.

Example 9. Peptide N-Terminal Modification 2

The reagents, equipment, solvents, etc. used were similar to those of Example 8. As compound 24, a compound synthesized according to a published report (H. Hagiwara, S. Okada, Chem. Commun., 2016, 52, 815-818) was used.

9-1. Peptide N-Terminal Modification

The structural analysis of the product in this modification reaction was performed using a model peptide as a substrate. As a specific example, the reaction shown in the following scheme was performed.

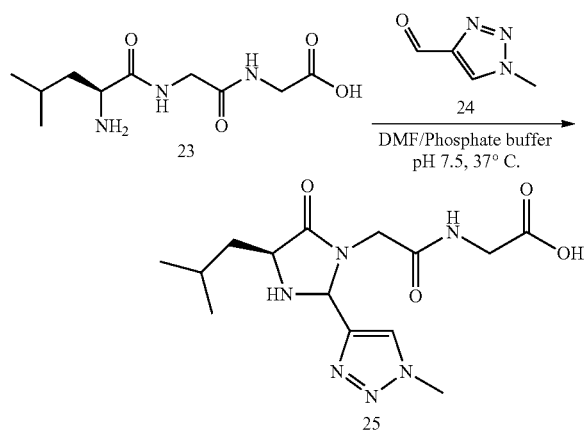

A solution (200 µL) of compound 24 (44 mg, 0.4 mmol) in dimethylformamide (DMF) was added to compound 23 (11 mg, 0.04 mmol) in a potassium phosphate buffer (10 mM, pH 7.5, 1.8 mL), and the mixture was shaken at 37° C. for 16 hours. The solvent was distilled off under reduced pressure. The resulting crude product was purified by silica gel column chromatography (ethyl acetate:acetonitrile:water=95:5:0 to 0:95:5) to give compound 25.

9-2. $^1$H NMR Analysis of Compound 25

Figure 20:
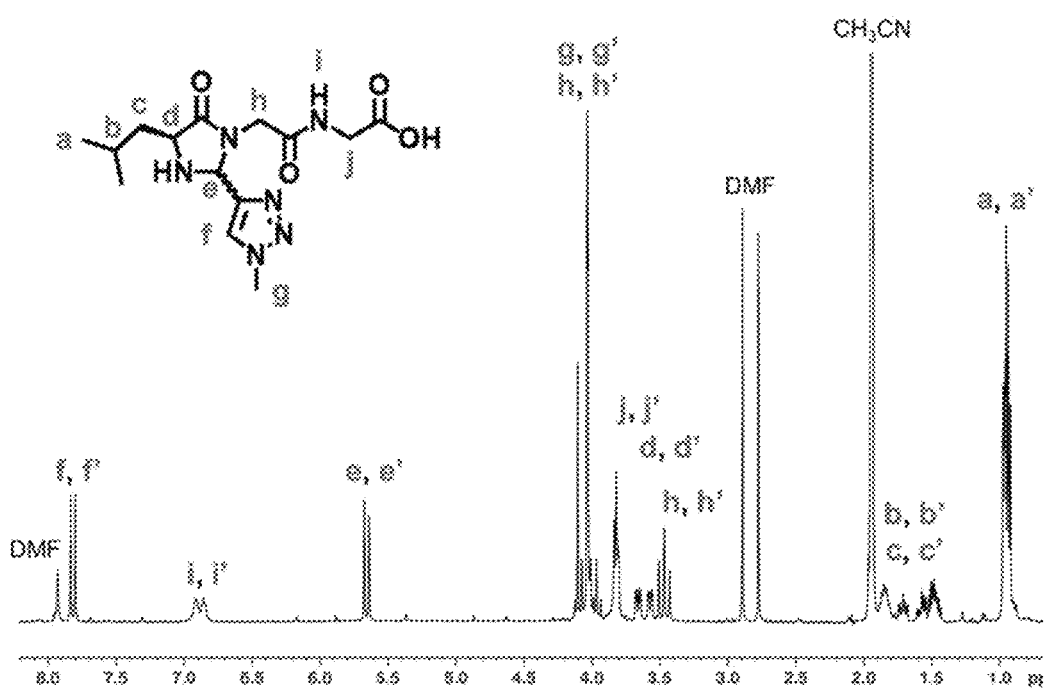
FIG. 20 shows the $^1$H NMR spectrum (400 MHz, CD$_3$CN) of compound 25.

FIG. 20 shows the assignment results of the $^1$H NMR spectrum of compound 25 in deuterated acetonitrile.

The two peaks at 5.7 ppm were assigned to the proton $H_e$ specific to the 2-position of the 4-imidazolidinone ring, confirming that the formation of the 4-imidazolidine ring at the N-terminus of the peptide proceeds by this reaction. The two peaks are derived from an isomer in which the asymmetric point is the 2-position of the 4-imidazolidinone ring.

Example 10. Protein N-Terminal Modification 1

10-1. Reagent, Solvent, Etc.

Ribonuclease A (RNase) from bovine pancreas was purchased from Roche. Ultrapure water used was obtained by purification with Millipore Integral 3. As other reagents and solvents, commercially available products were used as is.

10-2. Protein Modification

This method targets the N-terminus of a protein. The protein that can be a target is one in which the N-terminal amino group is unmodified and the second amino acid residue from the N-terminus is an amino acid other than proline. As a specific example, the N-terminal modification of ribonuclease A (RNase) from bovine pancreas is described below.

The following shows the amino acid sequence of RNase (PDB: 1FS3).

```
                                              (SEQ ID NO: 2)
KETAAAKFER QHMDSSTSAA SSSNYCNQMM KSRNLTKDRC

KPVNTFVHE SLADVQAVCS QKNVACKNGQ TNCYQSYSTM

SITDCRETGS SKYPNCAYKT TQANKHIIVA CEGNPYVPVH

FDASV
```

The N-terminal modification of the protein was performed with reference to a published report (J. I. MacDonald, H. K. Munch, T. Moore, M. B. Francis, Nat. Chem. Biol. 2015, 11, 326-331). The specific experimental procedure is described below.

Figure 21:
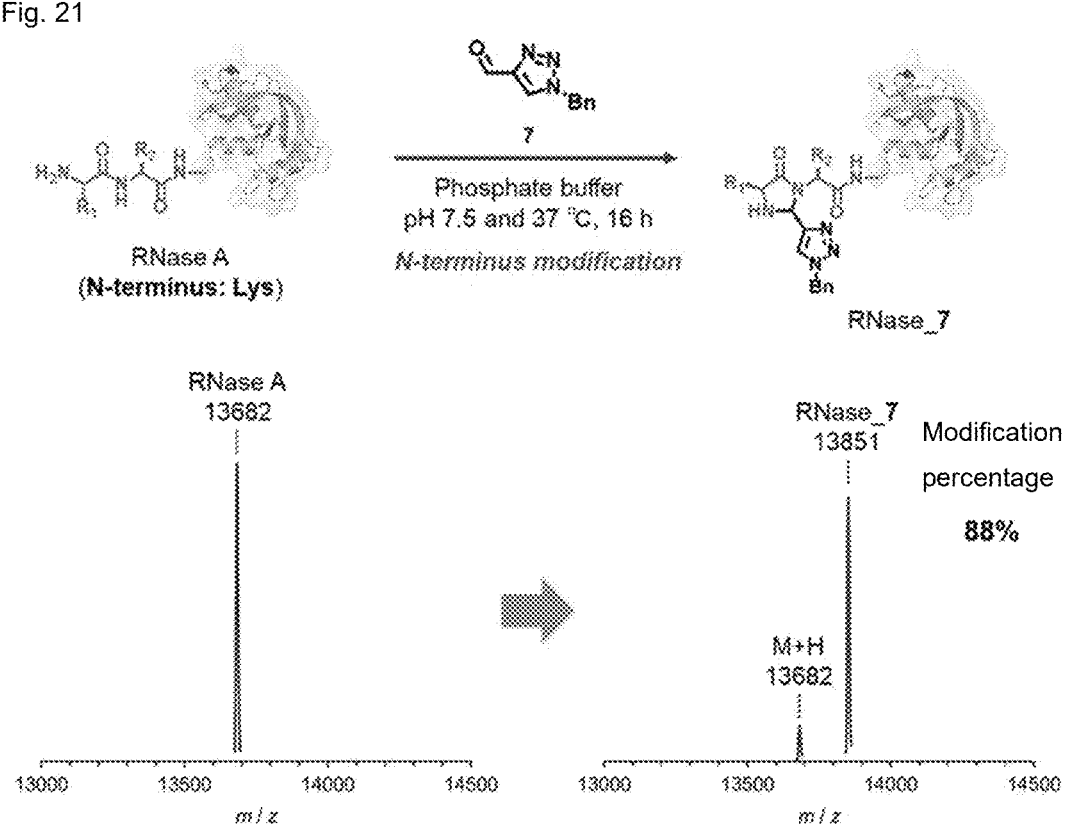
FIG. 21 shows the reaction scheme and results of an N-terminal modification reaction of RNase A (Example 10).

A solution of compound 7 in dimethyl sulfoxide (DMSO) (200 mM, 2.5 µL, 0.5 µmol, final concentration: 10 mM) was diluted with potassium phosphate buffer (10 mM, pH 7.5, 45 µL). A solution of RNase in ultrapure water (1 mM, 2.5 µL, 2.5 nmol, final concentration: 50 µM) was added thereto, and the mixture was shaken at 37° C. for 16 hours. The modification percentage (=modified RNase/(total RNase amount)) was evaluated from the peak intensity in a mass spectrum by using LC/MS. FIG. 21 shows the results. The modification percentage under this reaction condition was calculated as 88%. The product after the reaction was purified by size exclusion chromatography as necessary.

Example 11. Modification to N-Terminus of Protein with Functional Molecule 11-1. Reagent, Solvent, Etc.

Ribonuclease A (RNase) from bovine pancreas was purchased from Roche. Ultrapure water used was obtained by purification with Millipore Integral 3. As other reagents and solvents, commercially available products were used as is.

11-2. Modification to N-Terminus of Protein with Biotin

Figure 22:
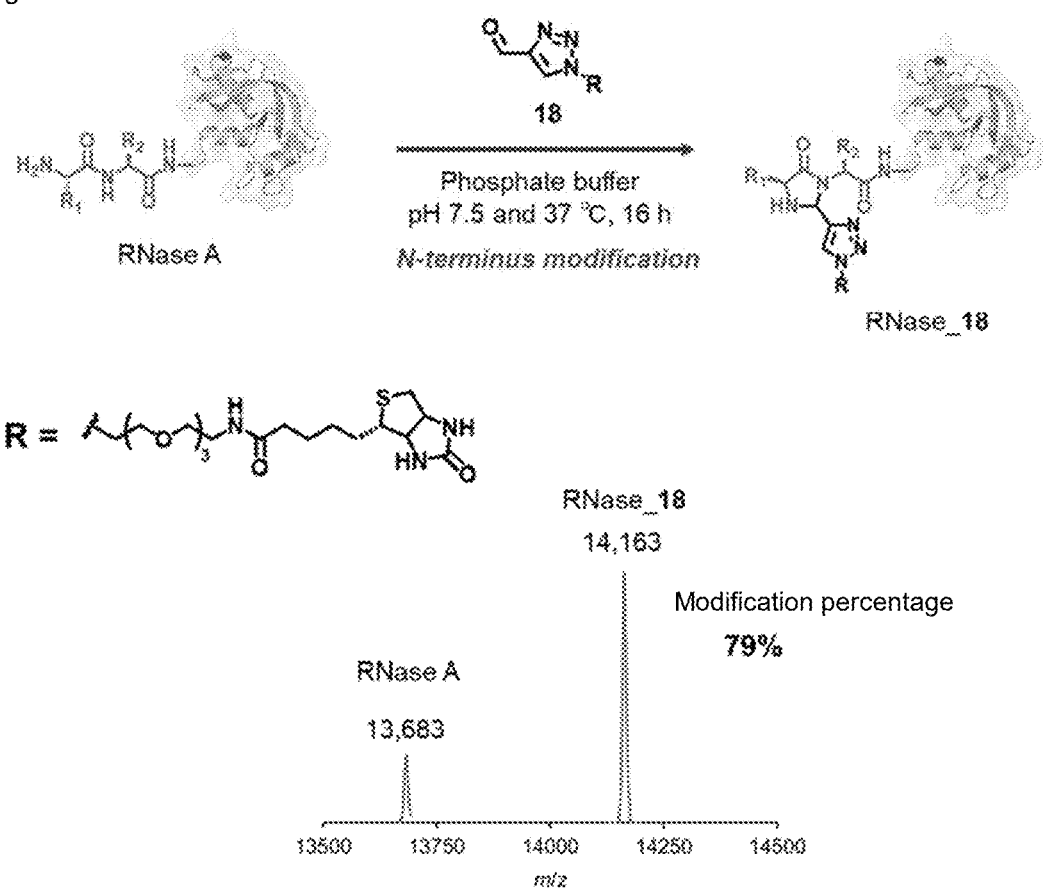
FIG. 22 shows the reaction scheme and results of modification to RNase A with biotin (Example 11-2).

Modification to the N-terminus of the protein with biotin was performed using compound 18 as a modifying agent by the same method as in Example 10-2. FIG. 22 shows the results of LC/MS analysis of the product. The modification percentage regarding the biotin moiety was calculated as 79%.

11-3. Modification to N-Terminus of Protein with Fluorescent Dye

Figure 23:
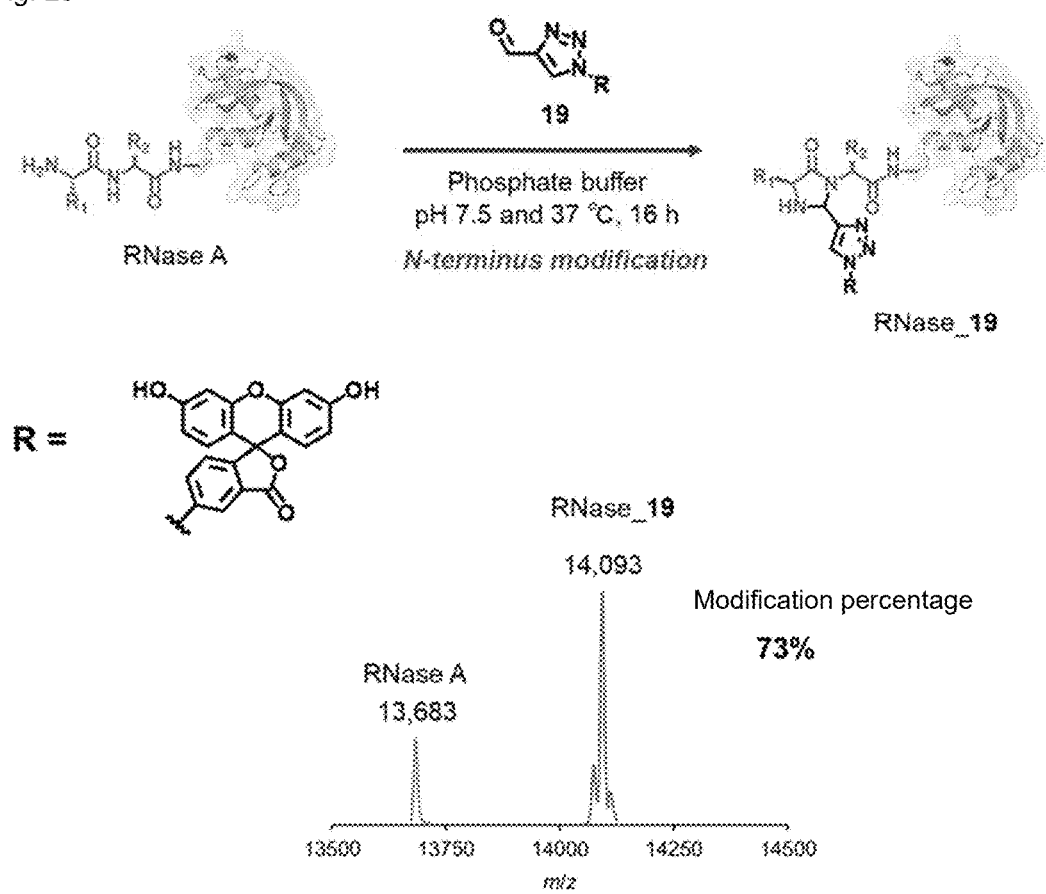
FIG. 23 shows the reaction scheme and results of modification to RNase A with a fluorescent dye (Example 11-3).

Modification to the N-terminus of the protein with a fluorescent dye (here, a fluorescein molecule) was performed using compound 19 as a modifying agent by the same method as in Example 10-2. FIG. 23 shows the results of LC/MS analysis of the product. The modification percentage regarding the fluorescent dye moiety was calculated as 73%.

11-4. Modification to N-Terminus of Protein with Azido Group

Figure 24:
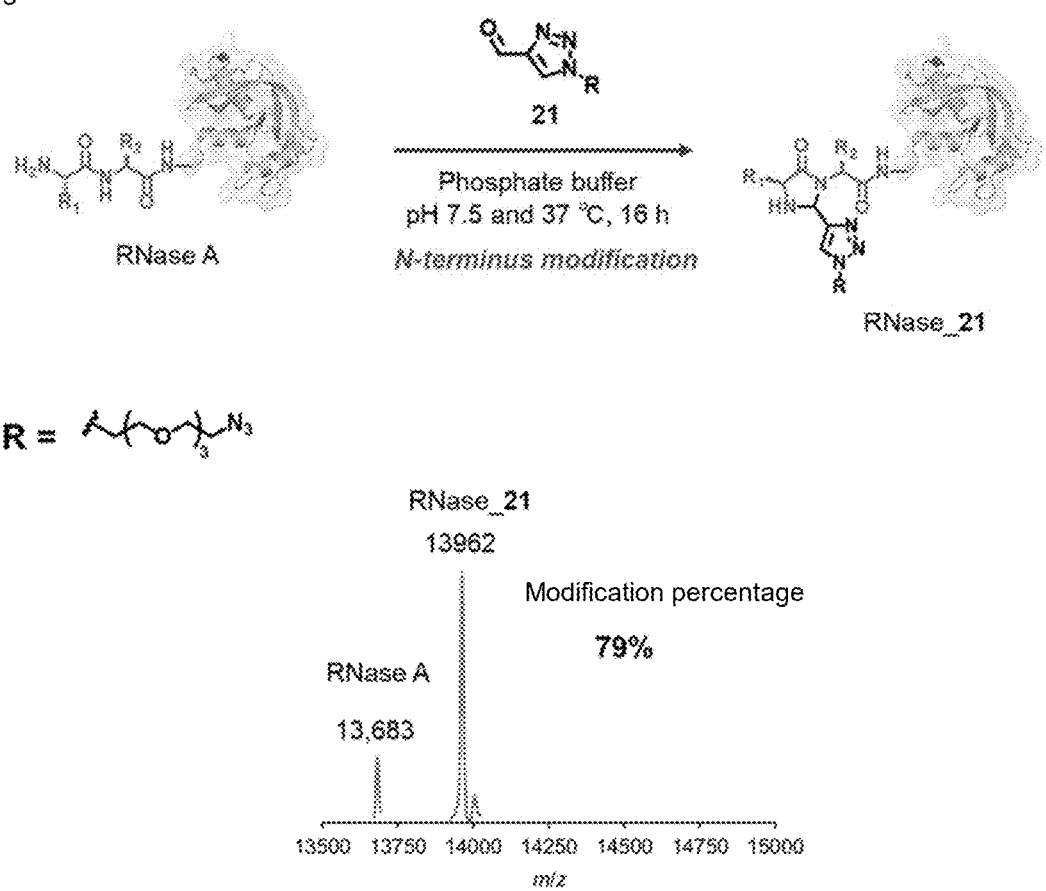
FIG. 24 shows the reaction scheme and results of modification to RNase A with an azido group (Example 11-4).

Modification to the N-terminus of the protein with an azido group was performed using compound 21 as a modifying agent by the same method as in Example 10-2. FIG. 24 shows the results of LC/MS analysis of the product. The modification percentage regarding the azido group was calculated as 79%.

Figure 25:
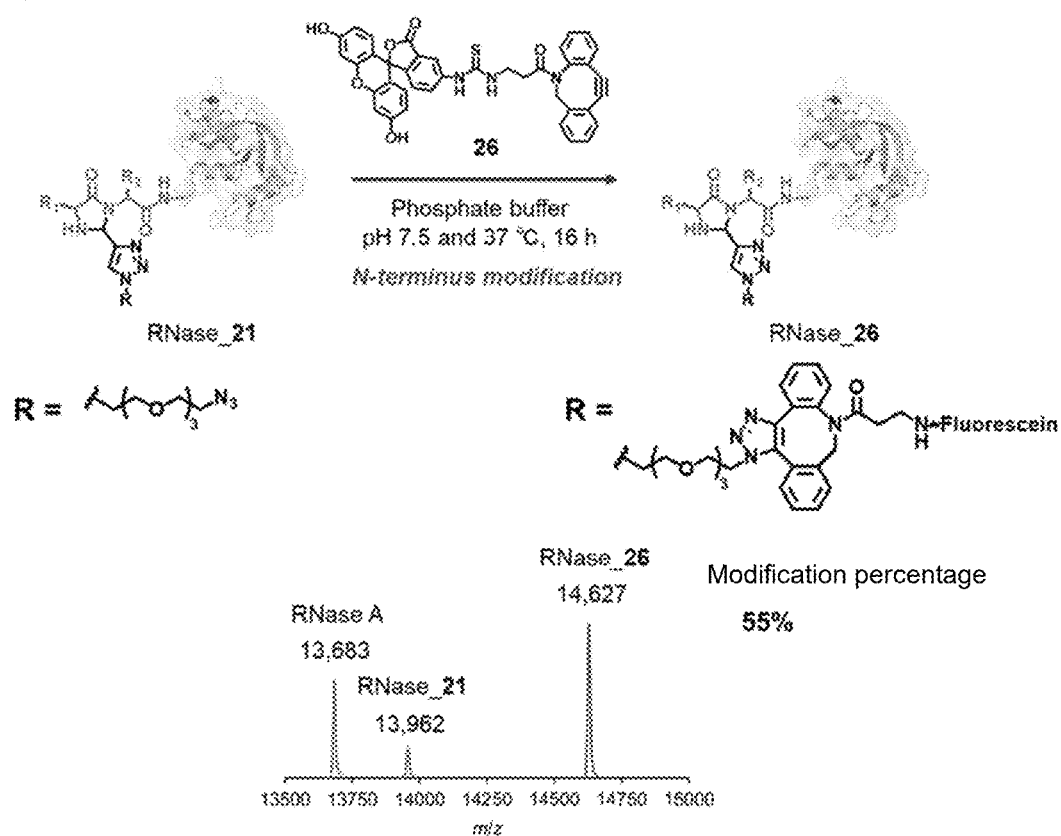
FIG. 25 shows the reaction scheme and results of modification with a fluorescent dye by a strain-promoted alkyne-azide cycloaddition reaction (Example 11-5).

11-5. Modification with Functional Molecule, Starting from Azido Group with which N-Terminus of Protein is Modified The azido group-modified RNase prepared in Example 11-4 was modified with a fluorescent dye by a strain-promoted alkyne-azide cycloaddition reaction. Compound 26, fluorescein having a dibenzocyclooctyne moiety as an alkyne substrate, was used in the reaction. FIG. 25 shows the scheme and results.

A solution of compound 26 in dimethyl sulfoxide (DMSO) (10 mM, 1 µL, final concentration: 100 µM) was added to a phosphate buffer solution containing RNase_21 (RNase_21 concentration: 120 µM, final concentration: 20 µM, buffer solution concentration: 10 mM, pH 7.5, 82.3 µL), and the mixture was left to stand at 4° C. for 16 hours. The modification percentage regarding the fluorescent dye moiety was calculated as 55%.

11-6. Modification to N-Terminus of Protein with Strained Alkyne Moiety

Figure 26:
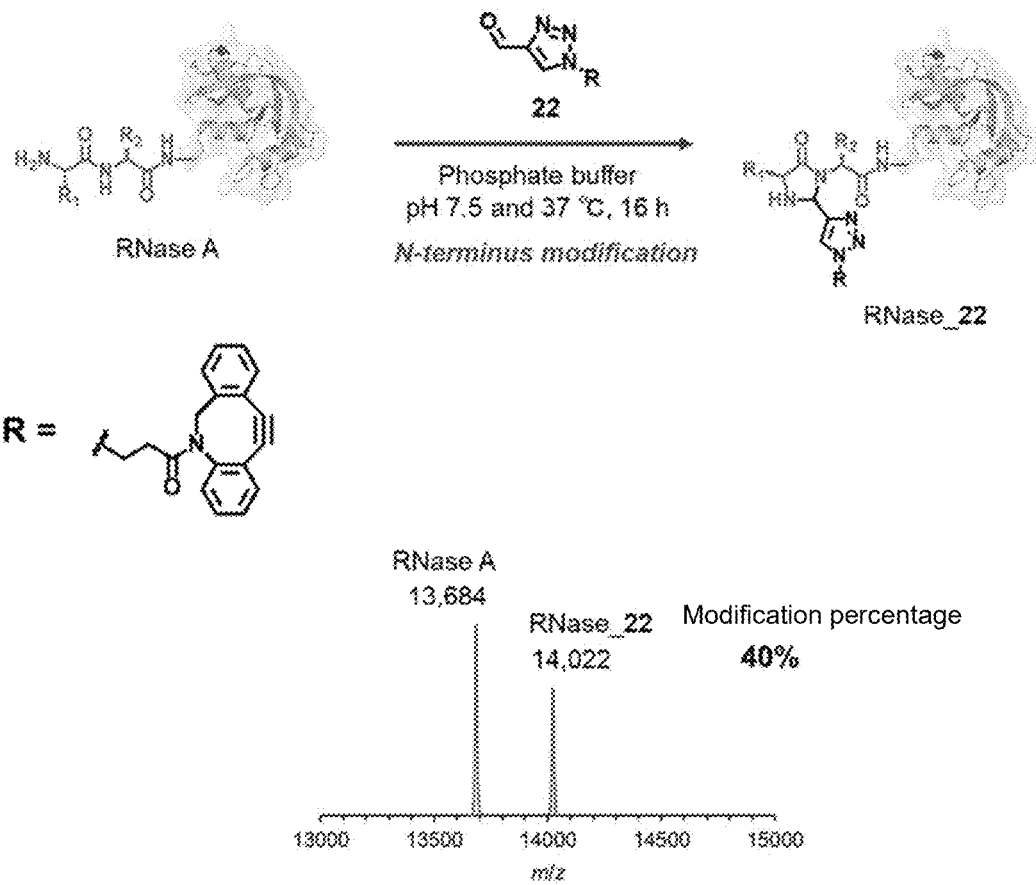
FIG. 26 shows the reaction scheme and results of modification to RNase A with a strained alkyne moiety (Example 11-6).

Modification to the N-terminus of the protein with a strained alkyne moiety was performed using compound 22 as a modifying agent by the same method as in Example 10-2. FIG. 26 shows the results of LC/MS analysis of the product. The modification percentage regarding the cyclooctyne moiety was calculated as 40%.

Figure 27:
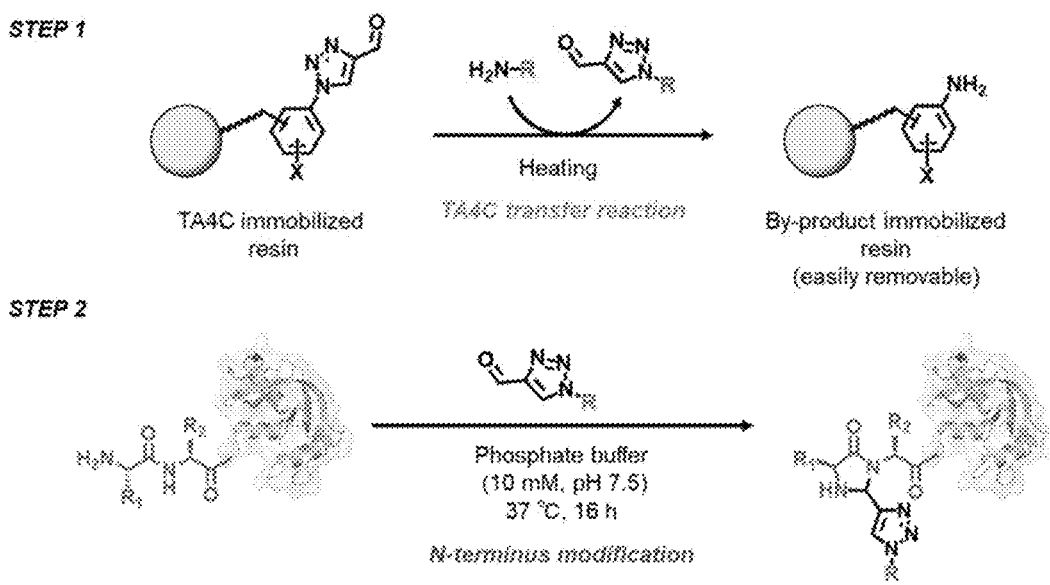
FIG. 27 shows a summary of a method in which the removal of a by-product (aniline derivative) generated after a reaction is simplified by immobilizing various carbaldehyde precursors on resins or solid materials, and the solution after the reaction is directly used for N-terminal modification of a protein (Example 12).

Example 12. Synthesis of Resin on which Reactant is Immobilized, for Heterogeneous Reaction The construction of a new N-terminal selective modifying agent by the rearrangement reaction between compound 10 and the amine precursor shown in Example 6 is useful as a clean reaction without using a copper catalyst. Thus, FIG. 27 shows a method that simplifies removal of a by-product (aniline derivative) generated after the reaction and directly uses the solution after the reaction for protein N-terminal modification by immobilizing various carbaldehyde precursors on resins or solid materials.

12-1. Equipment, Reagent, Solvent, Etc. Used

The equipment, reagents, and solvents used were similar to those in Examples 1 and 8. The aminomethyl polystyrene resin used was purchased from Tokyo Chemical Industry Co., Ltd.

12-2. Synthesis of Resin on which Reactant is Immobilized

Figure 28:
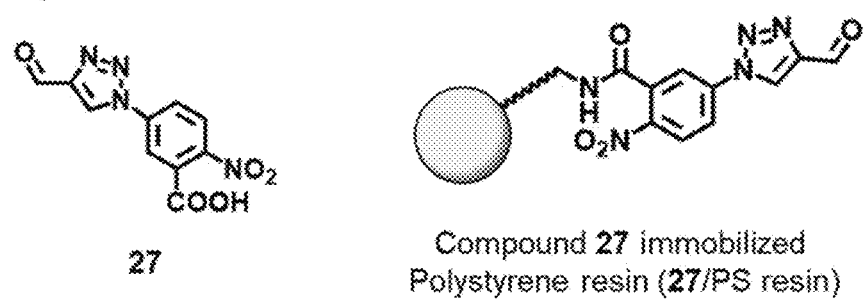
FIG. 28 shows compound 27 and a resin on which compound 27 is immobilized (Example 12).
Figure 29:
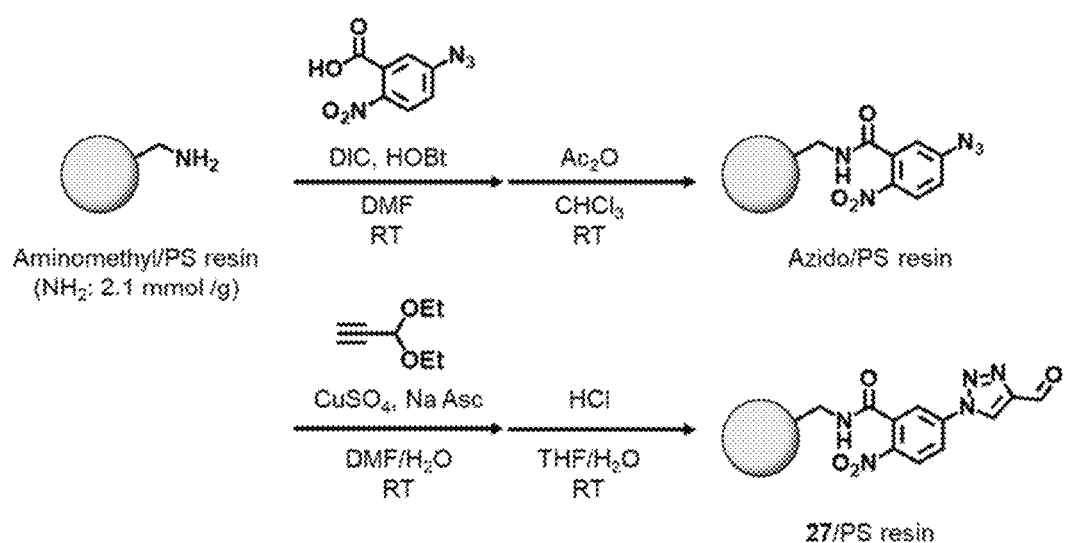
FIG. 29 shows the synthesis scheme of a 27/PS resin (Example 12-2).

As a specific example, FIG. 28 shows synthesis of a polystyrene resin on which compound 27 is immobilized. The synthesis was performed according to the scheme shown in FIG. 29.

After an aminomethyl polystyrene resin (Aminomethyl/PS resin, 200 mg) was dispersed in DMF (30 mL), the resin was swollen by shaking for 10 minutes. 5-azido-2-nitrobenzoic acid (208 mg, 1.0 mmol), 1-hydroxybenzotriazole monohydrate (200 mg, 1.3 mmol), and N,N'-diisopropylcarbodiimide (156 µL, 1.0 mmol) were added to the dispersion of the resin, and the mixture was shaken overnight. The resin after the reaction was filtered, washed with dimethylformamide-pure water-chloroform, and acetone in this order, and dried under reduced pressure. Subsequently, to inactivate unreacted amino, the resulting resin was treated with a mixed solution of acetic anhydride (1 mL) and chloroform (4 mL) for 30 minutes, washed with chloroform-methanol, and acetone, and dried under reduced pressure to give an azido group-modified polystyrene resin (Azido/PS resin).

After the Azido/PS resin (220 mg) was swollen with a mixed solution of DMF/water (6:1, 7 mL), copper (II) sulfate pentahydrate (25 mg, 0.1 mmol), sodium ascorbate (40 mg, 0.2 mmol), and propargylaldehyde diethyl acetal (356 µL, 2.5 mmol) were added to the resin dispersion, and the mixture was shaken at room temperature for 12 hours. The resin after the reaction was filtered, and washed with dimethylformamide-pure water-chloroform, methanol, and acetone in this order.

Subsequently, the resin was treated with a 12% aqueous ammonia solution (5 mL) for 10 minutes, filtered, and washed with pure water to remove the remaining copper catalyst on the resin surface. Finally, the resulting resin was treated with a mixed solution of an aqueous hydrochloric acid solution/tetrahydrofuran (1:1, 5 mL) a total of three times, for 2 minutes each time, filtered, and washed with pure water and acetone to deprotect the acetal protecting group, thereby obtaining a resin on which compound 27 was immobilized (27/PS resin).

12-3. Identification of Resin

Figure 30:
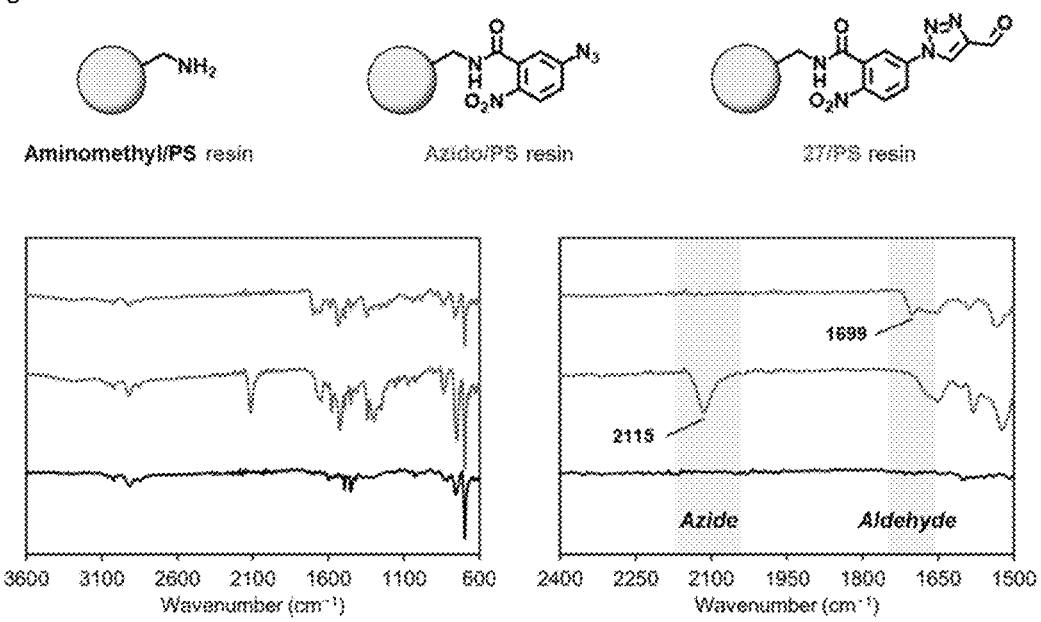
FIG. 30 shows the results of resin identification using infrared spectroscopy (Example 12-3). The right is an enlarged view.

The chemical species on the surface of the resin on which compound 27 was immobilized (27/PS resin) were identified by infrared spectroscopy. FIG. 30 shows the results. In the azido group-modified resin (Azido/PS resin), stretching vibrations characteristic of the azido group were observed at 2115 $cm^{-1}$. In the resin after the formation of the triazole ring by CuAAC reaction (27/PS resin), the azido stretching vibration peak disappeared, and absorption at 1699 $cm^{-1}$ derived from stretching vibrations of the aldehyde group was newly observed. The above results support the modification with the aldehyde group by CuAAC reaction and reveal that the 27/PS resin was prepared.

12-4. Protein N-Terminal Modification

Preparation of an N-terminus-modifying agent and successive protein N-terminal modification were performed using the prepared resin on which a reactant was immobilized (27/PS resin). As a specific example, ribonuclease A (RNase A) N-terminal modification is described below.

Figure 31:
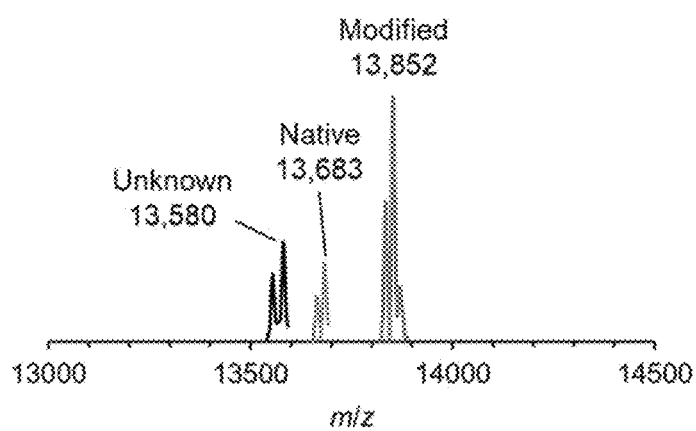
FIG. 31 shows the results of LC/MS analysis of RNaseA modified at the N-terminus by a successive reaction using a resin on which a reactant is immobilized (27/PS resin) (Example 12-4).

The 27/PS resin (5 mg) was added to a solution of benzylamine in dimethyl sulfoxide (100 mM, 50 µL, 5 µmol), and the mixture was heated using a heat block at 100° C. for 90 minutes. After the resulting mixture was air-cooled to room temperature, the supernatant (10 µL, 1 µmol) was diluted with a phosphate buffer solution (10 mM, pH 7.5, 85 µL). An RNase A solution (1 mM, 5 µL, 5 nmol) was added thereto, and the mixture was shaken at 37° C. for 16 hours. After the reaction, modification evaluation using LC/MS was performed. Even in the case of using the resin on which a reactant was immobilized (27/PS resin), a modification percentage (75%) comparable to that in the case of using the isolated and purified N-terminus-modifying agent was obtained. This result demonstrates a method for N-terminal modification of a protein by the successive reaction using the resin on which a reactant was immobilized (27/PS resin). FIG. 31 shows the results.

Figure 32:
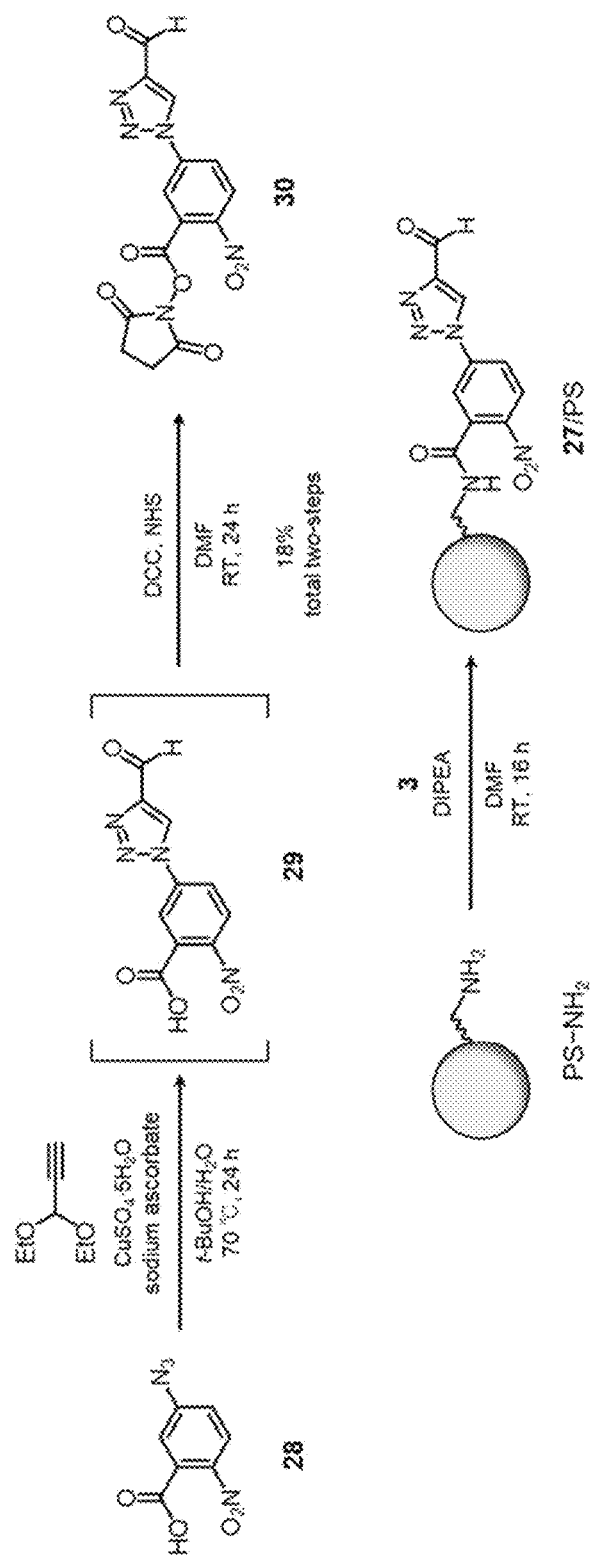
FIG. 32 shows the synthesis scheme of a 27/PS resin (Example 12-5).

12-5. Improvement of Synthesis Method for Resin on which Reactant is Immobilized In Example 12-3, in the sample obtained by performing protein modification, a product in which oxygen appeared to be added to the protein was observed. This is considered to be because the copper catalyst used for the resin synthesis remained on the resin. Therefore, a 27/PS resin was prepared under a new synthetic scheme, and applied to protein modification. Specifically, a 27/PS resin was prepared according to the scheme shown in FIG. 32.

12-5-1. Synthesis of 5-Azido-2-Nitrobenzoic Acid (28)

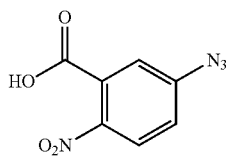

An aqueous solution (6 mL) of sodium nitrite (727 mg, 10.5 mmol) was added to a concentrated HCl/EtOH/H$_2$O solvent mixture (2:1:2, total 43 mL) containing 5-amino-2-nitrobenzoic acid (1.60 g, 8.9 mmol), and the mixture was stirred at 0° C. for 1 hour. Subsequently, sodium azide (868 mg, 13.4 mmol) was added portionwise, and the solution was vigorously stirred at 0° C. for 1 hour and then stirred at room temperature for 1 hour.

Figure 33:
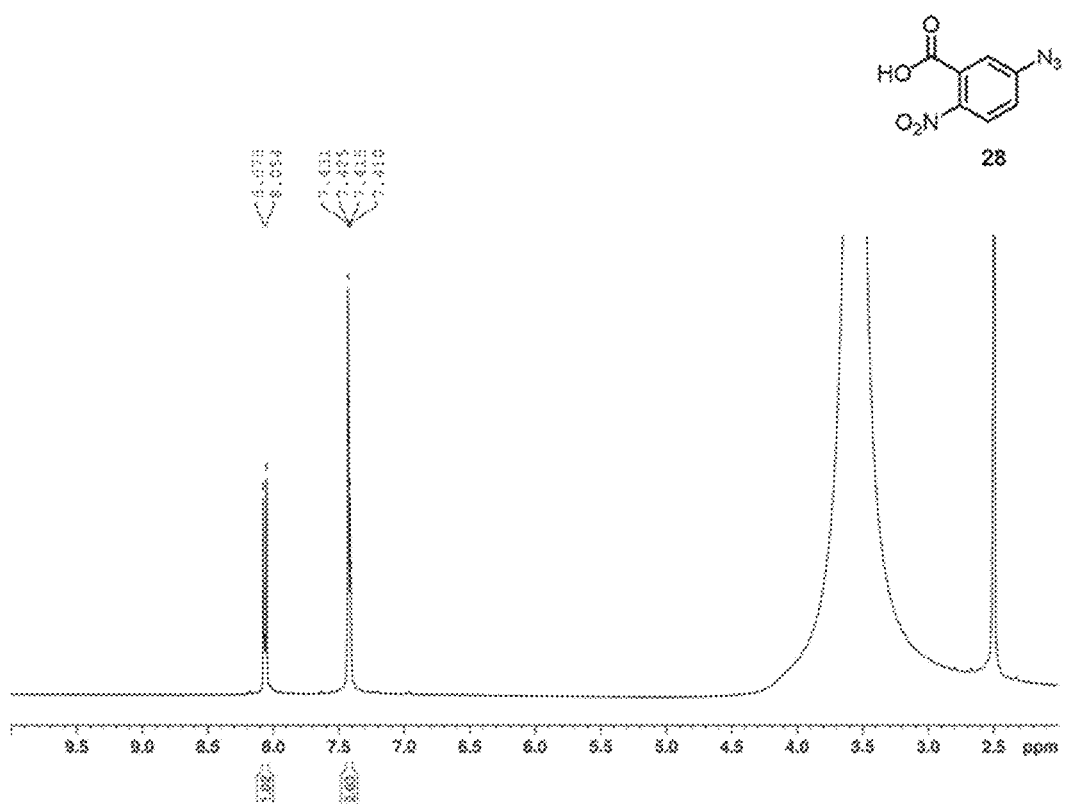
FIG. 33 shows the $^1$H NMR spectrum (400 MHz, DMSO-$d_6$) of compound 28.

The reaction solution was diluted with ultrapure water, filtered, and then washed with ultrapure water (20 mL×2). Drying was performed under reduced pressure to give compound 28 (light-yellow solid). FIG. 33 shows the $^1$H NMR spectrum.

Yield 37%; $^1$H NMR (400 MHz, DMSO-d$_6$): δ, 8.1 (d, J=9.4 Hz, 3H), 7.43-7.41; (m, 2H); $^{13}$C NMR (100 MHz, DMSO-d$_6$): δ, 165.8; 145.3; 143.4; 130.8; 126.2; 121.7; 119.6; ESI-TOF MS (positive mode) m/z calcd. for C$_7$H$_4$NaN$_4$O$_4$ [M+Na]$^+$ 231.012, found 231.011.

12-5-2. Synthesis of 2,5-Dioxopyrrolidin-1-Yl-5-(4-Formyl-1H-1,2,3-Triazol-1-Yl)-2-Nitrobenzoate (30)

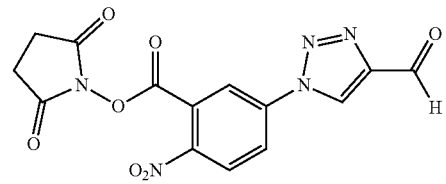

Compound 28 (1.75 g, 8.4 mmol) and 3,3-diethoxyprop-1-yne (1.2 mL, 1.08 g, 8.4 mmol) were dispersed in a mixture of pure water (21 mL) and t-butyl alcohol (21 mL). Copper (II) sulfate pentahydrate (419 mg, 1.68 mmol, 20 mol %) and sodium ascorbate (666 mg, 3.36 mmol, 40 mol %) were added, and the mixture was stirred at 70° C. overnight under a nitrogen atmosphere. After the reaction solution was cooled to room temperature, saturated saline was added to stop the reaction, followed by extraction with ethyl acetate (20 mL×3). The organic layer was dried over sodium sulfate, and the solvents were distilled off under reduced pressure to give a crude product containing compound 29. The purification operation was omitted, and the crude product was used as is in the next reaction.

Figure 34:
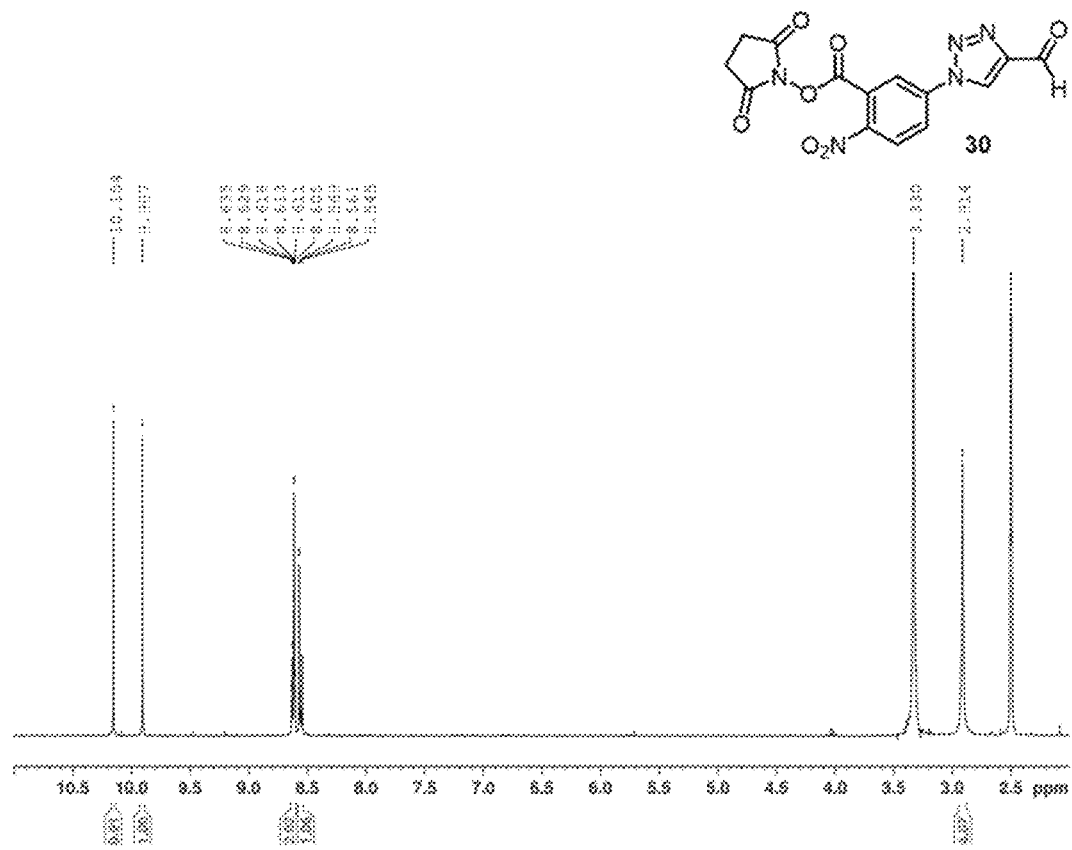
FIG. 34 shows the $^1$H NMR spectrum (400 MHz, DMSO-$d_6$) of compound 30.

N-Hydroxysuccinimide (764 mg, 6.64 mmol) was added to a DMF solution (22 mL) containing the crude product, and the mixture was stirred at room temperature for 10 minutes. Subsequently, N,N'-dicyclohexylcarbodiimide (1.14 g, 5.5 mmol) was added, and the reaction mixture was stirred overnight. The precipitate was filtered off, and the filtrate was dried under reduced pressure to remove the solvent. The residue was dissolved in ethyl acetate (50 mL), and the resulting precipitate was filtered off again. The resulting filtrate was washed with saturated saline (20 mL×2), the organic layer was dried over sodium sulfate, and the solvent was distilled off under reduced pressure to give a crude product containing compound 29. Purification by silica gel column chromatography was performed to give compound 30 (light-yellow solid). FIG. 34 shows the $^1$H NMR spectrum.

Yield 18% (after 2 steps); $^1$H NMR (400 MHz, DMSO-d$_6$): δ10.15 (s, 1H), 9.91 (s, 1H), 8.64-8.61 (m, 2H), 8.57-8.55 (m, 1H), 2.91 (s, 4H); $^{13}$C NMR (100 MHz, DMSO-d$_6$): δ, 184.9, 169.7, 160.1, 147.8, 146.8, 139.3, 127.5, 127.4, 126.0, 123.0, 121.9, 25.6; ESI-TOF MS (positive mode) m/z calcd. for C$_{14}$H$_9$NaN$_5$O$_7$ [M+Na]$^+$ 382.038, found 382.039.

12-5-3. 27/PS Resin Synthesis 2

After an aminomethyl polystyrene resin (Aminomethyl/PS resin, 200 mg) was dispersed in DMF (5 mL), the resin was swollen by shaking for 1 hour. Compound 30 (150 mg, 0.42 mmol) and N,N'-diisopropylcarbodiimide (146 µL, 0.84 mmol) were added to the dispersion of the resin, and the mixture was shaken overnight. The resin after the reaction was filtered, washed with dimethylformamide-pure water-chloroform, and acetone in this order, and dried under reduced pressure. Subsequently, to inactivate unreacted amino, the resulting resin was treated with a mixed solution of acetic anhydride (1 mL) and chloroform (4 mL) for 30 minutes, washed with chloroform-methanol, and acetone, and dried under reduced pressure to give a 27/PS resin.

12-6. Protein N-Terminal Modification

Figure 35:
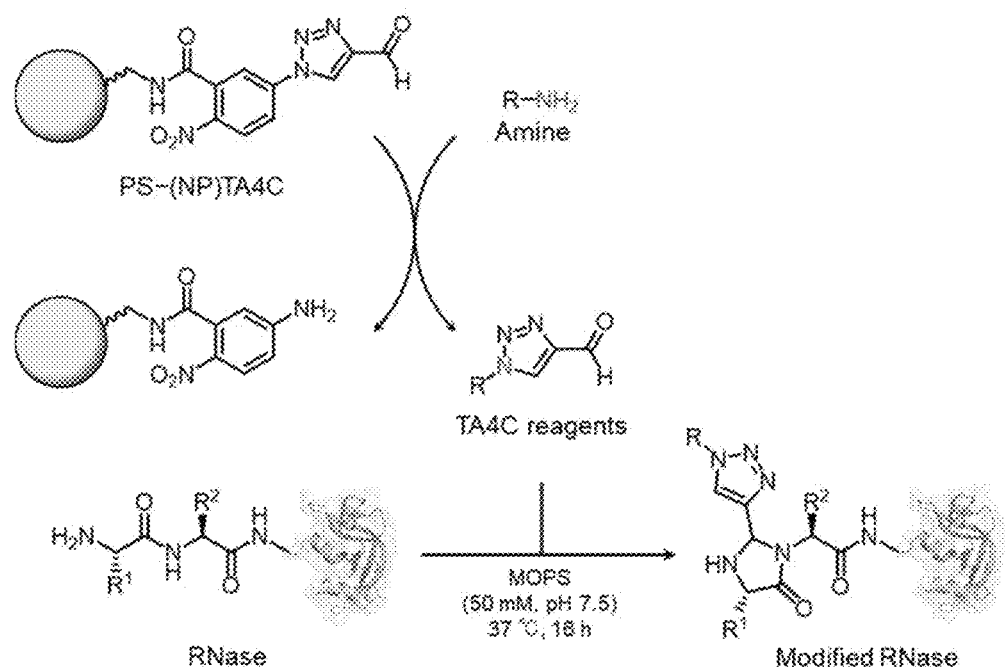
FIG. 35 shows the scheme of N-terminal modification by a successive reaction using a resin on which a reactant is immobilized (27/PS resin) (Example 12-6).

The preparation of an N-terminus-modifying agent and successive protein N-terminal modification were performed using the newly prepared resin on which a reactant was immobilized (27/PS resin). As a specific example, ribonuclease A (RNase A) N-terminal modification is described below FIG. 35 shows the scheme.

Figures 1, 36:
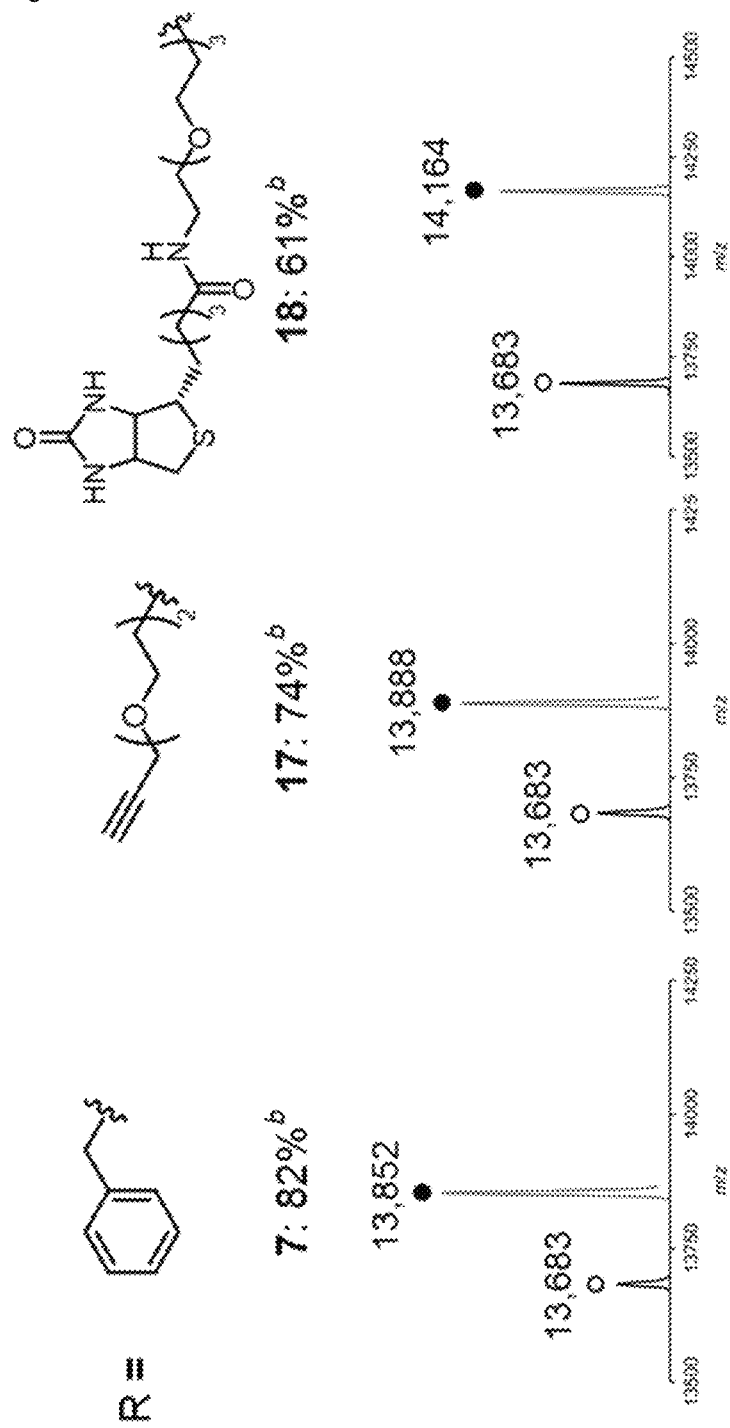

The 27/PS resin (5 mg) was added to a solution (100 mM, 40 μL, 4 μmol) of benzylamine in dimethyl sulfoxide, and the mixture was heated using a heat block at 100° C. for 90 minutes. After the resulting mixture was air-cooled to room temperature, the supernatant (10 μL, 1 μmol) was diluted with a phosphate buffer solution (10 mM, pH 7.5, 85 μL). An RNase A solution (1 mM, 5 μL, 5 nmol) was added thereto, and the mixture was shaken at 37° C. for 16 hours. After the reaction, modification evaluation using LC/MS was performed. FIGS. 36A and 36B show the results. Even in the case of using the resin on which a reactant was immobilized (27/PS resin), a modification percentage (82%) comparable to that in the case of using the isolated and purified N-terminus-modifying agent was obtained. Furthermore, for various functional amine compounds, it was demonstrated that protein N-terminus-specific modification is possible by the same method.

Figure 37:
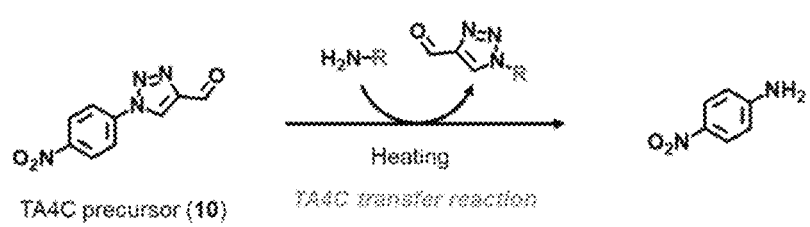
FIG. 37 shows the scheme of the preparation of triazole-carbaldehyde using a Dimroth rearrangement reaction in a homogeneous system, and application to protein modification (Example 13).
Figure 37:
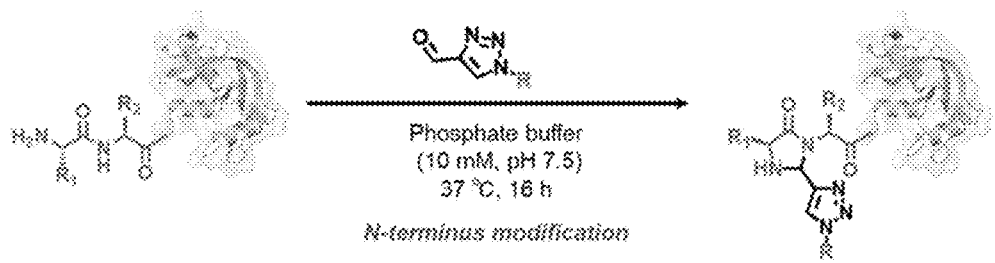

Example 13. Synthesis of Protein-Modifying Agent Using Dimroth Rearrangement Reaction in Homogeneous System and Successive Protein Modification The construction of a new N-terminal selective modifying agent by the rearrangement reaction between compound 10 and the amine precursor shown in Example 6 is useful as a clean reaction without using a copper catalyst. Example 12 shows the Dimroth rearrangement reaction in a heterogeneous system to simplify the removal of a by-product. On the other hand, it is also assumed that there is a case in which the presence of an aniline derivative, which is a by-product, does not pose a problem in protein modification. Thus, this section shows synthesis of a carbaldehyde derivative in a Dimroth rearrangement reaction in a homogeneous system and successive protein modification. FIG. 37 shows the scheme.

13-1. Reagent, Solvent, Etc.

The equipment, reagents, and solvents used were similar to those in Examples 1 and 8. Ribonuclease A (RNase) from bovine pancreas was purchased from Roche. Ultrapure water used was obtained by purification with Millipore Integral 3.

13-2. Optimization of Conditions for Dimroth Rearrangement Reaction

Figure 38:
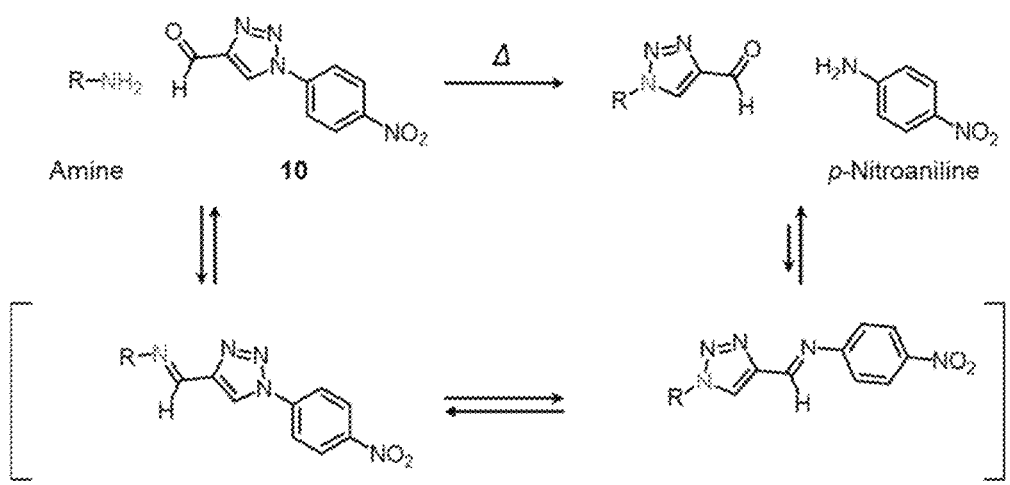
FIG. 38 shows the reaction mechanism of a Dimroth rearrangement reaction (Example 13-2).

FIG. 38 shows the reaction mechanism of a Dimroth rearrangement reaction. Since this reaction includes imine formation as the first step, the addition of an acid catalyst can be expected to improve the reaction efficiency. Thus, a Dimroth rearrangement reaction with compound 10 was performed using benzylamine as a model substrate in the presence of various acid catalysts.

Figure 39:
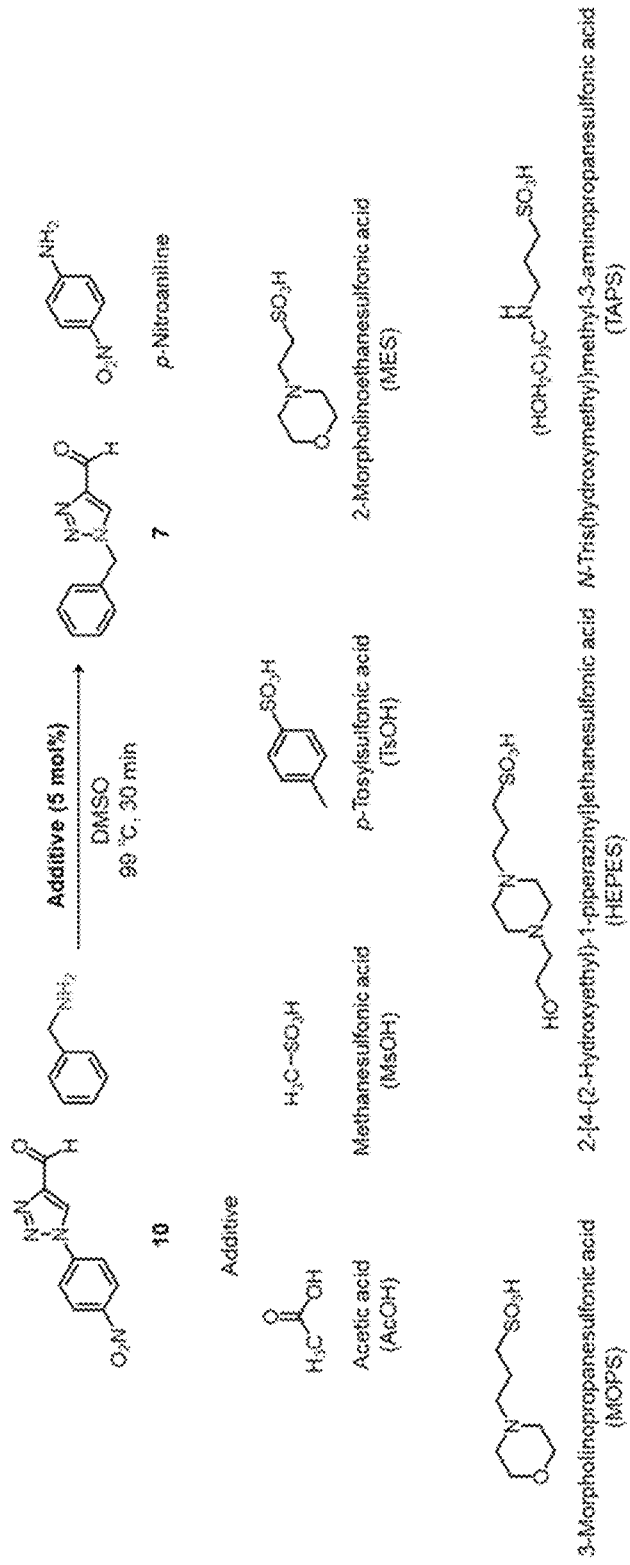
FIG. 39 shows the structures of acid catalysts in a Dimroth rearrangement reaction using compound 10 (Example 13-2).

A solution of compound 10 in dimethyl sulfoxide (200 mM, 20 μL, 4 μmol) and an aqueous acid solution (200 mM or 400 mM, 1 μL, 5 mol % or 10 mol %) were added to a solution of benzylamine in dimethyl sulfoxide (200 mM, 20 μL, 4 μmol), and the mixture was heated using a heat block at 100° C. for 30 minutes. After air-cooling to room temperature, 1 μL, of the reaction mixture was diluted with a phosphate buffer solution (100 mM, pH 7.0, 200 μL) and transferred to a 96-well plate, and ultraviolet-visible absorption measurement was performed. The conversion of the reaction was calculated from a standard curve prepared based on the absorption intensity at 380 nm, which is characteristic of p-nitroaniline, a product. FIG. 39 shows the structures of the acid catalysts used, and Table 1 shows the conversion obtained.

In Table 1, the conversion' was calculated based on the absorption intensity of p-nitroaniline, which is a by-product. The amount of [b]MOPS added was set to 10 mol %.

TABLE 1

| Entry | Additive | Conversion[a] (%) |
|---|---|---|
| 1 | none | 56 |
| 2 | AcOH | 64 |
| 3 | MsOH | 85 |
| 4 | TsOH | 85 |
| 5 | MES | 86 |
| 6 | MOPS | 86 |
| 7 | HEPES | 85 |
| 8 | TAPS | 81 |
| 9[b] | MOPS | 91 |

The above results show that the conversion is improved by addition of acid catalysts. It is suggested that addition of the sulfonic acids is particularly effective. In addition, various sulfonic acid salts, which are known to function as a Good's buffer, were also found to improve the reaction efficiency. In general, because these sulfonic acid salts do not significantly affect the function or structure of proteins, the mixed solution of the Dimroth rearrangement reaction can be directly used for the subsequent protein modification reaction. 3-Morpholinopropanesulfonic acid (MOPS) was selected as an acid catalyst, and the subsequent experiment was performed.

13-3. Protein N-Terminal Modification

Figure 40:
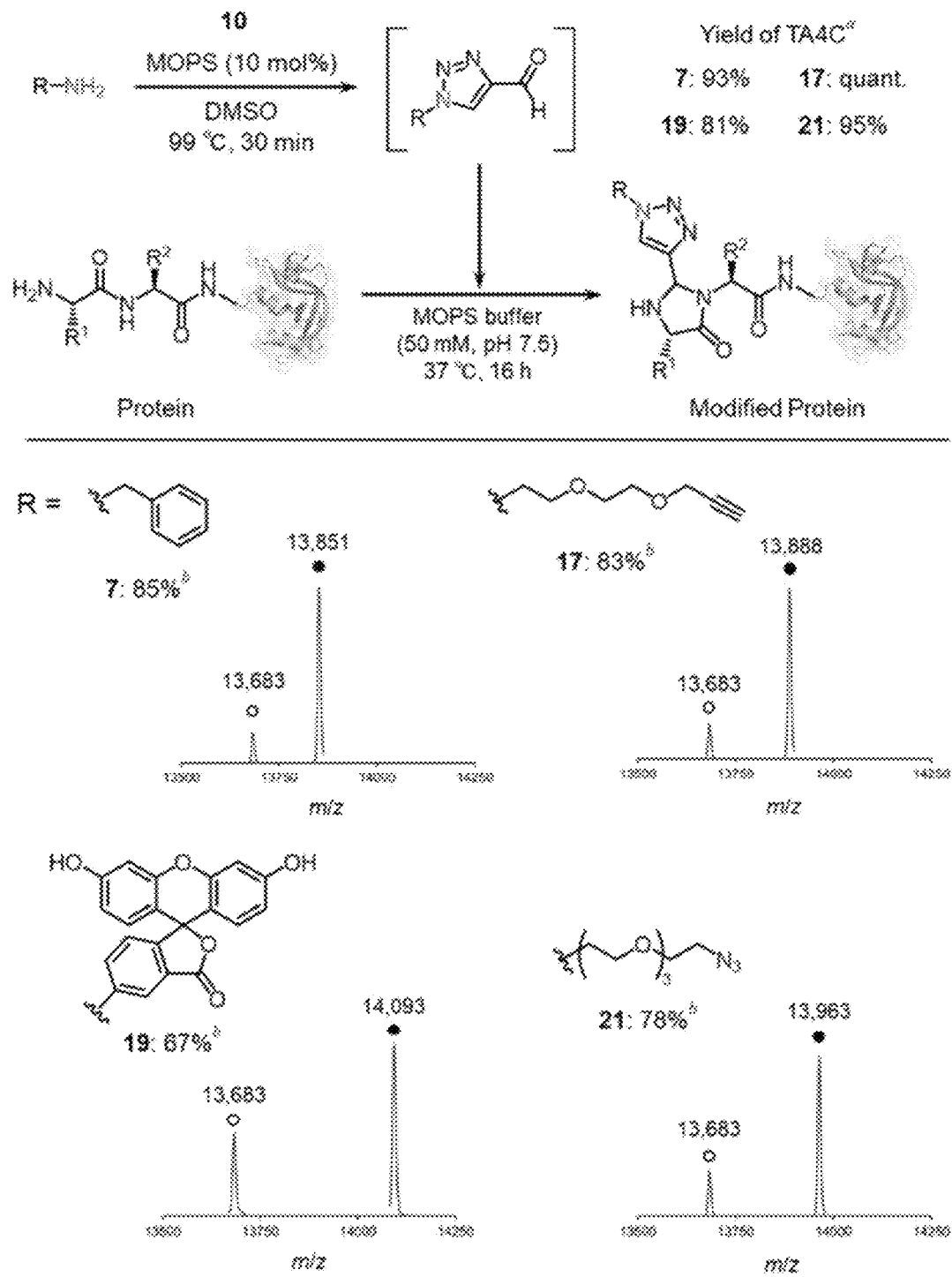
FIG. 40 shows the preparation of N-terminus-modifying agents by a Dimroth rearrangement reaction, and the results of LC-MS analysis of a successive protein modification reaction (Example 13-3). The peaks corresponding to the modified proteins are shown as "●" (solid circles), and peaks corresponding to the unmodified protein are shown as "○" (hollow circles).

A solution of compound 10 in dimethyl sulfoxide (200 mM, 20 μL, 4 μmol) and an aqueous MOPS solution (200 mM or 400 mM, 1 μL, 5 mol % or 10 mol %) were added to a solution of benzylamine in dimethyl sulfoxide (200 mM, 20 μL, 4 μmol), and the mixture was heated using a heat block at 100° C. for 30 minutes. After air-cooling to room temperature, the reaction mixture (5 μL) was diluted with a phosphate buffer solution (10 mM, pH 7.5, 42.5 μL). An RNase A solution (1 mM, 2.5 μL, 5 nmol) was added thereto, and the mixture was shaken at 37° C. for 16 hours. After the reaction, modification evaluation using LC-MS was performed. FIG. 40 shows the results of LC-MS analysis.

Protein-modifying agents were prepared using various functional amine precursors, such as an alkyne, an azide, and a fluorescent dye, and introduction into the N-terminus of the protein was achieved. In addition, even when preparation of the N-terminus-modifying agents, and protein modification reaction were performed successively, the modification percentages were comparable to those in the cases of using the isolated and purified N-terminus-modifying agents. The results demonstrated a method for protein N-terminal modification by the successive reaction using the Dimroth rearrangement reaction in a homogeneous system.

Example 14. Protein N-Terminal Modification Using Bis-TA4C Molecule and Introduction of Functional Molecule by Oxime Formation In Dimroth rearrangement using a diamine having an amino group at both terminal ends as a precursor, a molecule having a TA4C moiety introduced at both terminal ends (hereinafter referral to as "Bis-TA4C") is obtained. In protein N-terminal modification using this Bis-TA4C, an aldehyde moiety can be introduced into the N-terminus of a protein. An example of a chemical modification reaction starting from an aldehyde include oxime formation with hydroxylamine. This reaction is also applicable to protein modification because it proceeds even in water under mild conditions. Moreover, since an oxime bond is a dynamic bond, it is also possible to remove a functional molecule as necessary. Thus, protein modification reactions were performed by performing a Dimroth rearrangement reaction using compound 10, by using various diamines as precursors.

14-1. Reagent, Solvent, Etc.

The equipment, reagents, and solvents used were similar to those in Examples 1 and 8. Ribonuclease A (RNase) from bovine pancreas was purchased from Roche. Ultrapure water used was obtained by purification with Millipore Integral 3.

14-2. Preparation of Bis-TA4C and Protein Modification Reaction

Figure 41:
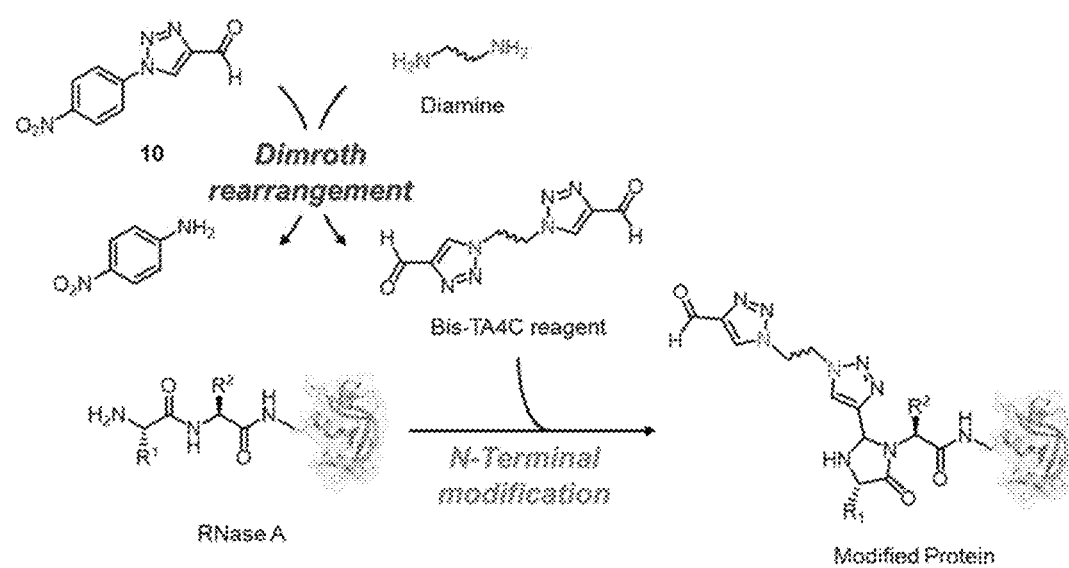
FIG. 41 shows the scheme of the preparation of Bis-TA4C, and a protein modification reaction (Example 14-2).
Figure 42:
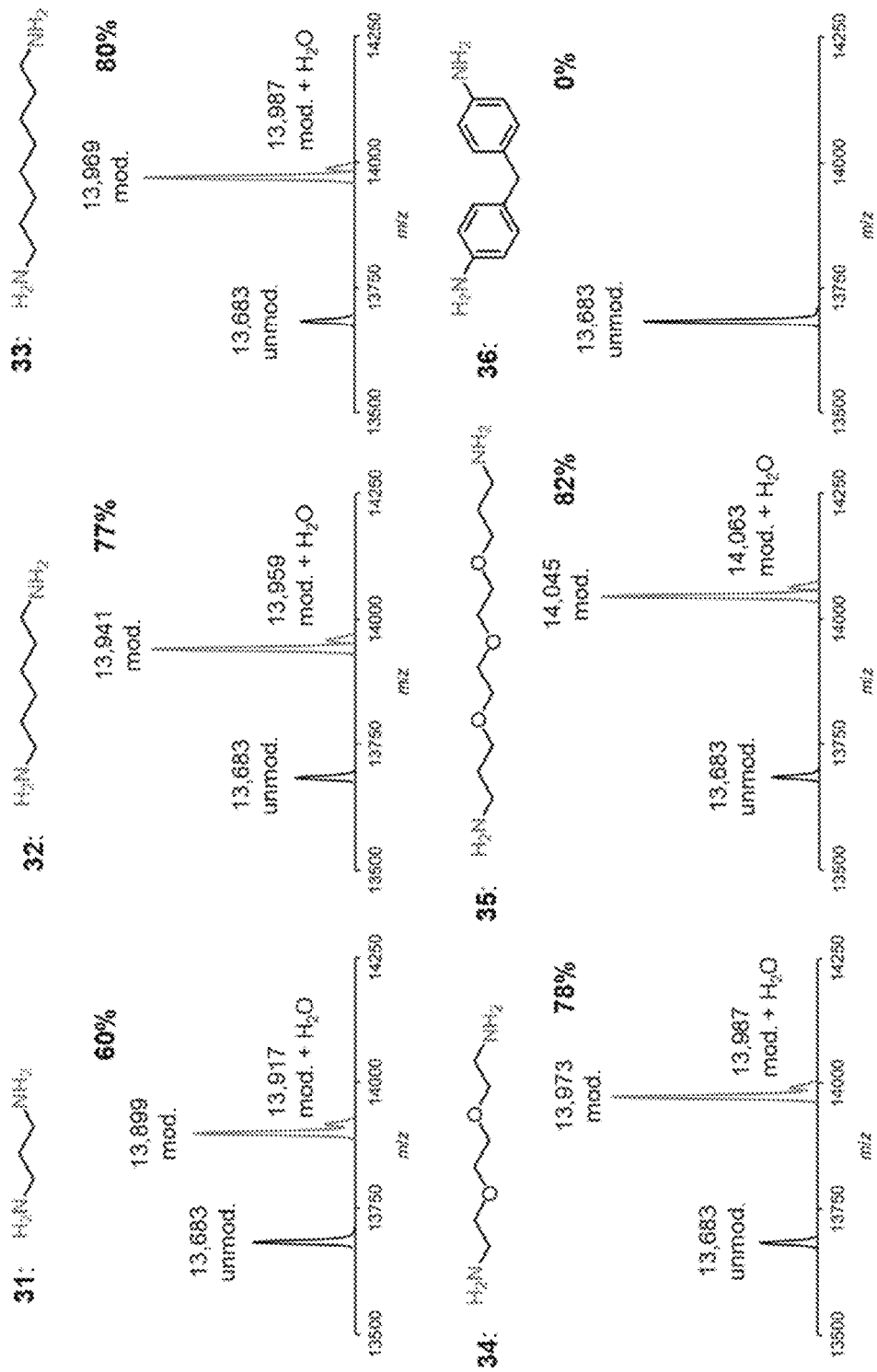
FIG. 42 shows the results of LC-MS analysis of the N-terminal modification of RNaseA with Bis-TA4C using diamines as precursors (Example 14-2). The structures of the diamines as precursors and the modification percentage calculated from LC-MS are shown.

A solution of compound 10 in dimethyl sulfoxide (200 mM, 20 µL, 4 µmol) and an aqueous acid solution (200 mM or 400 mM, 400 mM, 1 µL, 5 mol % or 10 mol %) were added to individual solutions of each of diamines 31-36 in dimethyl sulfoxide (100 mM, 20 µL, 2 µmol), and the mixtures were individually heated using a heat block at 90° C. for 60 minutes. After air-cooling to room temperature, each reaction mixture (5 µL) was diluted with a phosphate buffer solution (10 mM, pH 7.5, 42.5 µL). An RNase A solution (1 mM, 2.5 µL, 5 nmol) was added thereto, followed by shaking at 37° C. for 16 hours. After the reaction, modification evaluation using LC-MS was performed. FIG. 41 shows the scheme, and FIG. 42 shows the results of protein modification.

When Bis-TA4C having an alkyl chain or oligoethylene glycol chain as a linker was used, good modified proteins (60 to 82%) were obtained. In contrast, the modification reaction did not proceed with Bis-TA4C containing an aromatic skeleton such as aniline. This is considered to be due to the significantly low solubility of the Bis-TA4C. Therefore, introduction of a moiety that improves water solubility is expected to improve reaction yield.

Figure 43:
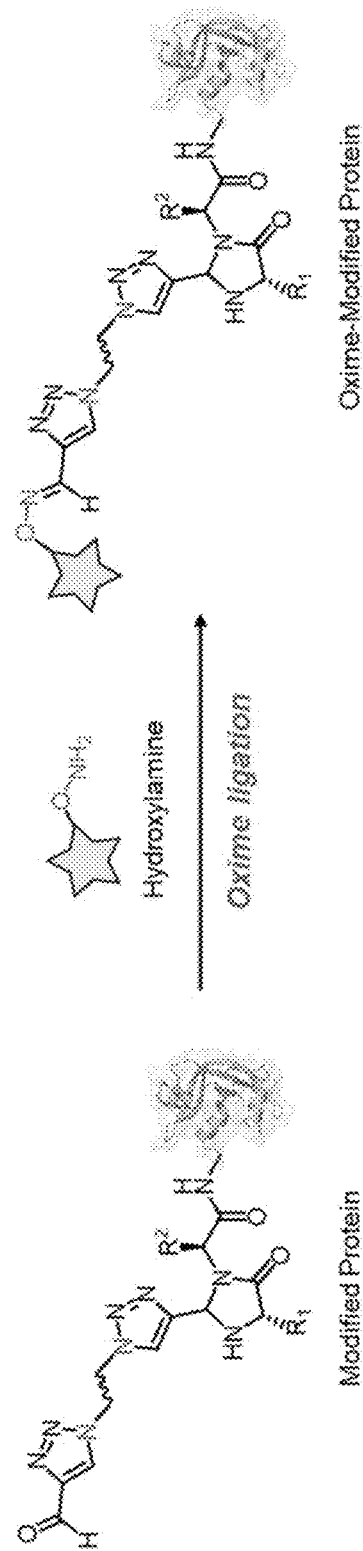
FIG. 43 shows the scheme of introduction of a functional molecule into the N-terminus of a protein via oxime formation (Example 14-3).

14-3. Introduction of Functional Molecule, Via Oxime Formation, into Protein Modified with Bis-TA4C An oxime formation reaction was performed starting from the aldehyde moiety introduced into the N-terminus of the protein with Bis-TA4C. Specifically, the reaction was performed according to the procedure shown in FIG. 43, with reference to a published report (M. Rashidian, M. M. Mahmoodi, R. Shah, J. K. Dozier, C. R. Wagner, M. D. Distefano, Bioconjugate Chem. 2013, 24, 333-342). As examples, modification using a fluorescent dye and polyethylene glycol is described below.

Figure 44:
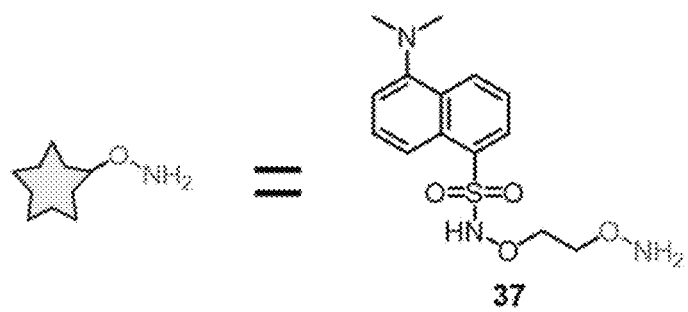
FIG. 44 shows the results of LC-MS analysis of RNase A modified with compound 37 (Example 14-3).
Figure 44:
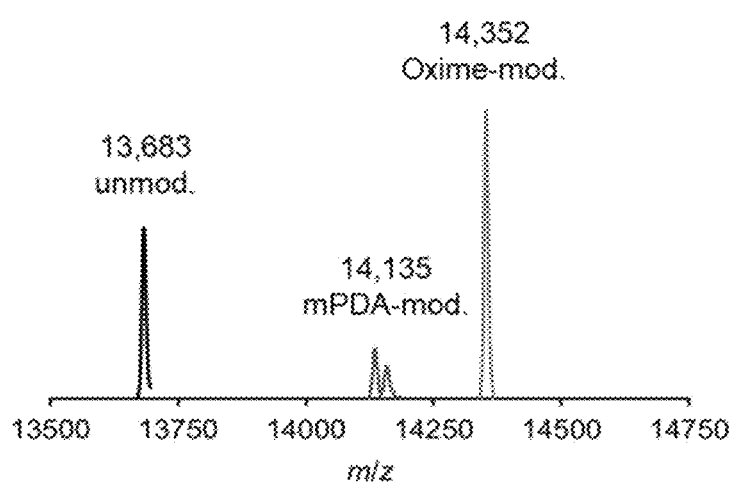

RNase A (60 µM, 8.3 µL, 0.5 nmol) modified with Bis-TA4C prepared using compound 35 as a precursor was diluted with a phosphate buffer solution (50 mM, pH 7.0, 35.7 µL), and a dimethyl sulfoxide solution (5 mM, 1 µL, 5 nmol) containing hydroxylamine 37, and an aqueous m-phenylenediamine (m-PDA) solution (50 mM, 5 µL, 0.25 µmol) as a catalyst were added thereto, followed by shaking at 4° C. for 6 hours. After the reaction, modification evaluation using LC-MS was performed. FIG. 44 shows the results of protein modification. Although some adducts of m-PDA, which is a catalyst, were observed, it was confirmed that conversion to an oxime adduct was achieved in good yield.

Figure 45:
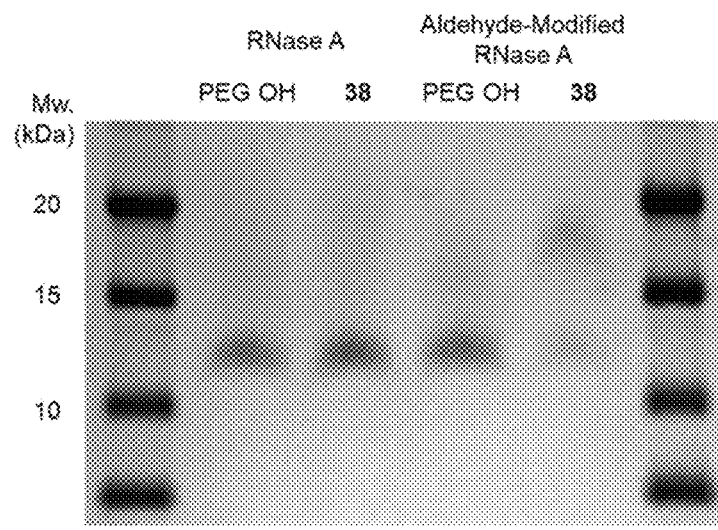
FIG. 45 shows the results of SDS-PAGE analysis of RNase A modified with compound 38 (Example 14-3).
Figure 45:
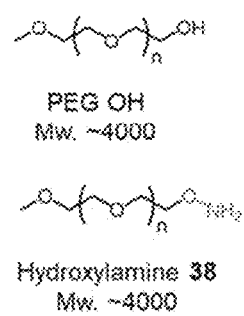

RNase A (60 µM, 8.3 µL, 0.5 nmol) modified with Bis-TA4C prepared using compound 35 as a precursor was diluted with a phosphate buffer solution (50 mM, pH 7.0, 35.7 µL); and hydroxylamine 38 (2 mg, 500 nmol) and an aqueous m-phenylenediamine (m-PDA) solution (50 mM, 5 µL, 0.25 µmol) as a catalyst were added thereto, followed by shaking at room temperature for 16 hours. After the reaction, modification evaluation using SDS-PAGE was performed. FIG. 45 shows the results of protein modification.

As a comparison, experiments were also conducted using an unmodified protein or polyethylene glycol having a hydroxy group as a substrate. A band shift on SDS-PAGE was observed only in the combination of the aldehyde group at the N-terminus of the protein and the hydroxylamine moiety in polyethylene glycol, confirming the introduction of polyethylene glycol by oxime formation.

Example 15. Dimroth Rearrangement Reaction Under Mild Conditions

The preparation of an N-terminus-modifying agent by a Dimroth rearrangement reaction in a homogeneous system shown in Examples 13 and 14 requires a high reaction temperature of 90 to 100° C. Thus, further improvement in the precursor structure and reaction conditions is required for adaptation to substrates with low thermal tolerance. In order to achieve the reaction at a lower temperature, the structure of compound 10, which is a precursor, was modified. In particular, a compound in which the nitrophenyl moiety is changed to a substituent having a higher electron-withdrawing property can be expected to function as a useful precursor because the intermediate is stabilized, and the reverse reaction is less likely to proceed. This section describes the synthesis of a compound according to this strategy and an example of application to a Dimroth rearrangement reaction.

15-1. Compound Synthesis

As a specific structural example, the synthesis of triazolecarbaldehyde 40 having a 4-cyanotetrafluorophenyl group is described below.

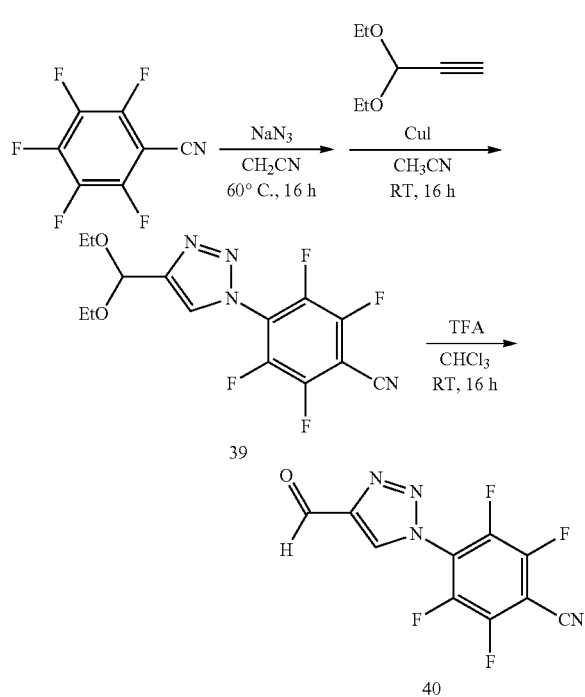

15-1-1. Synthesis of 4-(4-(Diethoxymethyl)-1H-1,2,3-Triazol-1-Yl)-2,3,5,6-Tetrafluorobenzonitrile (39)

Figure 46:
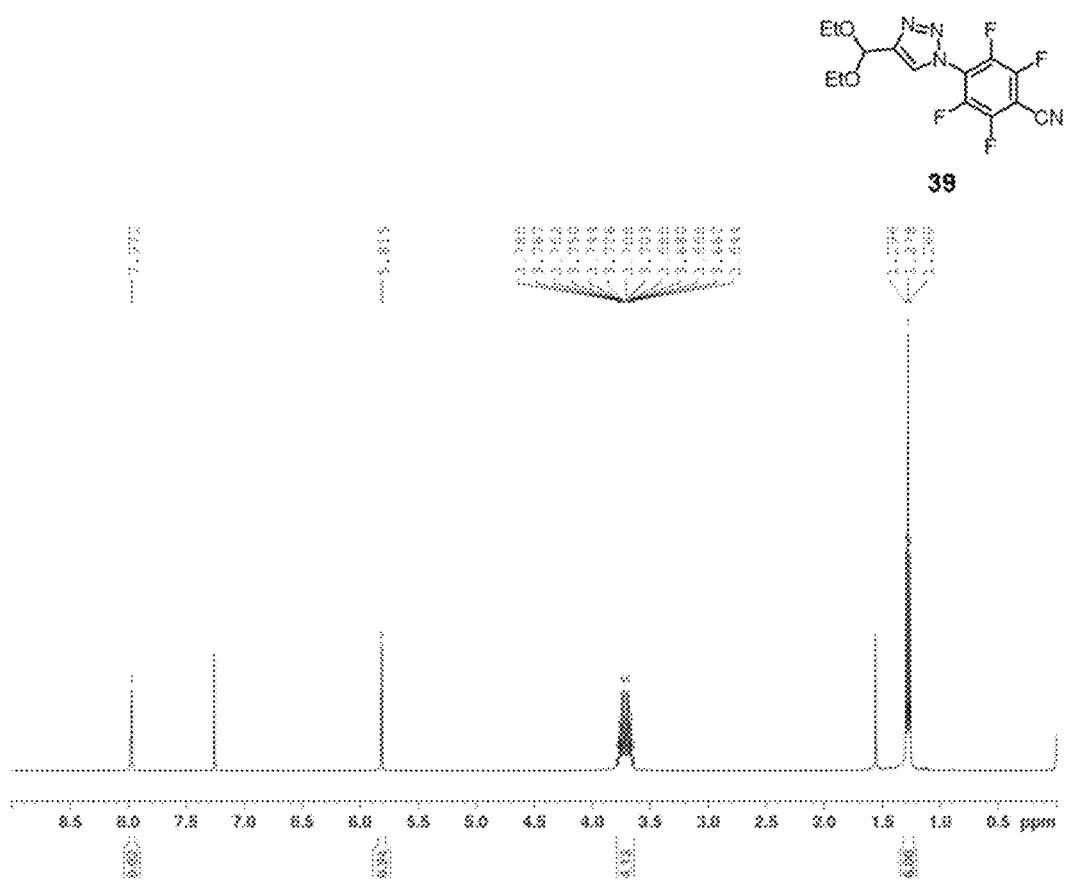
FIG. 46 shows the ¹H NMR spectrum (400 MHz, CDCl₃) of compound 39.

An acetonitrile solution (10 mL) containing pentafluorobenzonitrile (850 mg, 541 µL, 4.4 mmol) and sodium azide (260 mg, 4.0 mmol) was stirred at 60° C. for 16 hours under a nitrogen atmosphere. Subsequently, propargylaldehyde diethyl acetal (570 µL, 4.0 mmol) and copper (1) iodide (76 mg, 0.4 mmol) were added under a nitrogen atmosphere, and the mixture was stirred at room temperature for 16 hours. The reaction solution was air-cooled to room temperature, and then diluted with a saturated sodium chloride aqueous solution (40 mL), followed by extraction with ethyl acetate (50 mL×3). The resulting organic layer was dried over magnesium sulfate, and the filtrate obtained by filtering off solid was distilled off under reduced pressure to give a crude product. The crude product was purified by silica gel column chromatography to give compound 39 (white solid). FIG. 46 shows the $^1$H NMR spectrum.

Yield 86%; $^1$H-NMR (400 MHz, CDCl$_3$): δ7.97 (s, 1H), 5.82 (s, 1H), 3.79-3.64 (m, 4H), 1.28; (t, J=7.1 Hz, 6H).

15-1-2. Synthesis of 2,3,5,6-Tetrafluoro-4-(4-Formyl-1H-1,2,3-Triazol-1-Yl)Benzonitrile (40)

Figure 47:
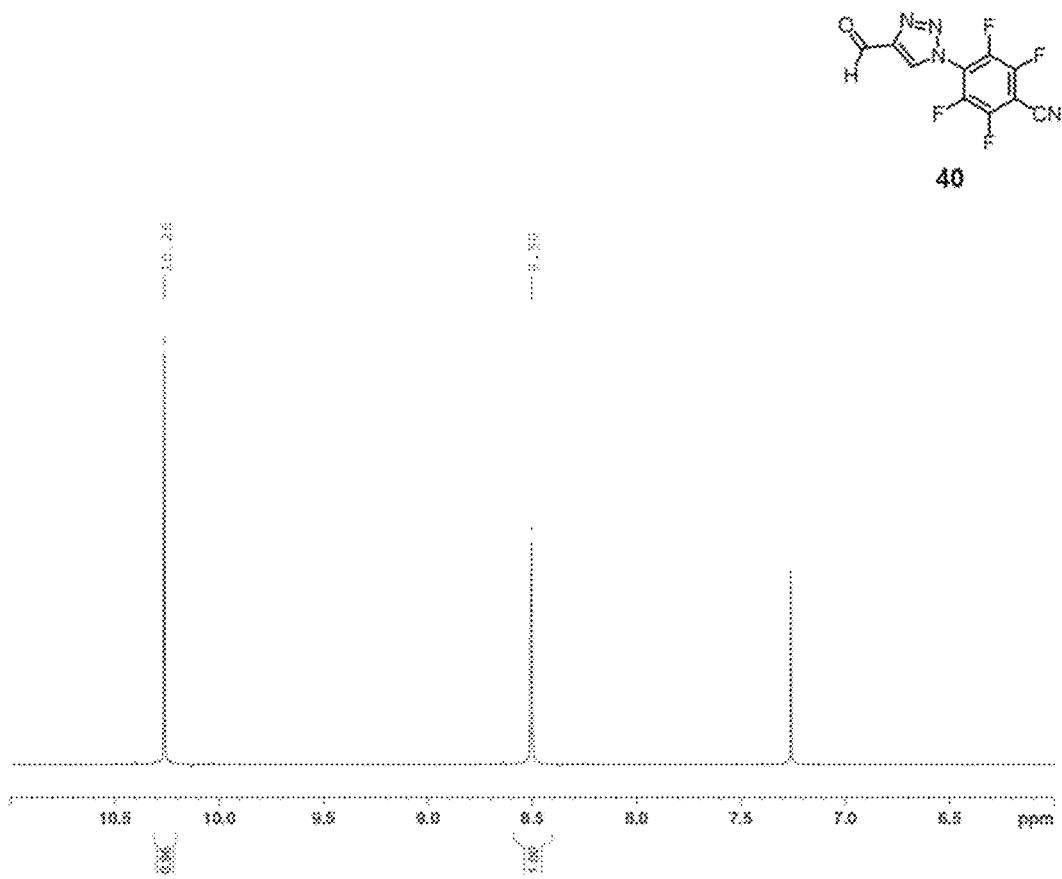
FIG. 47 shows the ¹H NMR spectrum (400 MHz, CDCl₃) of compound 40.

Compound 39 (688 mg, 2.0 mmol) was dissolved in chloroform (4 mL). Trifluoroacetic acid (2 mL) was added thereto, and the mixture was stirred at mom temperature for 16 hours. The solvent and trifluoroacetic acid were removed by distillation under reduced pressure to give a crude product. The crude product was purified by reprecipitation (hexane:chloroform) to give compound 40 (white solid). FIG. 47 shows the $^1$H NMR spectrum.

Yield 78%; $^1$H-NMR (400 MHz, CDCl$_3$): δ10.26 (s, 1H), 8.50 (s, 1H).

15-2. Dimroth Rearrangement Reaction Using Compound 40 as Precursor

To evaluate the reactivity of compound 40, a Dimroth rearrangement reaction was performed using benzylamine as a substrate.

Figure 48:
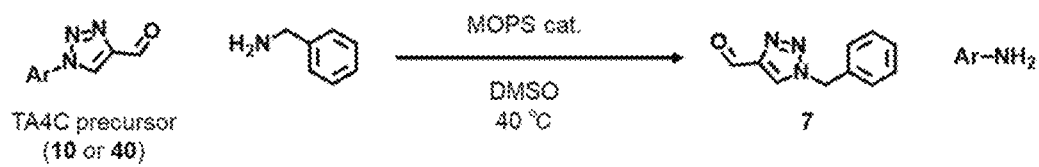
FIG. 48 shows the scheme of a Dimroth rearrangement reaction using compound 40 (Example 15-2).
Figures 49, 50:
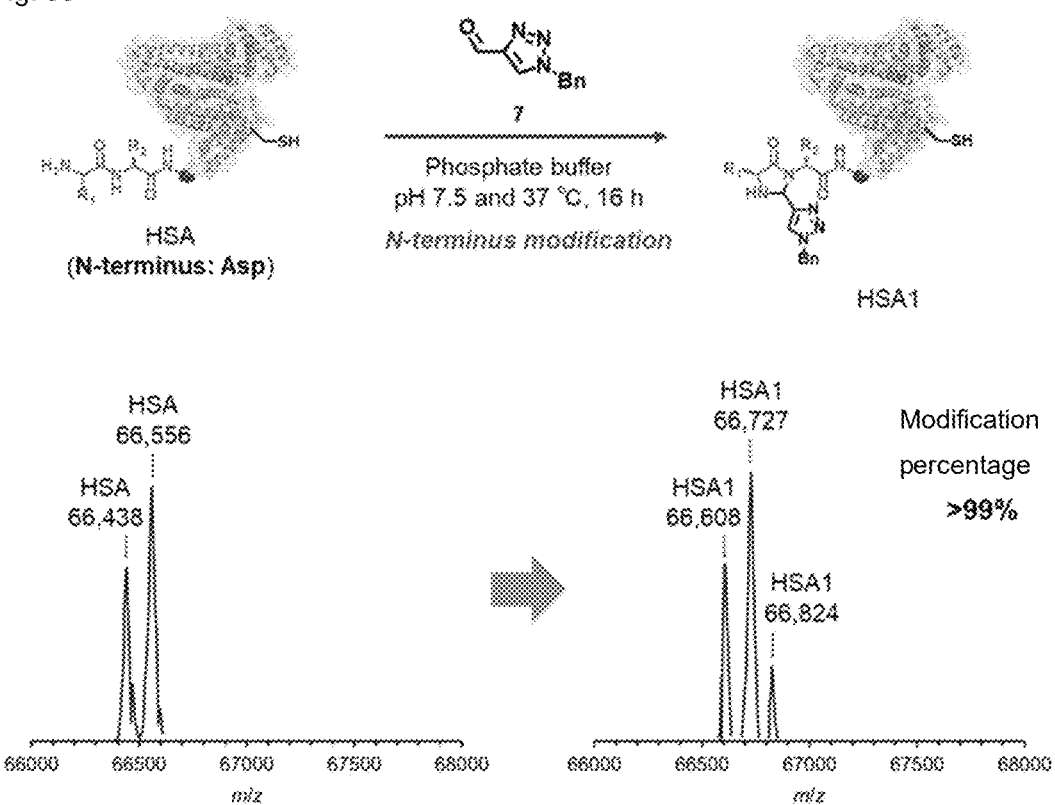
FIG. 49 shows the yields of compound 7 in a Dimroth rearrangement reaction (Example 15-2). The yields were calculated from ¹H NMR measurement.
FIG. 50 shows the reaction scheme and results of an N-terminal modification reaction of human serum-derived albumin (Example 16-2).

A solution of compound 40 in dimethyl sulfoxide (100 mM, 40 µL, 4 µmol) and an aqueous MOPS solution (200 mM, 2 µL, 10 mol %) were added to a solution of benzylamine in dimethyl sulfoxide (100 mM, 40 µL, 4 µmol), and the mixture was heated using a heat block at 40° C. for 12 hours. After air-cooling to mom temperature, the reaction mixture was diluted with deuterated dimethyl sulfoxide (310 µL). As an internal standard, a solution of 1,3,5-trimethoxybenzene in deuterated dimethyl sulfoxide (400 mM, 10 µL, 4 mol) was added, and $^1$H NMR measurement was performed. The yield was calculated from the integral value of the peak corresponding to the proton at the benzylic position of compound 7, which is a product, based on the integral value of the internal standard. FIG. 48 shows the scheme, and FIG. 49 shows the results.

The results reveal that the Dimroth rearrangement reaction proceeds in good yield at a low temperature when compound 40 is used, compared with the case in which compound 10 is used. This shows that the introduction of an electron-withdrawing substituent at the N1 position of the triazole ring contributes significantly to improvement of the reactivity with respect to the Dimroth rearrangement reaction.

Example 16. Protein N-Terminal Modification 2

An N-terminal modification reaction was performed for human serum-derived albumin (HSA), which is commonly used as a protein substrate.

16-1. Reagent, Solvent, Etc.

Human serum-derived albumin (HSA) was purchased from Merck. Ultrapure water used was obtained by purification with Millipore Integral 3. As other reagents and solvents, commercially available products were used as is. As HSA, a mixture with HSA that had already undergone modification in a living body was used. Modified HSA has been identified by a published report (A. Kawakami, K. Kubota, N. Yamada, U. Tagami, K Takehana, I. Sonaka, E. Suzuki, K. Hirayama, FEBS J., 2006, 273, 3346-3357.).

16-2. Protein Modification

This method targets the N-terminus of a protein. The protein that can be a target is one in which the N-terminal amino group is unmodified, and the second amino acid residue from the N-terminus is an amino acid other than proline. As a specific example, the N-terminal modification of human serum-derived albumin (HSA) is described below.

The following shows the amino acid sequence of HSA (PDB: 1AO6).

```
                                      (SEQ ID NO: 3)
DAHKSEVAHR FKDLGEENFK ALVLIAFAQY LQQCPFEDHV

KLVNEVTEFA KTCVADESAE NCDKSLHTLF GDKLCTVATL

RETYGEMADC CAKQEPERNE CFLQHKDDNP NLPRLVRPEV
```

```
DVMCTAFHDN EETFLKKYLY EIARRHPYFY APELLFFAKR

YKAAFTECCQ AADKAACLLP KLDELRDEGK ASSAKQRLKC

ASLQKFGERA FKAWAVARLS QRFPKAEFAE VSKLVTDLTK

VHTECCHGDL LECADDRADL AKYICENQDS ISSKLKECCE

KPLLEKSHCI AEVENDEMPA DLPSLAADFV ESKDVCKNYA

EAKDVFLGMF LYEYARRHPD YSVVLLLRLA KTYETTLEKC

CAAADPHECY AKVFDEFKPL VEEPQNLIKQ NCELFEQLGE

YKFQNALLVR YTKKVPQVST PTLVEVSRNL GKVGSKCCKH

EAKRMPCAE DYLSVVLNQL CVLHEKTPVS DRVTKCCTES

LVNRRPCFSA LEVDETYVPK EFNAETFTFH ADICTLSEKE

RQIKKQTALV ELVKHKPKAT KEQLKAVMDD FAAFVEKCCK

ADDKETCFAE EGKKLVAASQ AALGL.
```

Protein N-terminal modification was performed using compound 7 as a modifying agent and HSA as a target protein, by the same method as in Example 10-2. FIG. 50 shows the results of LC/MS analysis of the product. The modified protein is referred to as "HSA1." The modification percentage under this reaction condition was calculated as 99% or more. The product after the reaction was purified by size exclusion chromatography, as necessary.

Example 17. Double Modification of Protein Targeting Protein N-Terminus and Cysteine Residue 17-1. Reagent, Solvent, Etc.

The equipment, reagents, solvents, etc., used were similar to those in Example 16.

17-2. Cysteine Residue Modification in Protein

Cysteine residue modification in a protein was performed with reference to a published report (X. Chen, H. Wu, C.-M. Park, T. H. Poole, G. Keceli, N. O. Devarie-Baez, A. W. Tsang, W. T. Lowther, L. B. Poole, S. B. King, M. Xian, C. M. Furdui, ACS Chem. Biol., 2017, 12, 2201-2208). The specific experimental procedure is described below.

Figure 51:
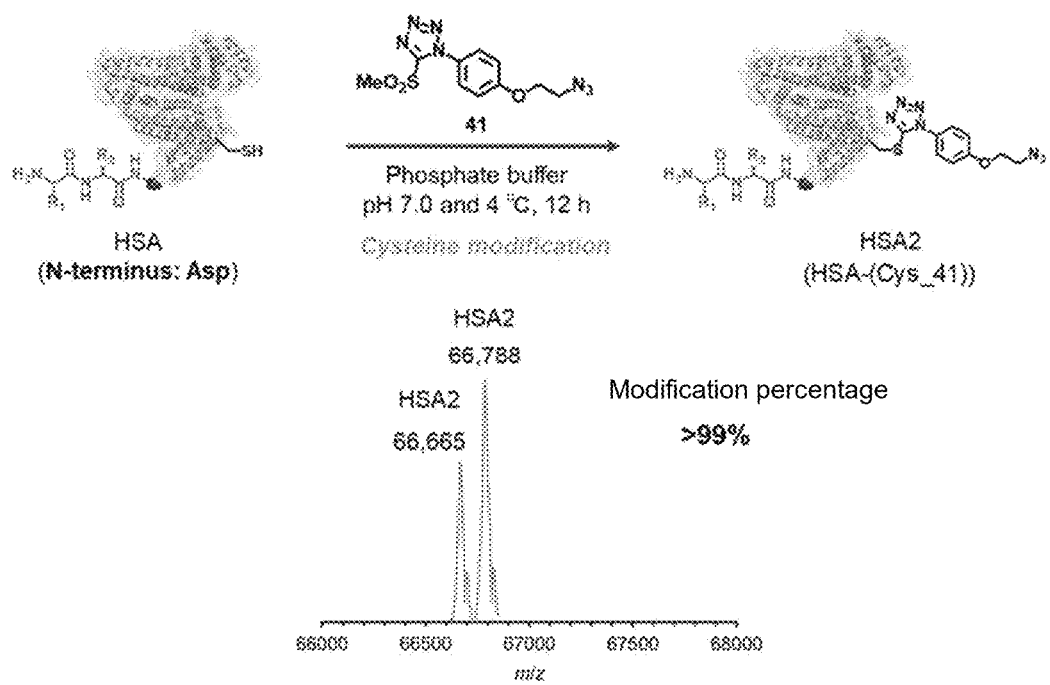
FIG. 51 shows the reaction scheme and results of cysteine residue modification of human serum-derived albumin (Example 17-2).

A solution of compound 41 in a mixture of DMSO/water (1:1) (25 mM, 40 µL, 1 µmol, final concentration: 500 µM) was diluted with a phosphate buffer (100 mM, pH 7.0, 1.86 mL). A solution of HSA in ultrapure water (1 mM, 100 µL, 100 nmol, final concentration: 50 µM) was added thereto, and the mixture was left to stand at 4° C. for 12 hours. After the reaction, modification evaluation using LC/MS was performed. FIG. 51 shows the results. The modified protein is referral to as "HSA2." The modification percentage under this reaction condition was calculated as 99% or more. The product after the reaction was purified by size exclusion chromatography as necessary.

17-3. N-Terminal Modification of Protein in which Cysteine Residue is Modified

Figure 52:
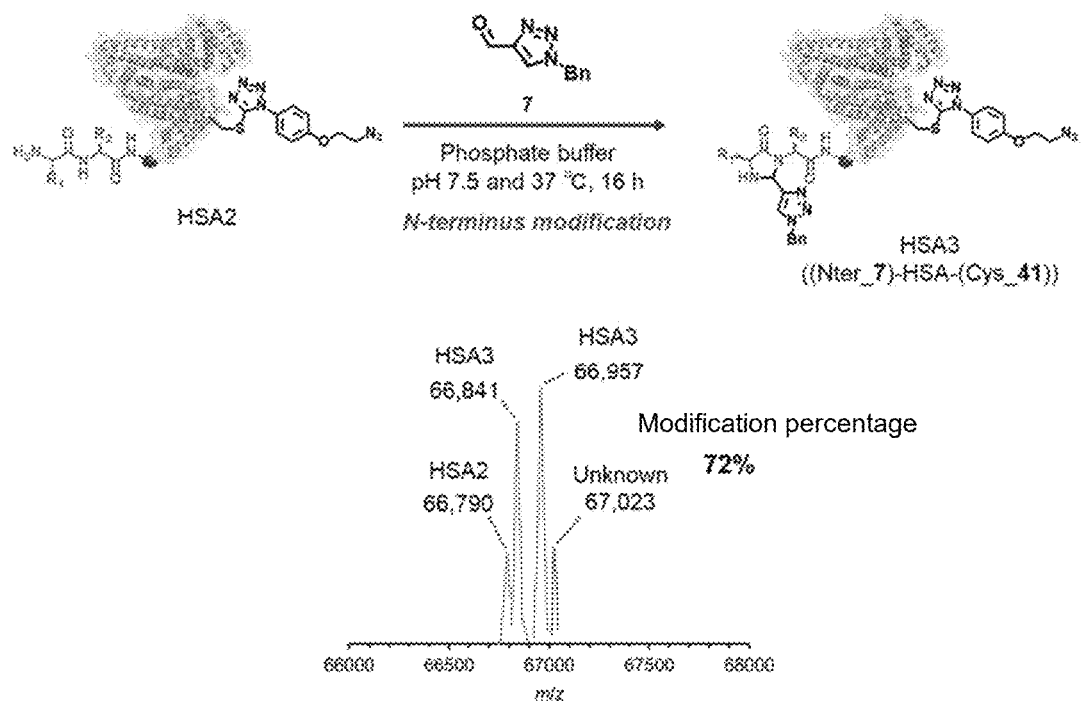
FIG. 52 shows the reaction scheme and results of N-terminal modification of human serum-derived albumin in which a cysteine residue is modified (Example 17-3).

Modification of the N-terminus of the protein was performed using compound 7 for HSA2, which was prepared in Example 17-2. FIG. 52 shows the scheme and results.

A solution of compound 7 in dimethyl sulfoxide (DMSO) (200 mM, 1 µL final concentration: 10 mM) was added to a phosphate buffer solution containing HSA2 (HSA2 concentration: 200 µM, final concentration: 50 µM, buffer solution concentration: 10 mM, pH 7.5, 19 µL), and the mixture was shaken at 37° C. for 16 hours. The modified protein is referred to as "HSA3." The modification percentage under this reaction condition was calculated as 72%.

Example 18. Stability of Protein Modified at N-Terminus 18-1. Reagent, Solvent, Etc.

The equipment, reagents, solvents, etc. used were similar to those in Example 10.

18-2. Stability of Modified Protein Over Time

Figure 53:
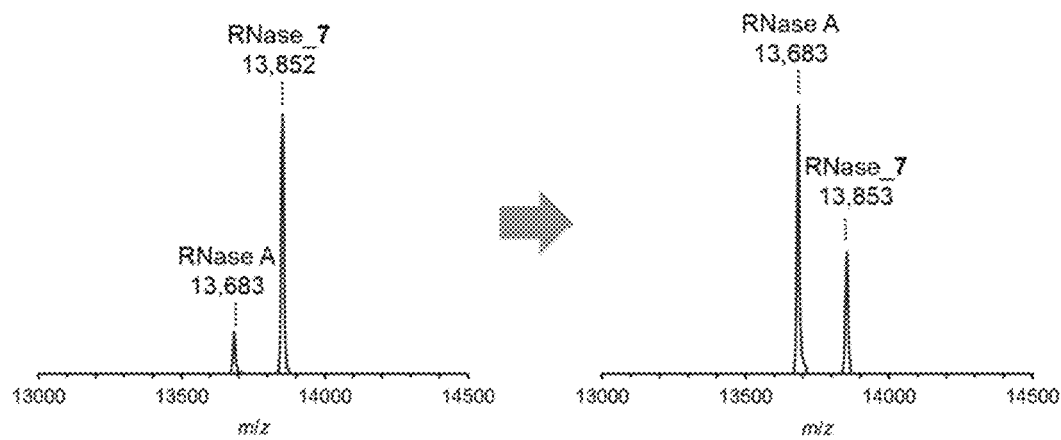
FIG. 53 shows the results of LC/MS analysis of an RNase_7 solution after being left to stand for 24 hours (Example 18-2).

A phosphate buffer containing RNase_7 (RNase_7 concentration: 100 µM, final concentration: 10 µM, buffer solution concentration: 100 µM, pH 7.0, 10 µL) was diluted with a phosphate buffer (100 mL, pH 7.0, 90 µL), and left to stand at 37° C. for 12 hours, 24 hours, and 48 hours. As an example, FIG. 53 shows the results of LC/MS analysis after being left to stand for 24 hours.

Figure 54:
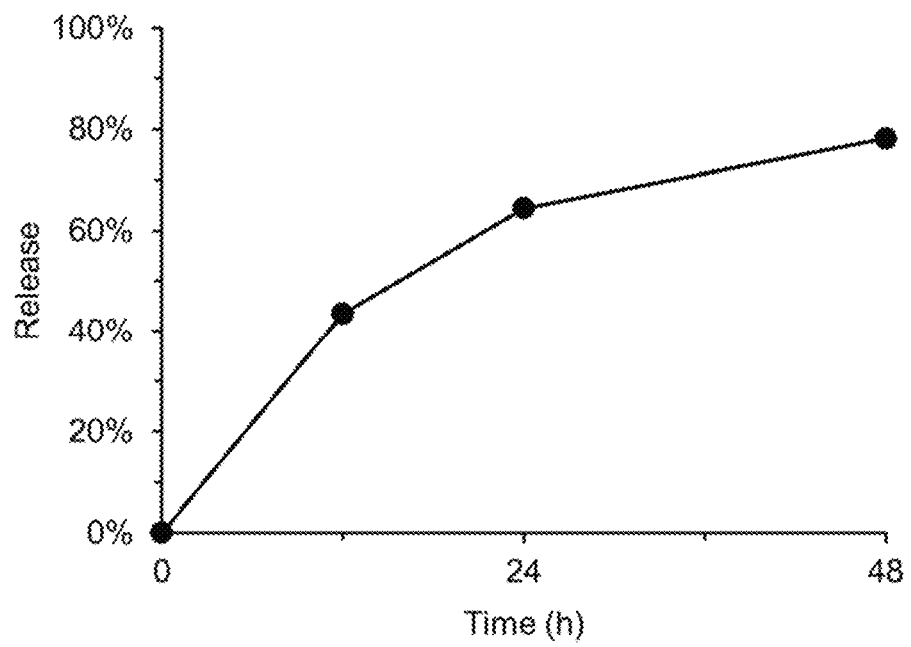
FIG. 54 shows the change in the release of a modifying agent over time in RNase_7 (Example 18-2).

This modification reaction, which involves the formation of a 4-imidazolidinone ring at the N-terminus, is equilibrium reaction. From the results of LC/MS analysis, it is considered that the unmodified protein and the modifying agent are regenerated by hydrolysis of the 4-imidazolidinone ring, which is the reverse reaction, in the protein modified at the N-terminus. FIG. 54 shows a graph in which the vertical axis shows the release (=1−(modified RNase after being left to stand/total RNase amount)/(modified RNase before being left to stand/total RNase amount)) calculated from the peak intensity in the mass spectrum; and the horizontal axis shows the time when the RNase was left to stand.

18-3. Stability of Modified Protein with pH Change

Figure 55:
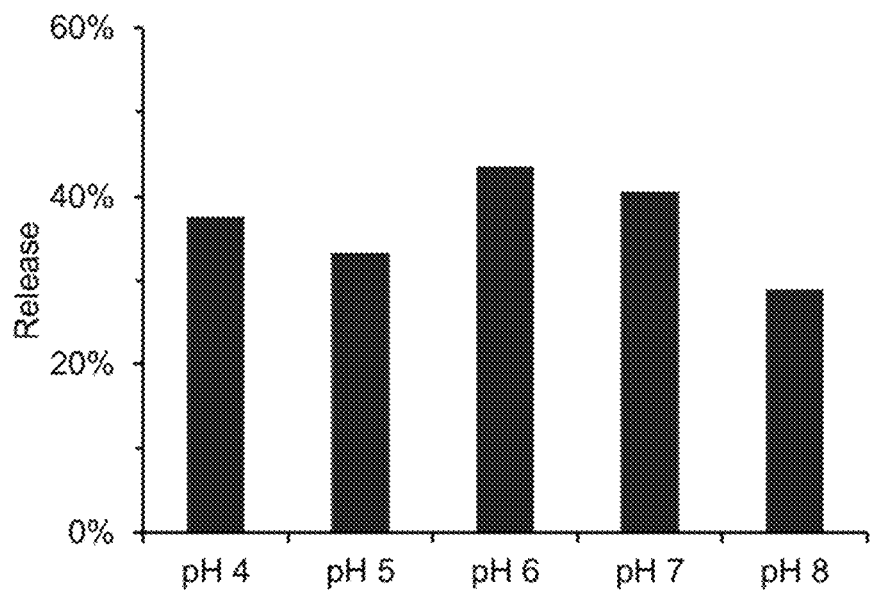
FIG. 55 shows the change in the release of a modifying agent with the pH change in RNase_7 (Example 18-3).

A phosphate buffer containing RNase_7 (RNase_7 concentration: 100 µM, final concentration: 10 µM, buffer solution concentration: 100 mM, pH 7.0, 10 µL) was diluted with a buffer (100 mL, 90 µL) so that the pH was 4, 5, 6, 7, and 8, and left to stand at 37° C. for 12 hours. The dilution was performed using an acetate buffer for conditions of a pH of 4 and 5, and a phosphate buffer for conditions of a pH of 6, 7, and 8. FIG. 55 shows the results of the release.

Example 19. Compound Synthesis 8 (Synthesis of Triazolecarbaldehyde with Substituents at the 1- and 5-Positions)

As the reagents and solvents used for the synthesis, commercially available products were used as is. The azide compound, alkyne compound, and boronic acid pinacol ester used as precursors were synthesized with reference to published reports (L. S. C.-Verduyn, L. Mirfeizi, R. A. Dierckx, P. H. Elsinga, B. L. Feringa, Chem. Commun., 2009, 16, 2139-2140; E. Jahnke, J. Weiss, S. Neuhaus, T. N. Hoheisel H. Frauenrath, Chem. Eur. J., 2009, 15, 388-404; J. C. Pieck, D. Kuch, F. Grolle, U. Linne, C. Haas, T. Cargill, J. Am. Chem. Soc., 2006, 128, 1404-1405; J. Schmidt, M. Rotter, T. Weiser, S. Wittmann, L. Weizel, A. Kaiser, J. Heering, T. Goebel, C. Angioni, M. Wurglics, A. Paulke, G. Geisslinger, A. Kahnt, D. Steinhilber, E. Proschak, D. Merk, J. Med. Chem., 2017, 60, 7703-7724; and JR. White, G. J. Price, S.

Schiffers, P. R. Raithby, P. K. Plucinski, C. G. Frost, Tetrahedron Letters, 2010, 51, 3913-3917).

19-1. Synthesis of 1-Benzyl-5-Phenyl-1H-1,2,3-Triazole-4-Carbaldehyde (44)

Compound 44 was synthesized according to the following scheme, with reference to published reports (K. Yamamoto, T. Bruun, J. Y. Kim, L Zhang, M. Lautens, Org. Lett., 2016, 18, 2644-2647; and J. Deng, Y.-M. Wu, Q.-Y. Chen, Synthesis, 2005, 16, 2730-2738).

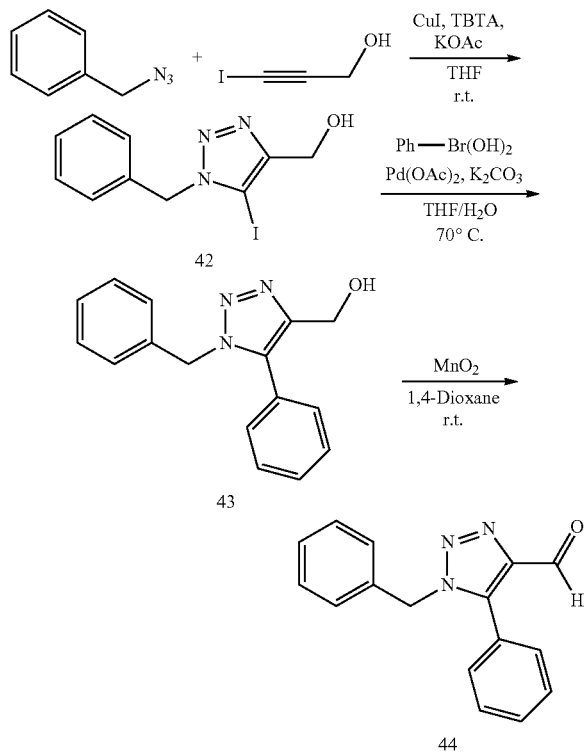

19-1-1. Synthesis of (1-Benzyl-5-Iodo-1H-1,2,3-Triazol-4-Yl)Methanol (42)

Figure 56:
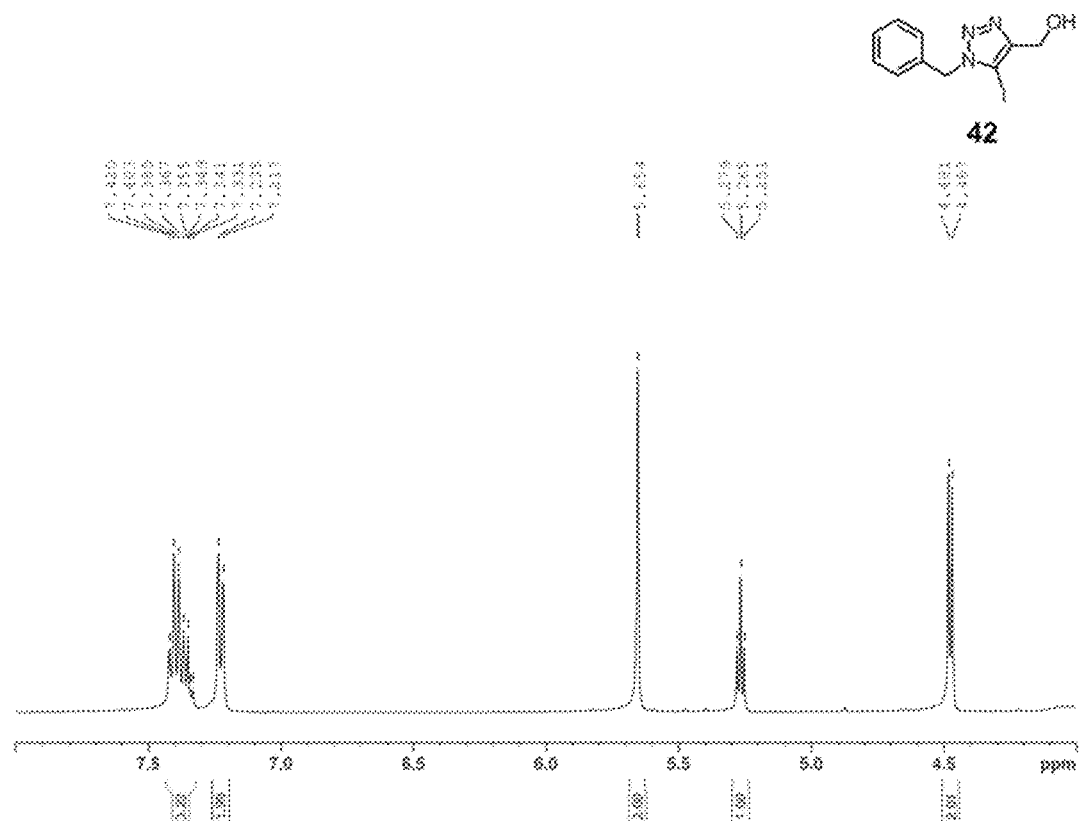
FIG. 56 shows the ¹H NMR spectrum (400 MHz, DMSO-d₆) of compound 42.

THF (89 mL) was added to a mixture of benzyl azide (0.67 g, 5.0 mmol), 3-iodoprop-2-yn-1-ol (0.91 g, 5.0 mmol), copper (I) iodide (95 mg, 0.50 mmol), TBTA (0.27 g, 0.50 mmol), and potassium acetate (1.5 g, 15 mmol) under a nitrogen atmosphere, and the mixture was stirred at mom temperature overnight. The solvent of the reaction mixture was distilled off under reduced pressure, and dilution was performed with water (30 mL) and ethyl acetate (30 mL), followed by extraction with ethyl acetate (30 mL×3). The resulting organic layer was washed with saturated saline (30 mL x 2) and dried over sodium sulfate, and the solvents of the filtrate obtained by filtration were distilled off under reduced pressure. The residue was purified by silica gel column chromatography (hexane:ethyl acetate) to give compound 42 (white solid). FIG. 56 shows the $^1$H NMR spectrum.

Yield 82%: $^1$H NMR (400 MHz, DMSO-$d_6$): δ, 7.42-7.33 (m, 3H), 7.24-7.22 (m, 2H), 5.65; (s, 2H), 5.27 (t, J=5.6 Hz, 1H), 4.47 (d, J=5.6 Hz, 2H): $^{13}$C NMR (100 MHz, DMSO-$d_6$): δ, 151.30, 135.52, 128.89, 128.20, 127.54, 83.79, 54.99, 53.25; ESI-TOF MS (positive mode) m/z calcd. for $C_{10}H_{10}IN_3NaO$ [M+Na]$^+$ 337.976, found 337.977.

19-1-2. Synthesis of (1-Benzyl-5-Phenyl-1H-1,2,3-Triazol-4-Yl)Methanol (43)

Figure 57:
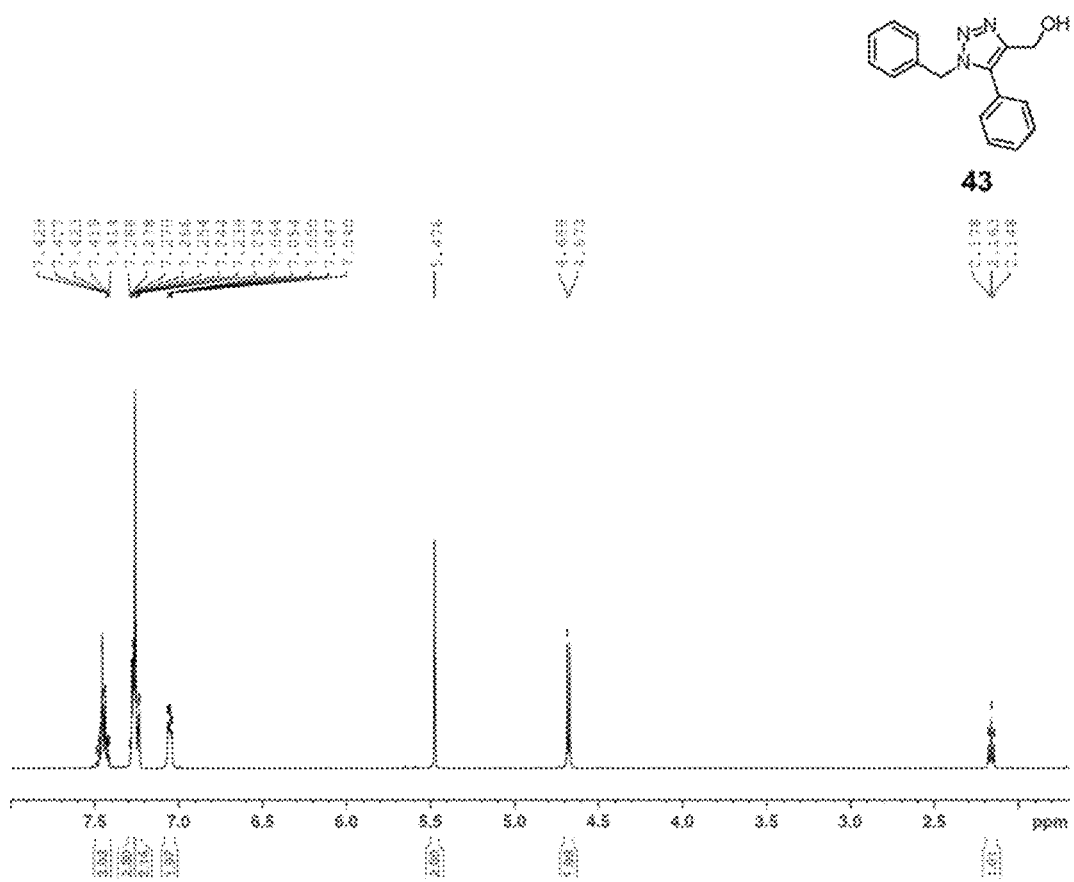
FIG. 57 shows the ¹H NMR spectrum (400 MHz, CDCl₃) of compound 43.

Pure water (2.4 mL) was added to a mixture of compound 42 (0.24 g, 0.75 mmol), phenylboronic acid (0.18 g, 1.5 mmol), potassium carbonate (0.21 g, 1.5 mmol), and palladium acetate (17 mg, 0.075 mmol). Thereafter, THF (9.6 mL) was added under a nitrogen atmosphere, and the mixture was stirred at 70° C. overnight. The solvents of the reaction mixture were distilled off under reduced pressure, and dilution was performed with water (30 mL) and ethyl acetate (30 mL), followed by extraction with ethyl acetate (30 mL×3). The resulting organic layer was washed with saturated saline (30 mL×2) and dried over sodium sulfate, and the solvents of the filtrate obtained after filtration were distilled off under reduced pressure. The residue was purified by flash column chromatography (hexane:ethyl acetate) to give compound 43 (light-yellow solid). FIG. 57 shows the $^1$H NMR spectrum.

Yield 54%: $^1$H NMR (400 MHz, CDCl$_3$): δ, 7.49-7.42 (m, 3H), 7.29-7.23 (m, 5H), 7.06-7.04 (m, 2H), 5.48 (s, 2H), 4.68 (d, J=6.0 Hz, 2H), 2.16 (t, J=6.0 Hz, 1H): ESI-TOF MS (positive mode) m/z calcd. for $C_{16}H_{15}N_3NO$ [M+Na]$^+$ 288.111, found 288.112.

19-1-3. Synthesis of 1-Benzyl-5-Phenyl-1H-1,2,3-Triazole-4-Carbaldehyde (44)

Figure 58:
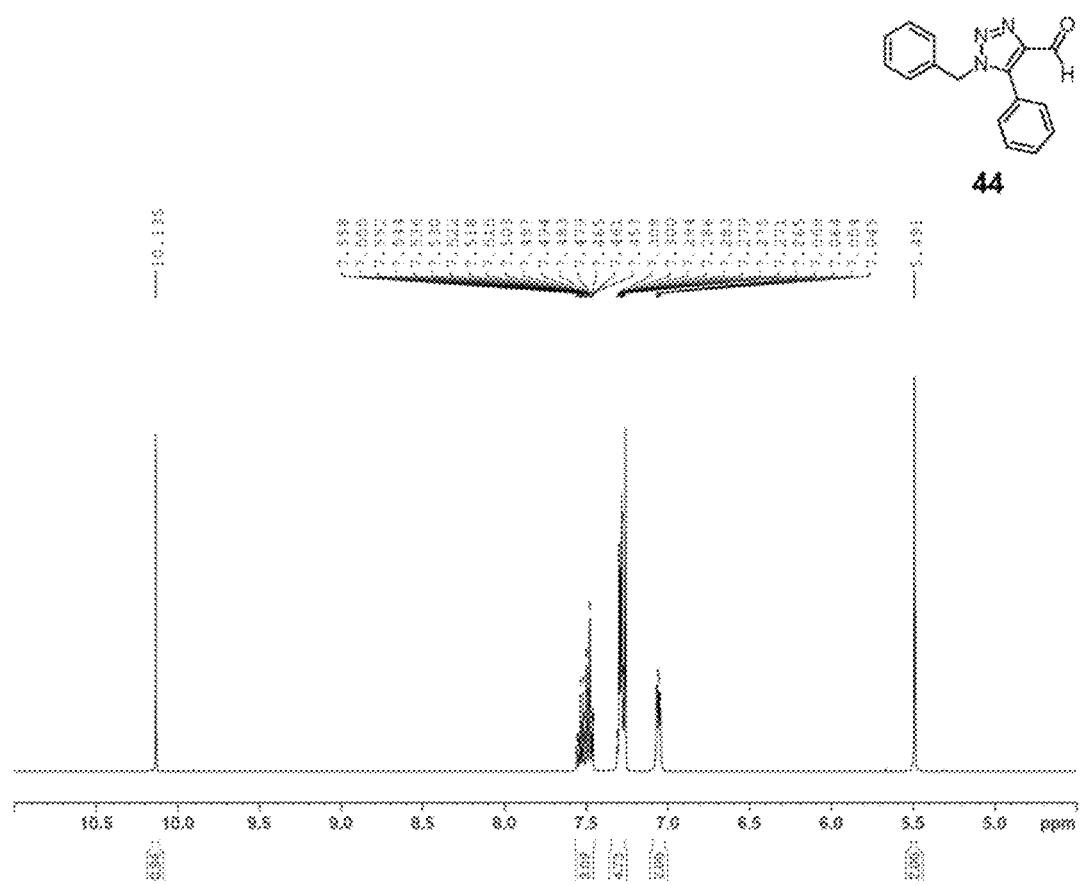
FIG. 58 shows the ¹H NMR spectrum (400 MHz, CDCl₃) of compound 44.

Activated manganese dioxide (163 mg, 1.9 mmol) was added to a solution (10 mL) of compound 43 (50 mg, 0.19 mmol) in 1,4-dioxane, and the mixture was stirred at mom temperature overnight. The reaction mixture was filtered, and the solvent of the resulting filtrate was distilled off under reduced pressure. Thereafter, the resulting crude product was purified by flash column chromatography (hexane:ethyl acetate) to give compound 44 (oil). FIG. 58 shows the $^1$H NMR spectrum.

Yield 91%: $^1$H NMR (400 MHz, CDCl$_3$): δ, 10.14 (s, 1H), 7.56-7.46 (m, 3H), 7.31-7.27 (m, 5H), 7.07-7.05 (m, 2H), 5.49 (s, 2H): ESI-TOF MS (positive mode) m/z calcd. for $C_{16}H_{13}NaN_3O$ [M+Na]$^+$ 286.095, found 286.093.

19-1-4. Synthesis of (1-Benzyl-5-(4-Methoxyphenyl)-1H-1,2,3-Triazol-4-Yl)Methanol (45)

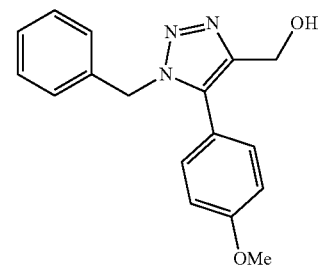

Figure 59:
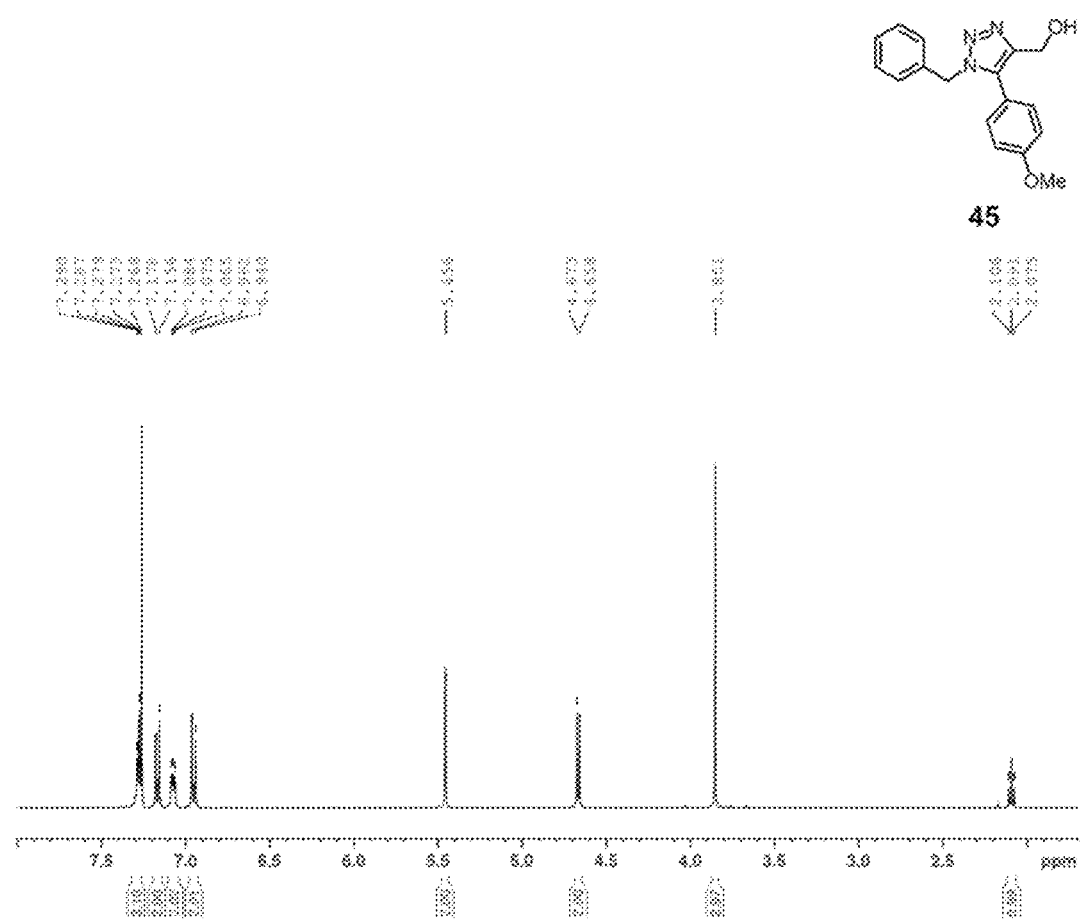
FIG. 59 shows the ¹H NMR spectrum (400 MHz, CDCl₃) of compound 45.

Compound 45 (light-yellow solid) was synthesized using 4-methoxyphenylboronic acid as a precursor by the same method as in Example 19-1-2. FIG. 59 shows the $^1$H NMR spectrum.

Yield 97%: $^1$H NMR (400 MHz, CDCl$_3$): δ, 7.29-7.27 (m, 3H), 7.17 (d, J=8.8 Hz, 2H), 7.08-7.07 (m, 2H), 6.95 (d, J=8.8 Hz, 2H), 5.46 (s, 2H), 4.67 (d, J=6.0 Hz, 2H), 3.85 (s, 3H), 2.09 (t, J=6.0 Hz, 1H): $^{13}$C NMR (100 MHz, CDCl$_3$): δ, 160.75, 144.90, 135.95, 135.63, 131.16, 128.95, 128.32, 127.43, 118.45, 114.62, 56.09, 55.53, 52.07; ESI-TOF MS (positive mode) m/z calcd. for C$_{17}$H$_{17}$N$_3$NaO$_2$ [M+Na]$^+$ 318.121, found 318.121.

19-1-5. Synthesis of 1-Benzyl-5-(4-Methoxyphenyl)-1H-1,2,3-Triazole-4-Carbaldehyde (46)

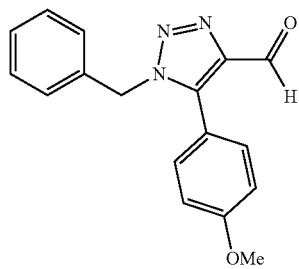

46

Figure 60:
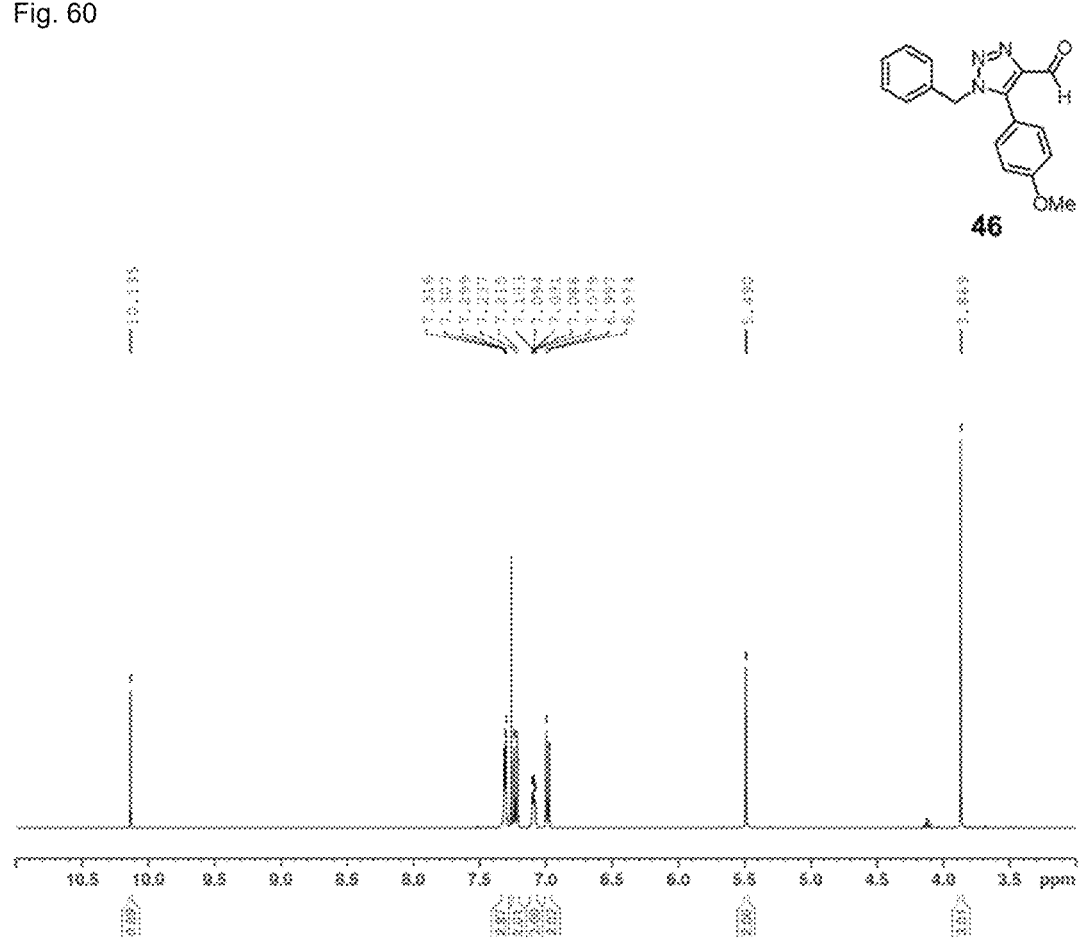
FIG. 60 shows the ¹H NMR spectrum (400 MHz, CDCl₃) of compound 46.

Compound 46 (oil) was synthesized using compound 45 as a precursor by the same method as in Example 19-1-3. FIG. 60 shows the $^1$H NMR spectrum.

Yield 91%: $^1$H NMR (400 MHz, CDCl$_3$): δ, 10.14 (s, 1H), 7.32-7.30 (m, 3H), 7.23 (d, J=8.8 Hz, 2H), 7.10-7.08 (m, 2H), 6.99 (d, J=8.8 Hz, 2H), 5.49 (s, 2H), 3.87 (s, 3H): $^{13}$C NMR (100 MHz, CDCl$_3$): δ, 184.68, 161.42, 143.49, 140.76, 134.72, 131.23, 129.04, 128.59, 127.44, 116.48, 114.54, 55.49, 51.85: ESI-TOF MS (positive mode) m/z calcd. for C$_{17}$H$_{15}$N$_3$NaO$_2$ [M+Na]$^+$ 316.106, found 316.104.

19-1-6. Synthesis of (1-Benzyl-5-(4-Nitrophenyl)-1H-1,2,3-Triazol-4-Yl)Methanol (47)

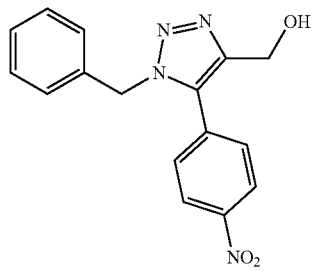

47

Figure 61:
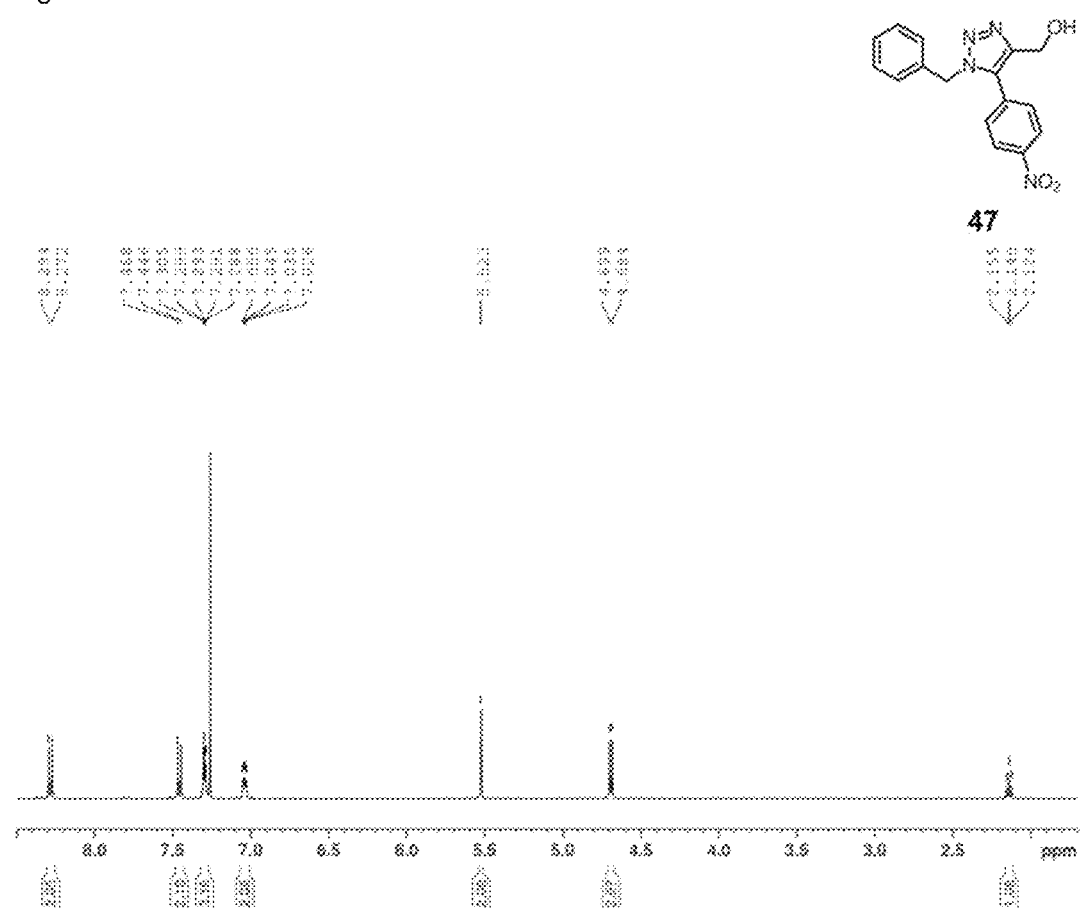
FIG. 61 shows the ¹H NMR spectrum (400 MHz, CDCl₃) of compound 47.

Compound 47 (brown solid) was synthesized using 4-nitrophenylboronic acid as a precursor by the same method as in Example 19-1-2. FIG. 61 shows the $^1$H NMR spectrum.

Yield 58%: $^1$H NMR (400 MHz, CDCl$_3$): δ, 8.28 (d, J=8.8 Hz, 2H), 7.46 (d, J=8.8 Hz, 2H), 7.31-7.29 (m, 3H), 7.05-7.03 (m, 2H), 5.52 (s, 2H), 4.69 (d, J=6.0 Hz, 2H), 2.14 (t, J=6.0 Hz, 1H): $^{13}$C NMR (100 MHz, CDCl$_3$): δ, 148.56, 145.90, 134.85, 134.12, 133.18, 130.84, 129.22, 128.77, 127.25, 124.22, 55.83, 52.74: ESI-TOF MS (positive mode) m/z calcd. for C$_{16}$H$_{14}$N$_4$NaO$_3$ [M+Na]$^+$ 333.096, found 333.095.

19-1-7. Synthesis of 1-Benzyl-5-(4-Nitrophenyl)-1H-1,2,3-Triazole-4-Carbaldehyde (48)

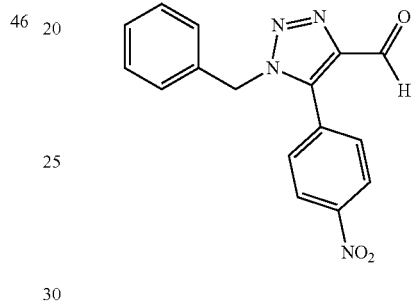

48

Figure 62:
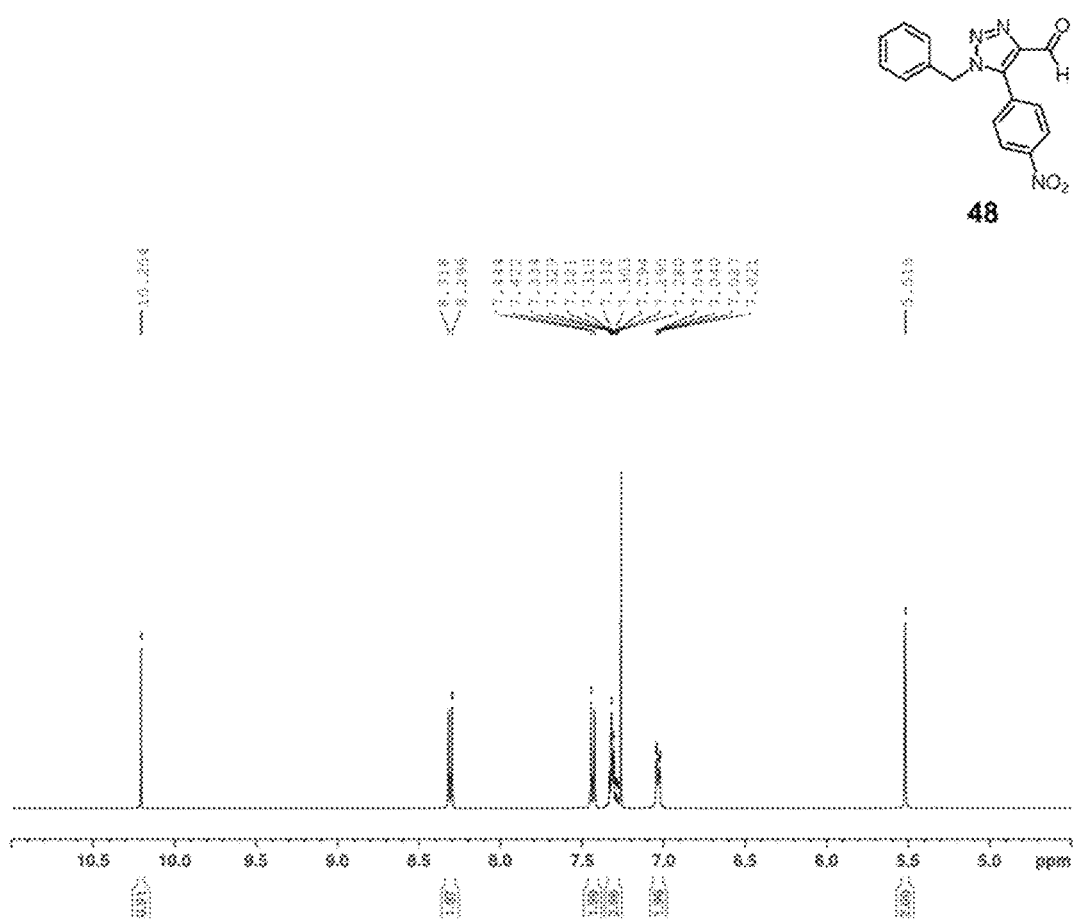
FIG. 62 shows the ¹H NMR spectrum (400 MHz, CDCl₃) of compound 48.

Compound 48 (yellow solid) was synthesized using compound 47 as a precursor by the same method as in Example 19-1-3. FIG. 62 shows the $^1$H NMR spectrum.

Yield 93%: $^1$H NMR (400 MHz, CDCl$_3$): δ, 10.20 (s, 1H), 8.31 (d, J=8.8 Hz, 2H), 7.43 (d, J=8.8 Hz, 2H), 7.33-7.28 (m, 3H), 7.04-7.02 (m, 2H), 5.52 (s, 2H): $^{13}$C NMR (100 MHz, CDCl$_3$): δ, 185.02, 149.11, 144.27, 137.67, 133.99, 131.05, 129.37, 129.15, 127.45, 124.07, 52.64: ESI-TOF MS (positive mode) m/z calcd. for C$_{16}$H$_{12}$N$_4$NaO$_3$ [M+Na]$^+$ 331.080, found 331.082.

19-1-8. Synthesis of 1-(4((4-(hydroxymethyl)-5-iodo-1H-1,2,3-triazol-1-yl)methyl)phenyl)ethan-1-one (49)

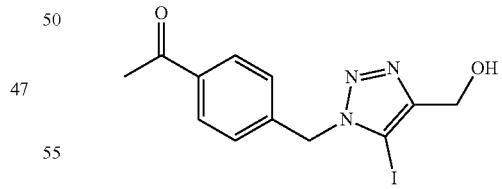

49

Figure 63:
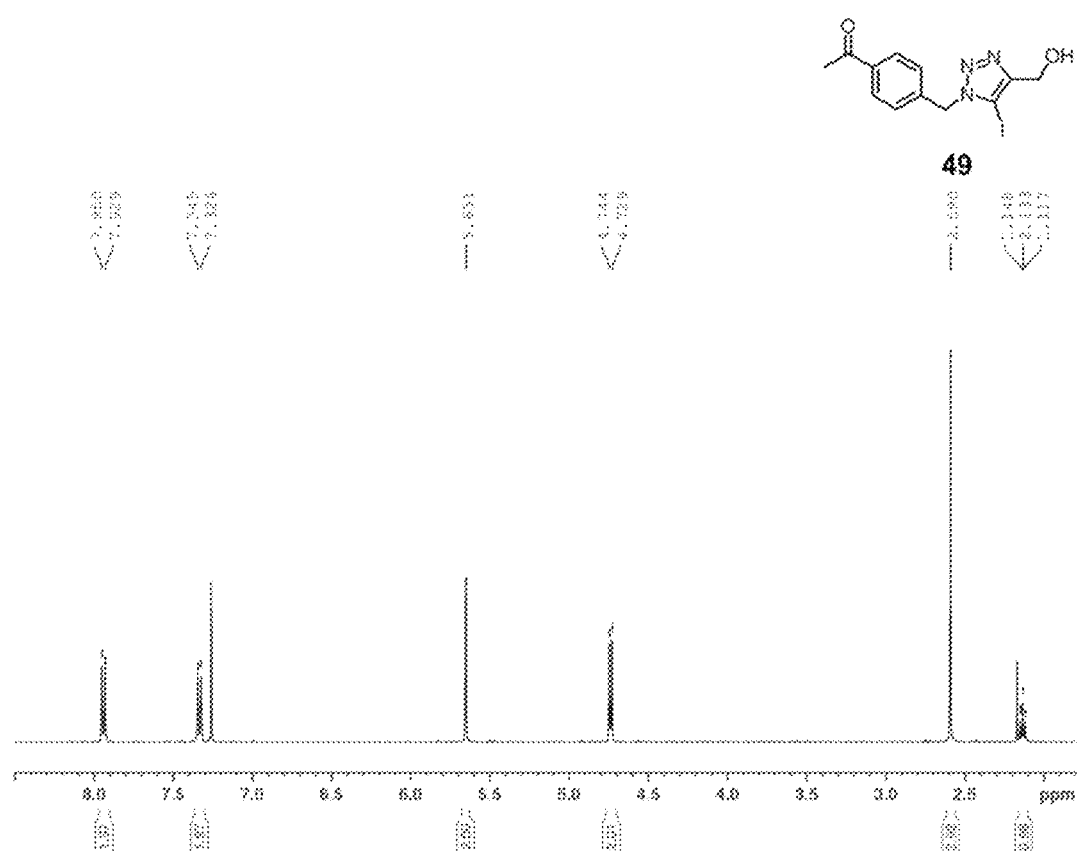
FIG. 63 shows the ¹H NMR spectrum (400 MHz, CDCl₃) of compound 49.

Compound 49 (white solid) was synthesized using 1-(4-(azidomethyl)phenyl)ethan-1-one as a precursor by the same method as in Example 19-1-1. FIG. 63 shows the $^1$H NMR spectrum.

Yield 40%: $^1$H NMR (400 MHz, CDCl3): δ, 7.94 (d, J=8.3 Hz, 2H), 7.33 (d, J=8.3 Hz, 2H), 5.65 (s, 2H), 4.74 (s, 2H), 2.59 (s, 3H), 2.15; (s, 3H); $^{13}$C NMR (100 MHz, CDCl$_3$): δ, 197.5, 151.5, 139.1, 137.4, 129.1, 128.1, 78.9, 56.8, 53.9, 26.8: ESI-TOF MS (positive mode) m/z calcd. for C$_{12}$H$_{12}$IN$_3$NaO$_2$ [M+Na]$^+$ 379.987, found 379.987.

19-1-9. Synthesis of 1-(4-((5-(4-(Azidomethyl)Phenyl)-4-(Hydroxymethyl)-1H-1,2,3-Triazol-1-Yl)Methyl)Phenyl)Ethan-1-One (50)

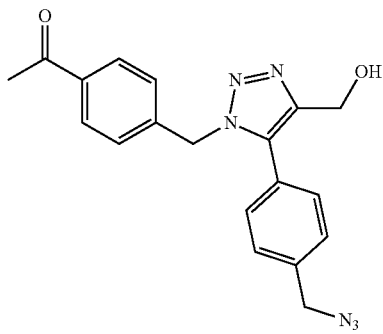

Figure 64:
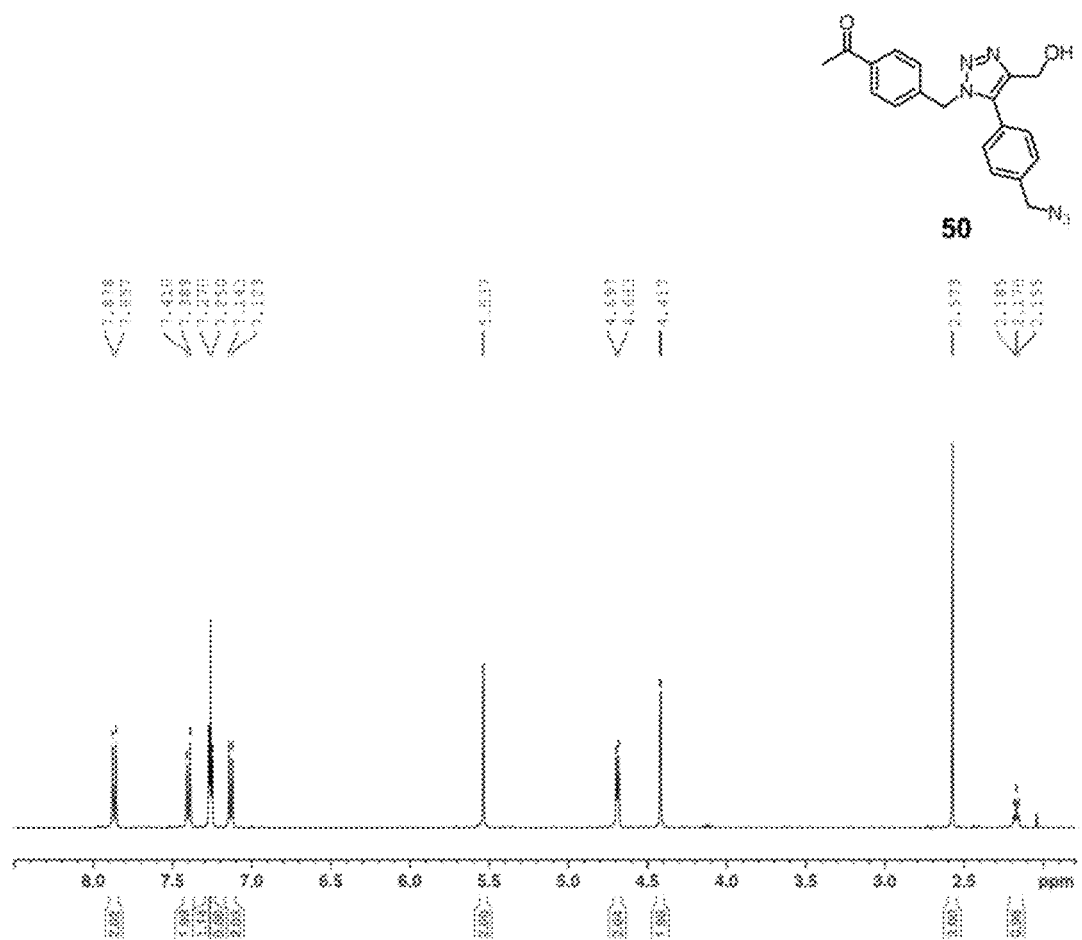
FIG. 64 shows the ¹H NMR spectrum (400 MHz, CDCl₃) of compound 50.

Compound 50 (light-yellow solid) was synthesized using compound 49 and 2-(4-(azidomethyl)phenyl)-4,4,5,5-tetramethyl-1,3,2-dioxaborolane as precursors by the same method as in Example 19-1-2. FIG. 64 shows the $^1$H NMR spectrum.

Yield 71%: $^1$H NMR (400 MHz, CDCl$_3$): δ, 7.87 (d, J=8.0 Hz, 2H), 7.40 (d, J=8.0 Hz, 2H), 7.26 (d, J=8.0 Hz, 2H), 7.13 (d, J=8.0 Hz, 2H), 5.54 (s, 2H), 4.69 (d, J=5.8 Hz, 2H), 4.42 (s, 2H), 2.57 (s, 3H), 2.17 (t, J=5.8 Hz, 1H); $^{13}$C NMR (100 MHz, CDCl$_3$): δ, 197.5, 145.4, 140.3, 137.5, 137.1, 135.6, 130.2, 129.1, 128.9, 127.5, 126.3, 55.9, 54.4, 51.9, 26.8; ESI-TOF MS (positive mode) m/z calcd. for C$_{19}$H$_{18}$N$_6$NaO$_2$ [M+Na]$^+$ 385.138, found 385.138.

19-1-10. Synthesis of 1-(4-Acetylbenzyl)-5-(4-(Azidomethyl)Phenyl)-1H-1,2,3-Triazole-4-Carbaldehyde (51)

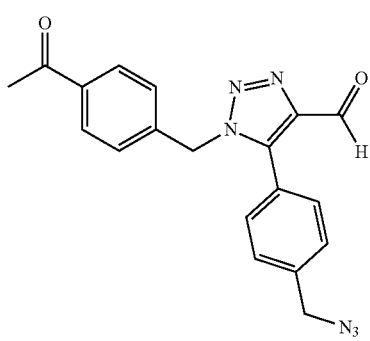

Figure 65:
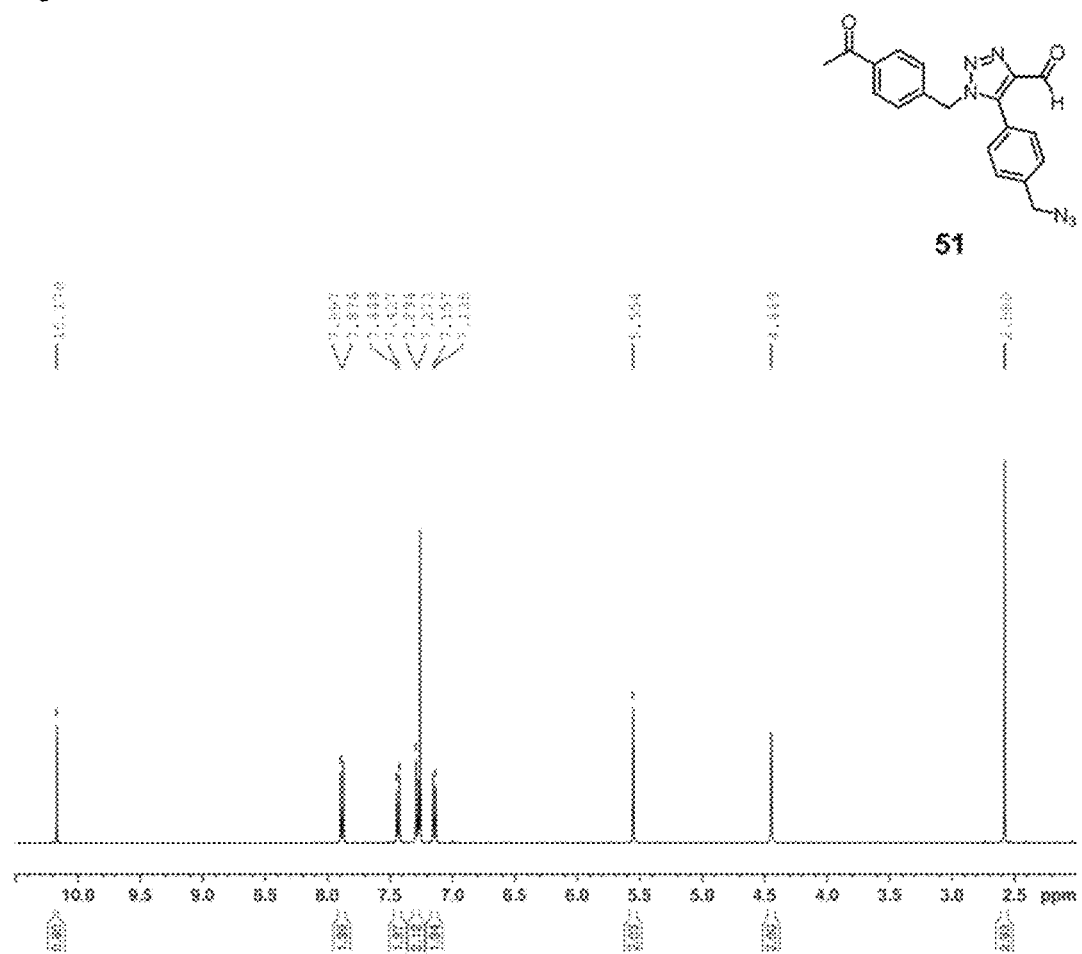
FIG. 65 shows the ¹H NMR spectrum (400 MHz, CDCl₃) of compound 51.

Compound 51 (clear, oil) was synthesized using compound 50 as a precursor by the same method as in Example 19-1-3. FIG. 65 shows the $^1$H NMR spectrum.

Yield 85%: $^1$H NMR (400 MHz, CDCl$_3$): δ, 10.17 (s, 1H), 7.88 (d, J=8.0 Hz, 2H), 7.44 (d, J=8.0 Hz, 2H), 7.28 (d, J=8.0 Hz, 2H), 7.14 (d, J=8.0 Hz, 2H), 5.55 (s, 2H), 4.45 (s, 2H), 2.58 (s, 3H); $^{13}$C NMR (100 MHz, CDCl3): δ, 197.4, 184.7, 143.9, 140.0, 139.3, 138.6, 137.4, 130.1, 129.1, 128.7, 127.7, 124.6, 54.3, 51.7, 26.8: ESI-TOF MS (positive mode) m/z calcd. for C$_{19}$H$_{16}$N$_6$NaO$_2$ [M+Na]$^+$ 383.123, found 383.123.

Example 20. Peptide N-Terminal Modification 3

Modification of the N-terminus of a peptide was performed with reference to a published report (J. I. MacDonald, H. K. Munch, T. Moore, M. B. Francis, Nat. Chem. Biol. 2015, 11, 326-331). The specific experimental procedure is described below.

Figure 66:
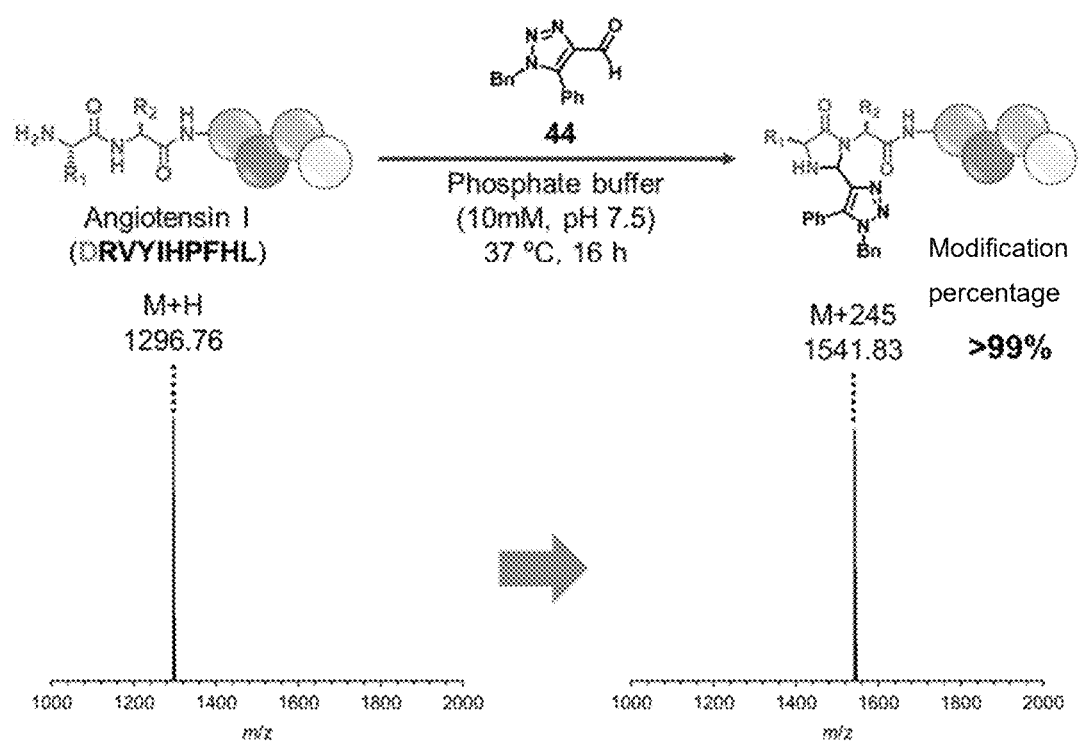
FIG. 66 shows the reaction scheme and results of N-terminal modification of angiotensin I (Example 20).

A solution of compound 44 in dimethyl sulfoxide (DMSO) (200 mM, 2 μL, 0.4 nmol, final concentration: 10 mM) was diluted with a phosphate buffer (10 mM, pH 7.5, 34 μL). An aqueous peptide solution (1 mM, 4 μL, 4 nmol, final concentration: 100 μM) was added thereto, and the mixture was shaken at 37° C. for 16 hours. The modification percentage (=(modified peptide amount)/(total peptide amount)) was evaluated from the peak intensity in a mass spectrum by using LC/MS. FIG. 66 shows the results. The modification percentage under this reaction condition was calculated as >99%.

Example 21. Protein N-Terminal Modification 4

Protein N-terminal modification was performed with reference to a published report (J. I. MacDonald, H. K. Munch, T. Moore, M. B. Francis, Nat. Chem. Biol. 2015, 11, 326-331). The specific experimental procedure is described below.

Figure 67:
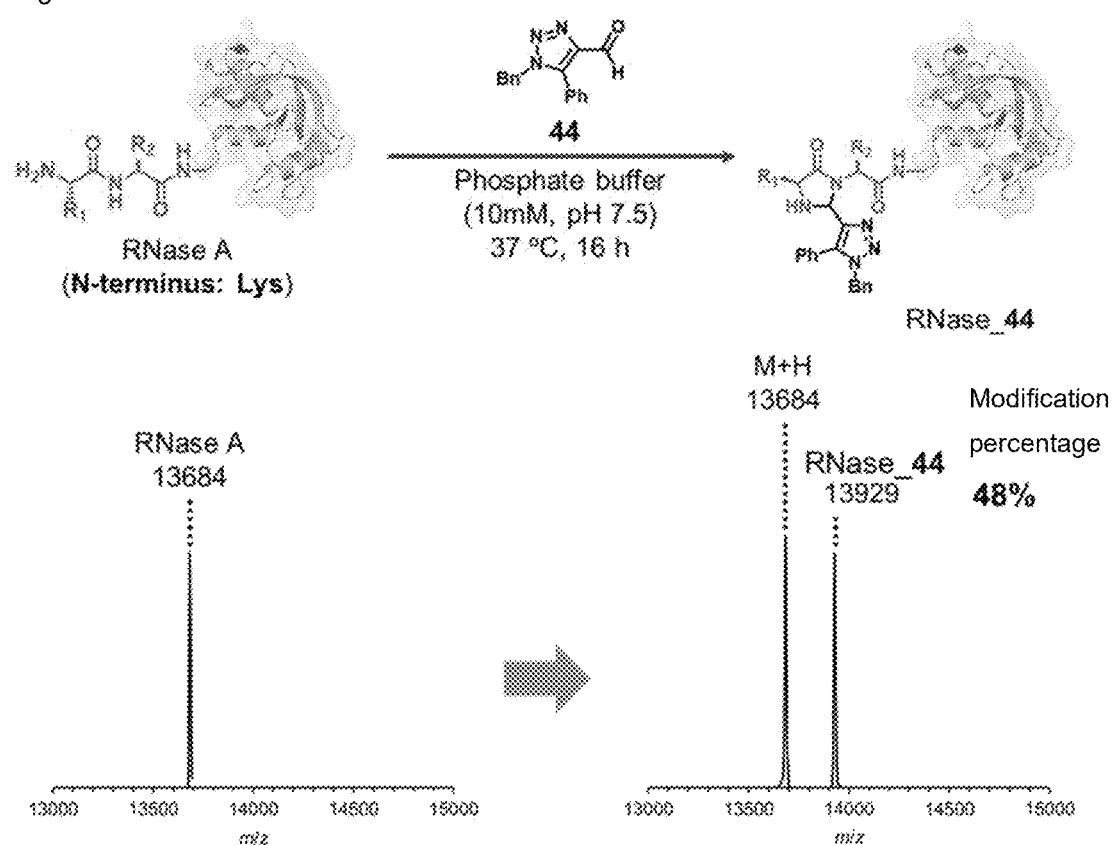
FIG. 67 shows the reaction scheme and results of N-terminal modification of RNase A (Example 21).

A solution of compound 44 in dimethyl sulfoxide (DMSO) (200 mM, 5 μL, 1.0 μmol, final concentration: 10 mM) was diluted with a phosphate buffer (10 mM, pH 7.5, 90 μL). A solution of RNase in ultrapure water (1 mM, 5 μL, 5 nmol, final concentration: 50 μM) was added thereto, and the mixture was shaken at 37° C. for 16 hours. The modification percentage (=(modified RNase)/(total RNase amount)) was evaluated from the peak intensity in a mass spectrum by using LC/MS. FIG. 67 shows the results. The modification percentage under this reaction condition was calculated as 48%.

Example 22. Modification to N-Terminus of Protein with Functional Molecule

Figure 68:
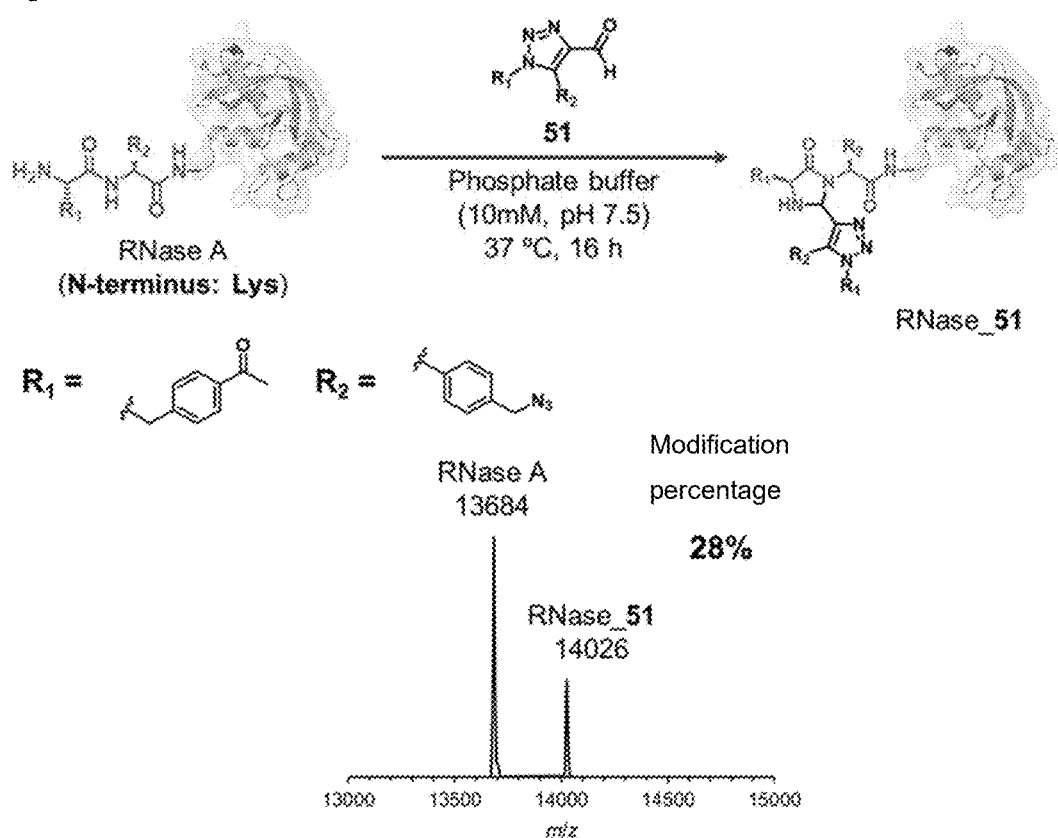
FIG. 68 shows the scheme and results of introduction of acetyl and azido groups into RNase A (Example 22-1).

22-1. Double Modification to N-Terminus of Protein with Acetyl and Azido Groups Double modification to the N-terminus of a protein with acetyl and azido groups was performed using compound 51 as a modifying agent by the same method as in Example 21. FIG. 68 shows the results of LC/MS analysis of the product. The modification percentage regarding the acetyl and azido groups was calculated as 28%.

Figure 69:
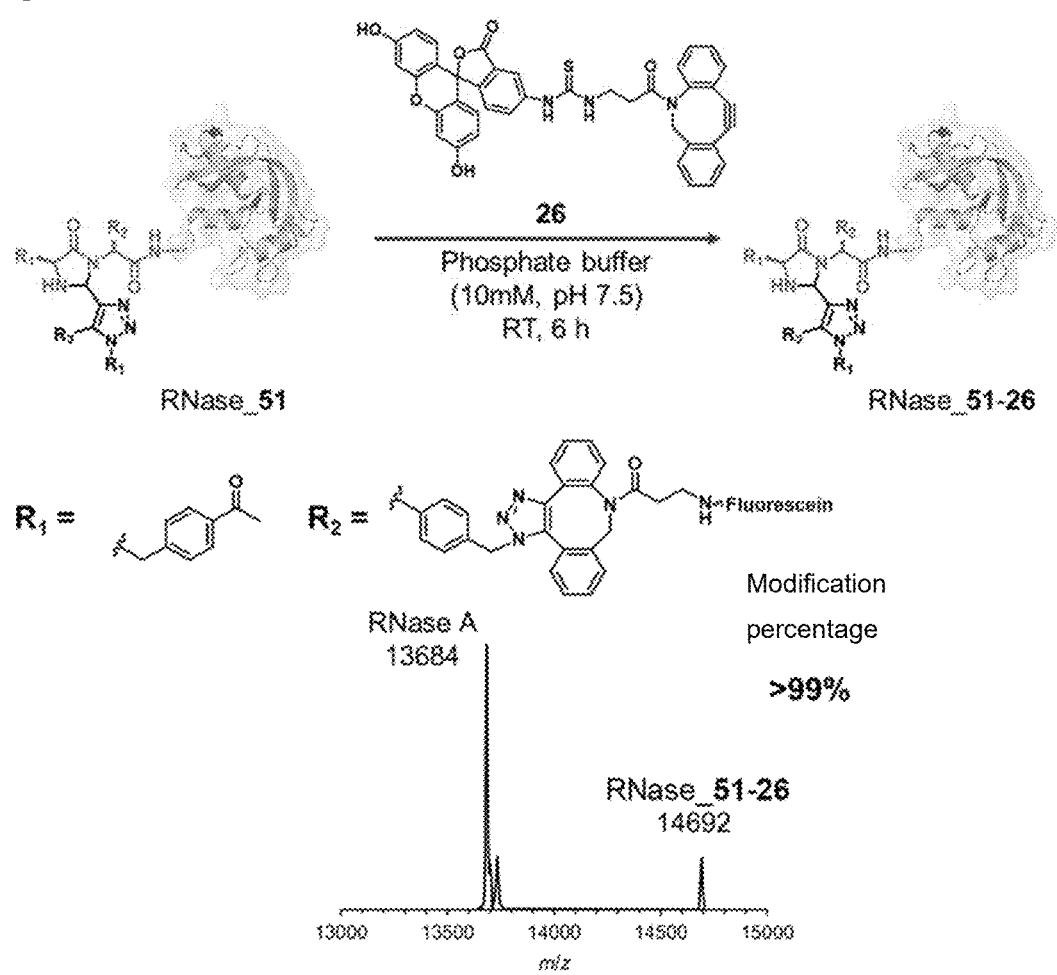
FIG. 69 shows modification with a fluorescent dye by a strain-promoted alkyne-azide cycloaddition reaction, and the results (Example 22-2).

22-2. Modification with Functional Molecule, Starting Fiom Azido Group with which N-Terminus of Protein is Modified The azido group-modified RNase prepared in Example 22-1 was modified with a fluorescent dye by a strain-promoted alkyne-azide cycloaddition reaction. Compound 26, fluorescein having a dibenzocyclooctyne moiety as an alkyne substrate, was used in the reaction. FIG. 69 shows the scheme and results.

A solution of compound 26 in dimethyl sulfoxide (DMSO) (8 mM, 1 μL, final concentration: 400 μM) was added to a phosphate buffer solution containing RNase_51 (RNase_51 concentration: 76 μM, final concentration: 20 μM, buffer solution concentration: 10 mM, pH 7.5, 19 μL), and the mixture was left to stand at room temperature for 6 hours. The modification percentage regarding the fluorescent dye moiety was calculated as >99%.

Example 23. Introduction of Polymer Molecule into N-Terminus of Protein 23-1. Synthesis of Polyethylene Glycol with Triazolecarbaldehyde Moiety Polyethylene glycol 54 in which a triazolecarbaldehyde moiety is introduced was synthesized. The synthesis was performed according to the following scheme with reference to published reports (L. Rocard, A. Berezin, F. De Leo, D. Bonifazi, Angew. Chem. Int. Ed., 2015, 54, 15739-15743; and M. B. van Eldijk, F. C. M. Smit, N. Vermue, M. F. Debets, S. Schoffelen, J. C. M. van Hest, Biomacromolecules, 2014, 15, 2751-2759).

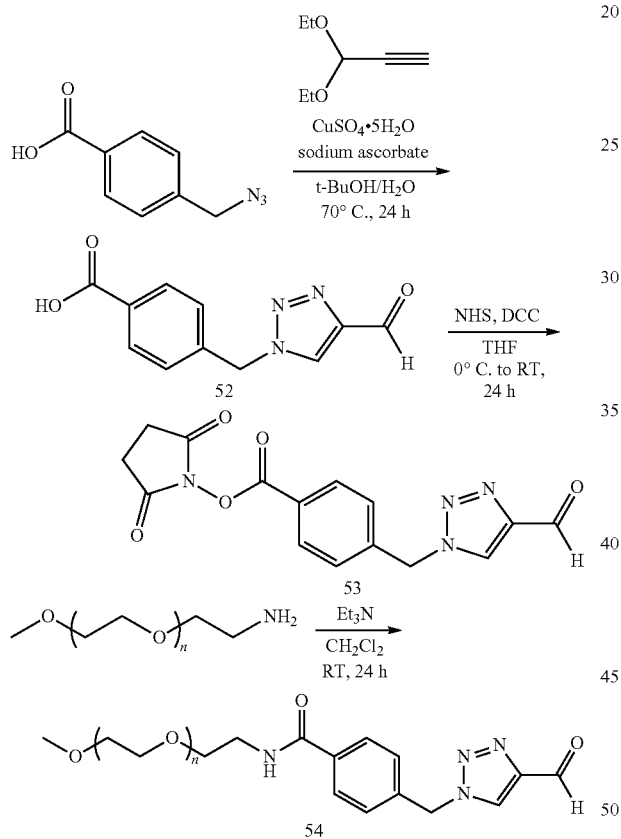

23-1-1. Synthesis of 4-((4-Formyl-1H-1,2,3-Triazol-1-Yl)Methyl)Benzoic Acid (52)

Figure 70:
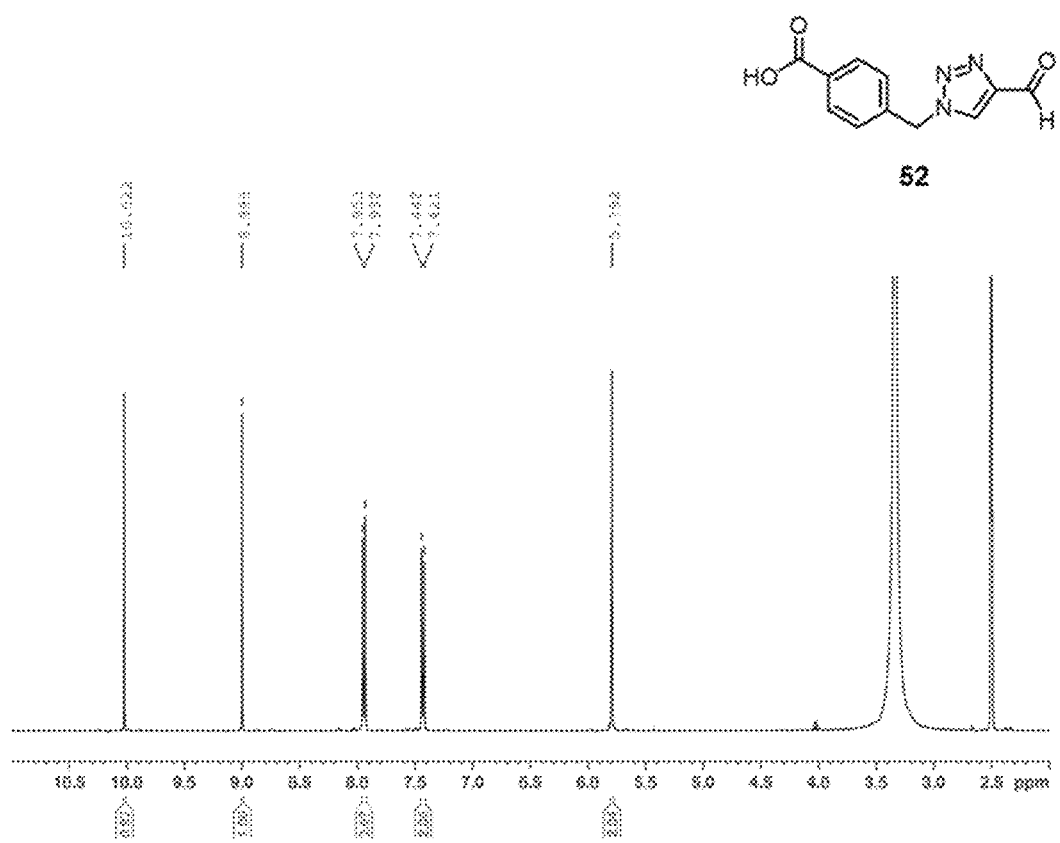
FIG. 70 shows the ¹H NMR spectrum (400 MHz, DMSO-d₆) of compound 52.

Compound 52 (white solid) was synthesized using (4-azidomethyl)benzoic acid as a precursor by using the same method (Method A) as in Example 1-3-1. FIG. 70 shows the $^1$H NMR spectrum.
Yield 71%; $^1$H NMR (400 MHz, DMSO-$d_6$): δ, 10.02 (s, 1H), 9.00 (s, 1H), 7.94 (d, J=8.0 Hz, 2H), 7.43 (d, J=8.0 Hz, 2H), 5.79 (s, 2H); $^{13}$C NMR (100 MHz, DMSO-$d_6$): δ, 185.0, 166.9, 147.1, 140.1, 130.7, 129.9, 128.7, 128.2, 52.8; ESI-TOF MS (positive mode) m/z calcd. for $C_1H_9N_3O_3Na$ [M+Na]$^+$ 254.054, found 254.053.

23-1-2. Synthesis of 2,5-Dioxopyrrolidin-1-Yl4-((4-Formyl-1H-1,2,3-Triazol-1-Yl)Methyl)Benzoate (53)

Figure 71:
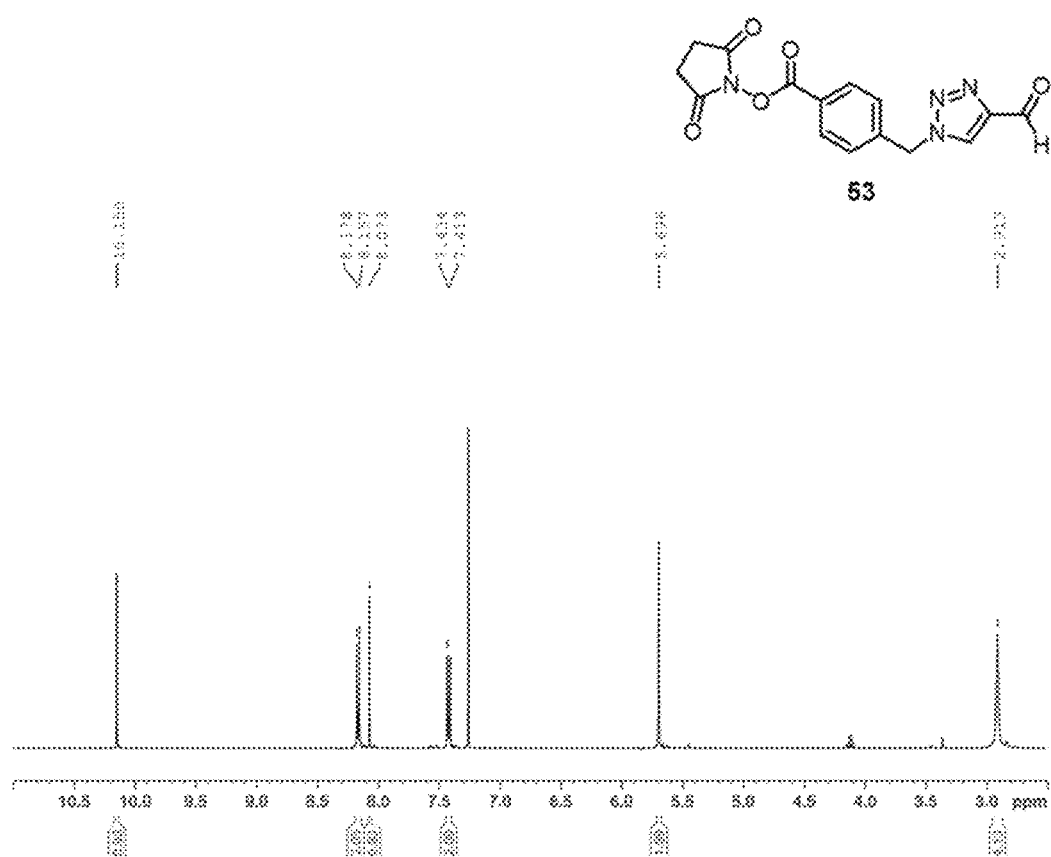
FIG. 71 shows the ¹H NMR spectrum (400 MHz, CDCl₃) of compound 53.

N-hydroxysuccinimide (138 mg, 1.2 mmol) and N,N'-dicyclohexylcarbodiimide (206 mg, 1.0 mmol) were added to a THF solution (10 mL) containing compound 52 (231 mg, 1.0 mmol), and the mixture was stirred at 0° C. for 24 hours under a nitrogen atmosphere. The precipitate was filtered off, and the filtrate was diluted with ethyl acetate (50 mL) and washed with a saturated sodium hydrogencarbonate aqueous solution (20 mL×2) and saturated saline (20 mL×2). The organic layer was dried over sodium sulfate, and the solvent was distilled off under reduced pressure to give a crude product. The crude product was purified by silica gel column chromatography to give compound 53 (white solid). FIG. 71 shows the $^1$H NMR spectrum.
Yield 71%; $^1$H NMR (400 MHz, CDCl$_3$): δ, 10.15 (s, 1H), 8.16 (d, J=8.5 Hz, 2H), 8.07 (s, 1H), 7.42 (d, J=8.5 Hz, 2H), 5.70 (s, 2H), 2.91 (s, 4H); $^{13}$C NMR (100 MHz, CDCl$_3$): δ, 185.0, 169.1, 161.3, 148.4, 140.5, 131.7, 128.5, 126.3, 125.4, 54.1, 25.8; ESI-TOF MS (positive mode) m/z calcd. for $C_{15}H_{12}N_4O_5Na$ [M+Na]$^+$ 351.070, found 351.069.

23-1-2. Synthesis of Polyethylene Glycol-Tethered Triazole-4-Carbaldehyde (54)

Polyethylene glycol terminated with an amino group (molecular weight: about 4000, 400 mg, 0.1 mmol) and triethylamine (45 L, 0.32 mmol) were added to methylene chloride (15 mL) containing compound 53 (53 mg, 0.16 mmol), and the mixture was stirred for 24 hours under a nitrogen atmosphere. After the solvent was distilled off under reduced pressure, the residue was purified by silica gel column chromatography. The resulting oily crude product was purified by reprecipitation (diethyl ether/methylene chloride) to give compound 54 (white solid).

23-2. Protein N-Terminal Modification Using Compound 54

Modification to the N-terminus of a protein with polyethylene glycol was performed using compound 54. The following is an example using ribonuclease as a substrate.

23-2-1. Reagent, solvent, etc.

Ribonuclease A (RNase) from bovine pancreas was purchased from Roche. Ultrapure water used was obtained by purification with Millipore Integral 3. As other reagents and solvents, commercially available products were used as is.

23-2-2. Modification to N-Terminus of Protein with Polyethylene Glycol

Figure 72:
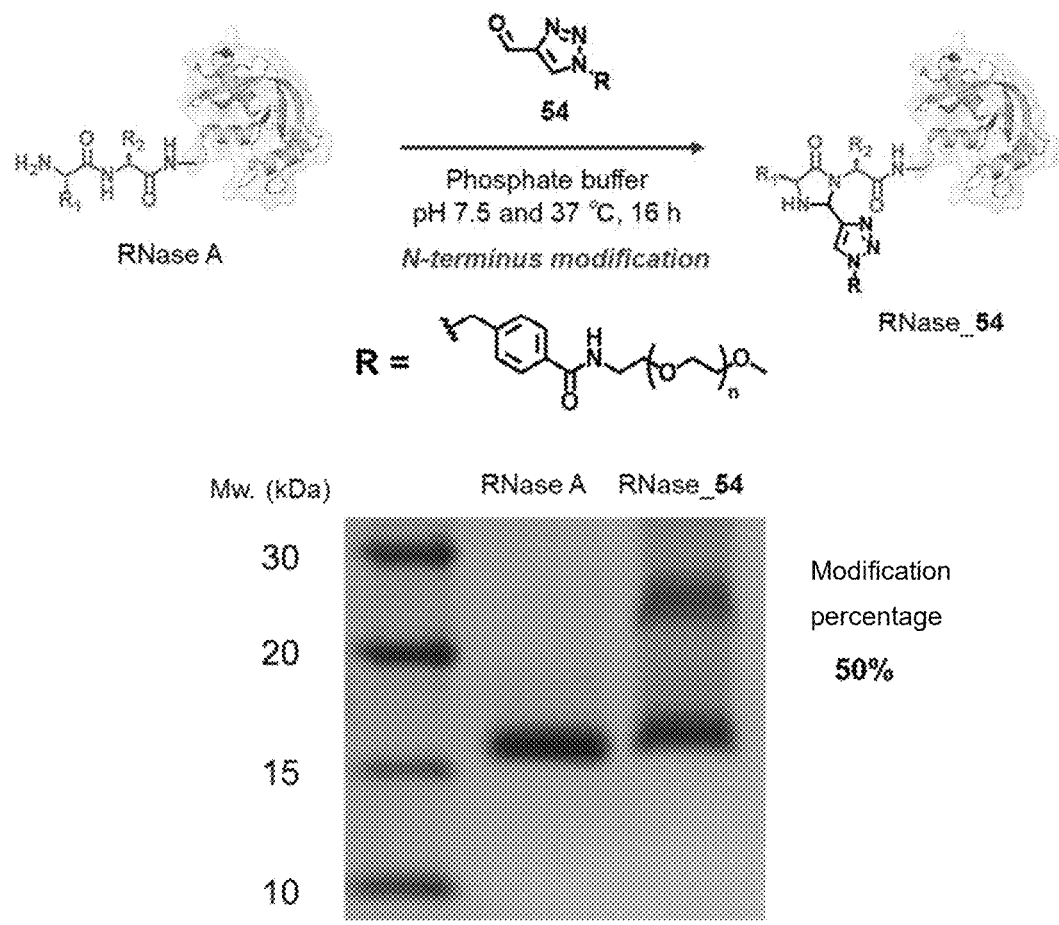
FIG. 72 shows the scheme and results of modification to RNase A with polyethylene glycol (Example 23-2-2).

Modification to the N-terminus of the protein with polyethylene glycol was performed using compound 54 as a modifying agent by the same method as in Example 10-2. FIG. 72 shows the results of SDS-PAGE analysis of the product. The modification percentage regarding the polyethylene glycol moiety was calculated as 50%.

23-2-3. Modification, with Polymer, to N-Terminus of Protein in which Cysteine Residue is Modified The N-terminus of HSA2 protein was polyethylene glycol-modified using compound 54 as a modifying agent by the same method as in Example 17-3. The HSA obtained by the reaction (referral to as "HSA4"), in which a cysteine residue is modified with an azido group and the N-terminus is modified with polyethylene glycol, was modified with a fluorescent dye by a strain-promoted alkyne-azide cycloaddition reaction using compound 26. The modified protein is referred to as "HSA5."

Figures 1, 73:
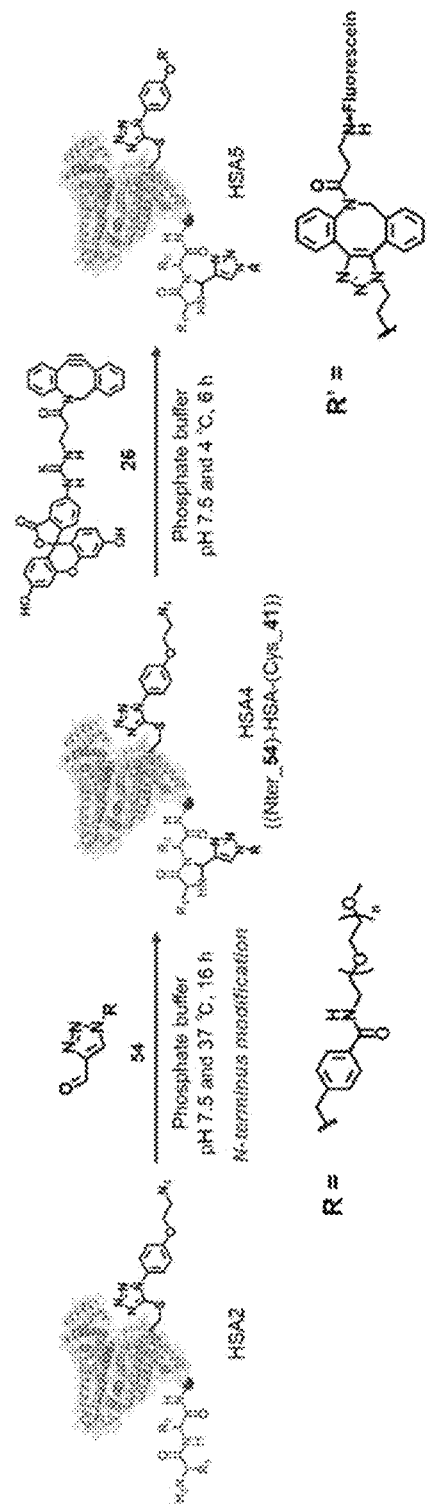
Figures 2, 73:
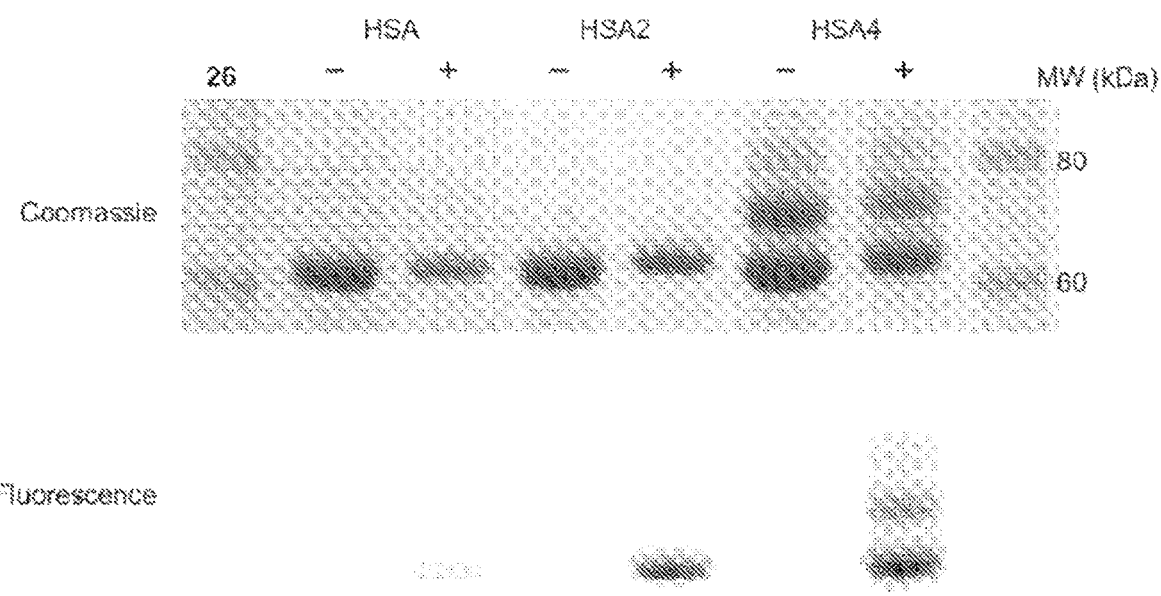

A solution of compound 26 in dimethyl sulfoxide (DMSO) (6 mM, 1 μL, final concentration: 300 μM) was added to a phosphate buffer solution containing HSA4 (HSA4 concentration: 62 μM, final concentration: 10 μM, buffer solution concentration: 10 mM, pH 7.5, 19 μL), and the mixture was left to stand at 4° C. for 6 hours. The same operation was also performed for HSA and HSA2, and the products were analyzed using SDS-PAGE. FIGS. 73A and 73B show the scheme and results.

Fluorescence was observed only in the lanes of HSA2 and HSA4 (both of which are modified with compound 41 to introduce an azido group) when reacted with compound 26. In addition, a new band appeared with an increase in the molecular weight only in the lane of HSA4 modified with compound 54, which is a polyethylene glycol derivative. These results confirmed that the modification with polyethylene glycol and modification with the fluorescent dye in the protein proceeded.

---

The invention claimed is:

1. A compound represented by formula (7) or a salt thereof, or a hydrate or solvate of the compound or a salt thereof,

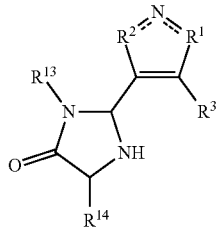

(7)

wherein one of $R^1$ and $R^2$ represents —N(—$R^4$)— (wherein $R^4$ represents an organic group or a group derived from an inorganic material), and the other represents =N—; $R^3$ represents a hydrogen atom, an organic group, or a group derived from an inorganic material; a double line composed of a dotted line and a solid line represents a single bond or a double bond; $R^{13}$ represents a group in which the N-terminal amino acid residue and —NH— adjacent thereto are excluded from a protein or peptide and the remaining protein or peptide is bonded through the carbon which was previously bonded to the —NH— adjacent to the N-terminal amino acid residue; and $R^{14}$ represents the side chain of the N-terminal amino acid residue of the protein or peptide.

2. A compound of claim 1 or a salt thereof, or a hydrate or solvate of the compound of claim 1 or a salt thereof, wherein the organic group is a group derived from an organic molecule or an organic molecular complex, and the organic molecule or the organic molecular complex is a functional substance.

3. A compound of claim 2 or a salt thereof, or a hydrate or solvate of the compound of claim 2 or a salt thereof, wherein the functional substance is a pharmaceutical compound, a luminescent molecule, a macromolecular compound, a ligand, a molecule to which a ligand binds, an antigenic protein, an antibody, a protein, a nucleic acid, a saccharide, a lipid, a cell, a virus, a label, a carbon electrode, a carbon nanomaterial, a linker, a spacer molecule, or a complex or linked molecule thereof.

4. A compound of claim 1 or a salt thereof, or a hydrate or solvate of the compound of claim 1 or a salt thereof, wherein the inorganic material is an electrode material, metal fine particles, metal oxide fine particles, semiconductor particles, or magnetic particles.

* * * * *